US008541649B2

(12) United States Patent
Wang et al.

(10) Patent No.: US 8,541,649 B2
(45) Date of Patent: Sep. 24, 2013

(54) BRASSINOSTEROID REGULATED KINASES (BRKS) THAT MEDIATE BRASSINOSTEROID SIGNAL TRANSDUCTION AND USES THEREOF

(75) Inventors: Zhi-Yong Wang, Stanford, CA (US); Wenqiang Tang, Stanford, CA (US)

(73) Assignee: Carnegie Institution of Washington, Washington, DC (US)

( * ) Notice: Subject to any disclaimer, the term of this patent is extended or adjusted under 35 U.S.C. 154(b) by 370 days.

(21) Appl. No.: 12/506,895

(22) Filed: Jul. 21, 2009

(65) Prior Publication Data

US 2010/0043097 A1 Feb. 18, 2010

Related U.S. Application Data

(60) Provisional application No. 61/082,444, filed on Jul. 21, 2008.

(51) Int. Cl.

| | |
|---|---|
| ***A01H 1/00*** | (2006.01) |
| ***A01H 5/00*** | (2006.01) |
| ***C12N 15/82*** | (2006.01) |
| ***A61K 39/00*** | (2006.01) |
| ***C07K 14/415*** | (2006.01) |

(52) U.S. Cl.
USPC ........... 800/278; 800/289; 800/290; 800/298; 435/419; 435/468; 424/185.1; 530/370

(58) Field of Classification Search
None
See application file for complete search history.

(56) References Cited

U.S. PATENT DOCUMENTS

| | | | | |
|---|---|---|---|---|
| 2006/0150283 | A1 * | 7/2006 | Alexandrov et al. ......... | 800/288 |
| 2007/0124833 | A1 * | 5/2007 | Abad et al. .................... | 800/278 |

OTHER PUBLICATIONS

Chono et al. "A Semidwarf phenotype of barley uzu results from a nucleotide substitution in the gene encoding a putative brassinosteroid receptor." Plant Physiology 133: 1209-1219, 2003.

Q56I15_SOYBN UniProKB/TrEMBL.Direct Submission. "Stress inducible protein kinase from Glycine Max (Soybean)." 2008.

A9SRS2_PHYPA UniProKB/TrEMBL.Direct Submission. "Predicted protein (fragment) ORFNames=PHYPADRAFT_134217. *Physcomitrella patens* subsp. patens." 2008.

A5C572_VITVI UniProKB/TrEMBL.Direct Submission. "Putative uncharacterized protein. *Vitis vinifera* (Grape)." 2008.

Tang et al. "Brassinosteroid-Signaling Kinases (BSKs) mediate signal transduction from the receptor BRI1 in *Arabidopsis*." Science 321: 557-560, 2008.

Kim et al. "Brassinosteroid signal transduction from cell-surface receptor kinases to nuclear transcription factors." Nature Cell Biology 11: 1254-1262, 2009.

International Search Report issued in corresponding PCT Application No. PCT/US2009/004207, mailed Apr. 19, 2010.

* cited by examiner

*Primary Examiner* — Eileen B O Hara

(74) *Attorney, Agent, or Firm* — Morgan, Lewis & Bockius LLP

(57) ABSTRACT

The present invention identifies a novel family of kinases regulated by brassinosteroids, referred to as BRKs (brassinosteroid regulated kinases) or BSKs (brassinosteroid signaling kinases). The present invention provides methods for modulating the response of a plant cell to a brassinosteroid using BRKs.

17 Claims, 18 Drawing Sheets

| Spots | Protein ID | Unique peptides | Sequence coverage |
|---|---|---|---|
| 1 | BSK1 | 6 | 18% |
| 2 | BSK1 | 6 | 16% |
| 3 | BSK2 | 24 | 66% |
| 4 | BSK2 | 16 | 53% |
| 5 | BSK2 | 10 | 29% |

Figure 7A

BSK1
BSK11
BSK2
BSK3
BSK4
BSK5
BSK6
BSK7
BSK8
BSK9
BSK10
BSK12
Consistency

Figure 7B:
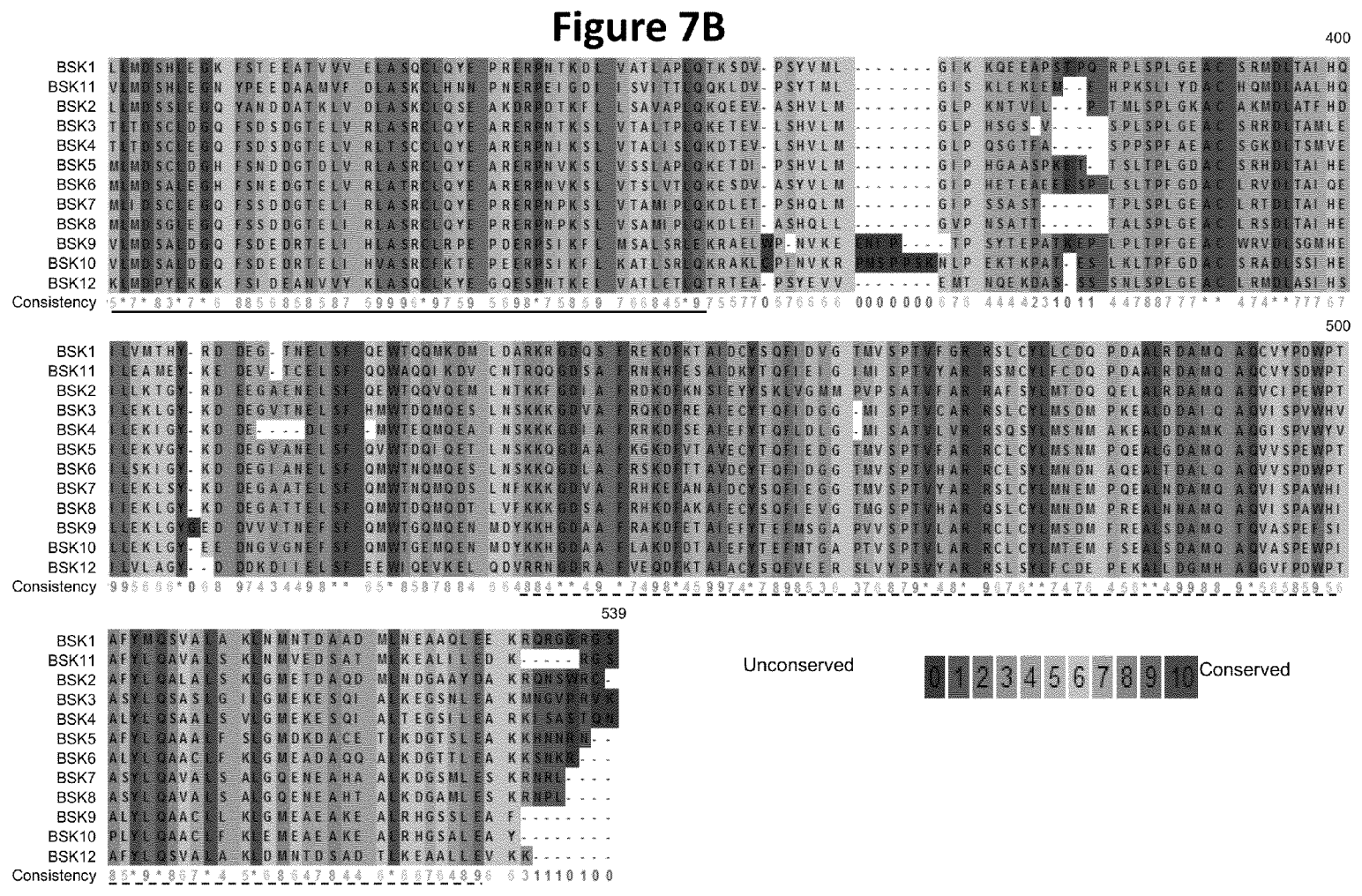

BSK1
BSK11
BSK2
BSK3
BSK4
BSK5
BSK6
BSK7
BSK8
BSK9
BSK10
BSK12
Consistency

Unconserved 0 1 2 3 4 5 6 7 8 9 10 Conserved

A

B

SEQUENCE LISTING

```
<160> NUMBER OF SEQ ID NOS: 37

<210> SEQ ID NO 1
<211> LENGTH: 1802
<212> TYPE: DNA
<213> ORGANISM: Arabidopsis thaliana

<400> SEQUENCE: 1

aaggagcgaa agagaaacac tttccgactt gggtaaggaa aaagagtttg atgggttgtt      60
gtcaatcctt gttttccggc gataacccac ttgggaaaga tggagttcag ccgcaaccac     120
tatctcaaaa caatcacggc ggagctacga cggctgataa cggcggaagc ggcggagcta     180
gtggtgtagg cggcggagga ggaggaggag gaatcccatc tttctctgag ttctctttcg     240
ctgaccttaa agcagctaca aacaacttta gctcagacaa catcgtatca gaaagtggtg     300
agaaagcccc aaatcttgtc tacaaaggcc gacttcagaa ccgtcgttgg atcgctgtca     360
agaagtttac taagatggct tggcctgagc ctaaacaatt tgcggaagaa gcatggggtg     420
tggggaaatt gaggcataat cgattagcga atttgattgg atattgttgt gatggagatg     480
agaggcttct tgttgctgag ttcatgccta atgatactct tgctaagcat ttgttccatt     540
gggaaaatca gacaattgag tgggctatga ggttgcgagt aggatattac atagctgagg     600
ctttggatta ttgtagtact gagggtcgtc cattgtacca tgatttgaat gcttataggg     660
ttctctttga tgaggatggt gatcctcgtc tctcatgttt tggcttgatg aagaacagta     720
gggatggtaa aagttatagc acaaatttag cttatacacc acctgaatat ctaagaaatg     780
gaagagtgac acctgaaagt gttacgtata gctttggaac tgtccttctg gatttgctta     840
gcggaaaaca catccctcca agccatgctc tcgatatgat acgaggcaag aatattattc     900
tgttgatgga ttcacacctc gaaggaaagt tctcaacaga agaggctact gtagtggtcg     960
aactcgcctc tcaatgttta caatatgagc ctcgagagag accaaataca aaagatcttg    1020
ttgcaacact tgcaccattg caaactaaat cagacgttcc atcttatgtg atgcttggaa    1080
taaagaagca agaggaggca ccttcgactc cacagagacc actttcgcca ttaggtgagg    1140
cctgctcaag aatggatctc acagctattc atcagatttt ggtcatgaca cattacagag    1200
acgacgaggg cacaaacgag ttatcattcc aagaatggac tcaacaaatg aaagatatgc    1260
```

```
ttgatgcacg gaaacgcggt gatcaatctt tccgcgagaa agatttcaaa acagccatcg   1320

actgttactc acagttcatt gacgttggaa caatggtatc tccaactgta tttggtcggc   1380

gaagtctatg ctacttacta tgcgatcaac cagatgcagc actacgcgac gcaatgcaag   1440

cgcagtgtgt gtatccggat tggccaacag ctttctacat gcagtctgtg gcattagcga   1500

agctgaacat gaacacagac gcagccgata tgttgaacga agcagctcag ctcgaagaaa   1560

agagacaacg aggcggcaga ggatcttgat tcttgagaca caaagtgtta catcttgttg   1620

taaaatttga tgagcttcaa gaattctttt taagaagaag agaaagaaaa aatacggtta   1680

aaaacttgtt gctggattgt ttgattgggg atgtaatgta accataggga gagaaaacaa   1740

ttgaatgttt gtttgtatgc aatacatgtt gtaagtttta atggtcaaat gtttcgaaaa   1800

ta                                                                  1802


<210> SEQ ID NO 2
<211> LENGTH: 512
<212> TYPE: PRT
<213> ORGANISM: Arabidopsis thaliana

<400> SEQUENCE: 2

Met Gly Cys Cys Gln Ser Leu Phe Ser Gly Asp Asn Pro Leu Gly Lys
1               5                   10                  15

Asp Gly Val Gln Pro Gln Pro Leu Ser Gln Asn Asn His Gly Gly Ala
            20                  25                  30

Thr Thr Ala Asp Asn Gly Gly Ser Gly Gly Ala Ser Gly Val Gly Gly
        35                  40                  45

Gly Gly Gly Gly Gly Gly Ile Pro Ser Phe Ser Glu Phe Ser Phe Ala
    50                  55                  60

Asp Leu Lys Ala Ala Thr Asn Asn Phe Ser Ser Asp Asn Ile Val Ser
65                  70                  75                  80

Glu Ser Gly Glu Lys Ala Pro Asn Leu Val Tyr Lys Gly Arg Leu Gln
                85                  90                  95

Asn Arg Arg Trp Ile Ala Val Lys Lys Phe Thr Lys Met Ala Trp Pro
            100                 105                 110

Glu Pro Lys Gln Phe Ala Glu Glu Ala Trp Gly Val Gly Lys Leu Arg
        115                 120                 125

His Asn Arg Leu Ala Asn Leu Ile Gly Tyr Cys Cys Asp Gly Asp Glu
    130                 135                 140

Arg Leu Leu Val Ala Glu Phe Met Pro Asn Asp Thr Leu Ala Lys His
145                 150                 155                 160

Leu Phe His Trp Glu Asn Gln Thr Ile Glu Trp Ala Met Arg Leu Arg
                165                 170                 175

Val Gly Tyr Tyr Ile Ala Glu Ala Leu Asp Tyr Cys Ser Thr Glu Gly
            180                 185                 190

Arg Pro Leu Tyr His Asp Leu Asn Ala Tyr Arg Val Leu Phe Asp Glu
        195                 200                 205

Asp Gly Asp Pro Arg Leu Ser Cys Phe Gly Leu Met Lys Asn Ser Arg
    210                 215                 220

Asp Gly Lys Ser Tyr Ser Thr Asn Leu Ala Tyr Thr Pro Pro Glu Tyr
225                 230                 235                 240

Leu Arg Asn Gly Arg Val Thr Pro Glu Ser Val Thr Tyr Ser Phe Gly
                245                 250                 255

Thr Val Leu Leu Asp Leu Leu Ser Gly Lys His Ile Pro Pro Ser His
            260                 265                 270
```

```
Ala Leu Asp Met Ile Arg Gly Lys Asn Ile Ile Leu Leu Met Asp Ser
        275                 280                 285

His Leu Glu Gly Lys Phe Ser Thr Glu Glu Ala Thr Val Val Val Glu
    290                 295                 300

Leu Ala Ser Gln Cys Leu Gln Tyr Glu Pro Arg Glu Arg Pro Asn Thr
305                 310                 315                 320

Lys Asp Leu Val Ala Thr Leu Ala Pro Leu Gln Thr Lys Ser Asp Val
                325                 330                 335

Pro Ser Tyr Val Met Leu Gly Ile Lys Lys Gln Glu Glu Ala Pro Ser
            340                 345                 350

Thr Pro Gln Arg Pro Leu Ser Pro Leu Gly Glu Ala Cys Ser Arg Met
        355                 360                 365

Asp Leu Thr Ala Ile His Gln Ile Leu Val Met Thr His Tyr Arg Asp
    370                 375                 380

Asp Glu Gly Thr Asn Glu Leu Ser Phe Gln Glu Trp Thr Gln Gln Met
385                 390                 395                 400

Lys Asp Met Leu Asp Ala Arg Lys Arg Gly Asp Gln Ser Phe Arg Glu
                405                 410                 415

Lys Asp Phe Lys Thr Ala Ile Asp Cys Tyr Ser Gln Phe Ile Asp Val
            420                 425                 430

Gly Thr Met Val Ser Pro Thr Val Phe Gly Arg Arg Ser Leu Cys Tyr
        435                 440                 445

Leu Leu Cys Asp Gln Pro Asp Ala Ala Leu Arg Asp Ala Met Gln Ala
    450                 455                 460

Gln Cys Val Tyr Pro Asp Trp Pro Thr Ala Phe Tyr Met Gln Ser Val
465                 470                 475                 480

Ala Leu Ala Lys Leu Asn Met Asn Thr Asp Ala Ala Asp Met Leu Asn
                485                 490                 495

Glu Ala Ala Gln Leu Glu Glu Lys Arg Gln Arg Gly Gly Arg Gly Ser
            500                 505                 510
```

<210> SEQ ID NO 3
<211> LENGTH: 1963
<212> TYPE: DNA
<213> ORGANISM: Arabidopsis thaliana

<400> SEQUENCE: 3

```
acctctattt tttcaagtct gcagcttttt gaagctatat ttttcagatc tttcactctc     60

tctctagcta cttctttttg tctttaagtt ttcaaatttt attaaatttt tatattctac    120

tgcctcctca gcttctctca caaagcacaa atccaagccc caaatcaaat cccaccattg    180

ttttattacc tcaatccaag aacactagac acaacaaaaa tctctgtttc ttatccaaat    240

ttctgatctt tgtggagaac aatattttga ttggatgtga gacaaatggg ttgtttacat    300

tccaaaactg ctaatcttcc ttcttctgat gatccatcag ctccaaacaa accagaatca    360

gtaaatgggg accaagtgga tcaggaaatc caaaatttca aagaatttga actaaatgag    420

ttgaggaaag ctaccaatgg gtttagtcct agctgcattg tctctgaagg tggagagaaa    480

gctcctaatg tcgtttacag agggaagctt gaagggaatc atcttgtagc tatcaagcga    540

ttctctaggc aatcttggcc tgatgctcaa cagtttgtgg tggaagcgac tggtgttggg    600

aagcttagaa acaagagaat agttagtttg atcggttgct gtgctgaagg agatgagagg    660

ttgttggtgg cagagtatat gcccaatgat actctctcaa agcatctctt ccactgggaa    720

aagcagccac ttccatggga tatgcgtgtt cgaatcgcag actatattgc agaagcactt    780

gattactgca atattgagaa ccgaaaaatc tatcatgacc tcaatgcata cagaatcctc    840
```

```
ttcgacgagg aaggtgatcc tcgtctatct acttttggtc ttatgaagaa cagtagagat    900

ggcaaaagct atagcacaaa cttagcttat actccacctg agtttttacg gacaggtaga    960

gtcattcctg aaagtgtgat attcagttat ggaactattc ttttagatct tttaagcggc   1020

aaacacattc cacctagcca tgcccttgat atcataagag ggaaaaatgc tttgcttctt   1080

atggattcat ctcttgaagg gcaatatgcg aatgatgatg cgactaaatt agttgatctt   1140

gcttcaaaat gccttcaatc agaggcaaag gatcgaccag ataccaaatt tcttctctct   1200

gcagtagcac cactacaaaa gcaagaagag gttgcttctc atgtcttaat gggcttacca   1260

aagaacacag taatattacc aactatgctt tctcctcttg gaaaggcctg tgcaaagatg   1320

gaccttgcga catttcacga cattttgctt aaaaccggtt acagagatga agaaggtgca   1380

gaaaatgagc tttcatttca agaatggaca caacaagtgc aggagatgct taacacaaaa   1440

aagttcgggg acattgcttt cagagacaag gatttcaaga actcaattga atactactcc   1500

aagttggtgg ggatgatgcc ggttccttct gcaacagttt tcgctagacg ggctttctcc   1560

tacttaatga cagaccaaca ggagcttgca ctgagagatg caatgcaggc acaggtgtgc   1620

ataccagaat ggccaacagc tttttacttg caggctttag cgctctcaaa gctcggaatg   1680

gagactgatg ctcaagatat gctcaacgat ggcgctgcat atgatgctaa gcgacagaat   1740

agctggcgct gctaagctat tagaggaagt cccaaatatt tatgggtctt ttcagactgt   1800

aactgaaagg tgtgtatgca tgtaagagag agatggaatg tgttgtttac ttttgtgaaa   1860

tgagagcttc ttttttgca tgaatcttta tgaaaagtca aatcttttgg ggaaagagag   1920

aataagactg caaataacta atttgattcc ttcttcctta tgg                     1963
```

```
<210> SEQ ID NO 4
<211> LENGTH: 489
<212> TYPE: PRT
<213> ORGANISM: Arabidopsis thaliana

<400> SEQUENCE: 4

Met Gly Cys Leu His Ser Lys Thr Ala Asn Leu Pro Ser Ser Asp Asp
1               5                   10                  15

Pro Ser Ala Pro Asn Lys Pro Glu Ser Val Asn Gly Asp Gln Val Asp
            20                  25                  30

Gln Glu Ile Gln Asn Phe Lys Glu Phe Glu Leu Asn Glu Leu Arg Lys
        35                  40                  45

Ala Thr Asn Gly Phe Ser Pro Ser Cys Ile Val Ser Glu Gly Gly Glu
    50                  55                  60

Lys Ala Pro Asn Val Val Tyr Arg Gly Lys Leu Glu Gly Asn His Leu
65                  70                  75                  80

Val Ala Ile Lys Arg Phe Ser Arg Gln Ser Trp Pro Asp Ala Gln Gln
                85                  90                  95

Phe Val Val Glu Ala Thr Gly Val Gly Lys Leu Arg Asn Lys Arg Ile
            100                 105                 110

Val Ser Leu Ile Gly Cys Cys Ala Glu Gly Asp Glu Arg Leu Leu Val
        115                 120                 125

Ala Glu Tyr Met Pro Asn Asp Thr Leu Ser Lys His Leu Phe His Trp
    130                 135                 140

Glu Lys Gln Pro Leu Pro Trp Asp Met Arg Val Arg Ile Ala Asp Tyr
145                 150                 155                 160

Ile Ala Glu Ala Leu Asp Tyr Cys Asn Ile Glu Asn Arg Lys Ile Tyr
                165                 170                 175
```

```
His Asp Leu Asn Ala Tyr Arg Ile Leu Phe Asp Glu Glu Gly Asp Pro
            180                 185                 190

Arg Leu Ser Thr Phe Gly Leu Met Lys Asn Ser Arg Asp Gly Lys Ser
        195                 200                 205

Tyr Ser Thr Asn Leu Ala Tyr Thr Pro Pro Glu Phe Leu Arg Thr Gly
    210                 215                 220

Arg Val Ile Pro Glu Ser Val Ile Phe Ser Tyr Gly Thr Ile Leu Leu
225                 230                 235                 240

Asp Leu Leu Ser Gly Lys His Ile Pro Pro Ser His Ala Leu Asp Ile
                245                 250                 255

Ile Arg Gly Lys Asn Ala Leu Leu Leu Met Asp Ser Ser Leu Glu Gly
            260                 265                 270

Gln Tyr Ala Asn Asp Asp Ala Thr Lys Leu Val Asp Leu Ala Ser Lys
        275                 280                 285

Cys Leu Gln Ser Glu Ala Lys Asp Arg Pro Asp Thr Lys Phe Leu Leu
    290                 295                 300

Ser Ala Val Ala Pro Leu Gln Lys Gln Glu Glu Val Ala Ser His Val
305                 310                 315                 320

Leu Met Gly Leu Pro Lys Asn Thr Val Ile Leu Pro Thr Met Leu Ser
                325                 330                 335

Pro Leu Gly Lys Ala Cys Ala Lys Met Asp Leu Ala Thr Phe His Asp
            340                 345                 350

Ile Leu Leu Lys Thr Gly Tyr Arg Asp Glu Glu Gly Ala Glu Asn Glu
        355                 360                 365

Leu Ser Phe Gln Glu Trp Thr Gln Gln Val Gln Glu Met Leu Asn Thr
    370                 375                 380

Lys Lys Phe Gly Asp Ile Ala Phe Arg Asp Lys Asp Phe Lys Asn Ser
385                 390                 395                 400

Ile Glu Tyr Tyr Ser Lys Leu Val Gly Met Met Pro Val Pro Ser Ala
                405                 410                 415

Thr Val Phe Ala Arg Arg Ala Phe Ser Tyr Leu Met Thr Asp Gln Gln
            420                 425                 430

Glu Leu Ala Leu Arg Asp Ala Met Gln Ala Gln Val Cys Ile Pro Glu
        435                 440                 445

Trp Pro Thr Ala Phe Tyr Leu Gln Ala Leu Ala Leu Ser Lys Leu Gly
    450                 455                 460

Met Glu Thr Asp Ala Gln Asp Met Leu Asn Asp Gly Ala Ala Tyr Asp
465                 470                 475                 480

Ala Lys Arg Gln Asn Ser Trp Arg Cys
                485
```

<210> SEQ ID NO 5
<211> LENGTH: 2495
<212> TYPE: DNA
<213> ORGANISM: Arabidopsis thaliana

<400> SEQUENCE: 5

```
acacccatta aaatatttca tcaacttgtc ggtaaaatta attcttggct tattctatct      60

ttctttctct gtcttcttct ttcaattttt caataacaat aatacagatg tgtatacatt     120

agatacacgt atactagtac taaacttcac tgtgtgatct gatctagagt ttttatacta     180

tcagaataaa taatagtcga caatttggga tttgtttatg gtttacttca catgaatcac     240

atacgttcat gtcgattcct ttgagatact gtctcgattt cgtttttttc tcttgtttaa     300

tttaaaatta ttgtaaagca cgtggatttg cttgtcttgg ttttgttttc tccttcgacc     360
```

```
tctttgatga aatcgaggaa cctacaattt cttcgtcgat ccaaatggta gcttagtggt    420

ggtgataata ggtttctcct cttgattggc tccagcttta ggtttttttt tttatctttg    480

tttctgcttc gattcccaaa atttaccctt tcgattttga gtctaactag tcgagttgac    540

tcagtagagt cgaaagcttc tgggtttacg aagagacatc tcctaattga aacaaaacct    600

ttcctttcca ttgggctgag aaaaaagcaa gagtctttga atattttttg gagcgtggtt    660

ttatttagat gggaggtcaa tgctctagcc tgagttgttg caggaacact tcacacaaga    720

cagctgttct tgaagctcct gatgttgata atggagagag tagtgagatc actgatgttc    780

ctaatttccg ggagtatact ttagaacagc ttaaggcagc tacttctggt tttgccgtgg    840

agtatattgt atctgaacat ggagaaaagg ctccaaatgt tgtctataaa gggaaattgg    900

agaaccaaaa gaagattgct gtcaagcgtt ttactagaat ggcctggcct gattcacgac    960

agttcttgga ggaagcgagg tcggttggtc agctacggag tgagagaatg gccaatttac   1020

tcggatgttg ctgcgaaggt gacgagaggt tacttgtagc agagtttatg cctaatgaaa   1080

cactagccaa acaccttttt cactgggaaa ctcaacctat gaaatggact atgaggctac   1140

gagttgtttt atatctagca caagctcttg aatactgcac cagcaaaggc cgtactcttt   1200

accacgacct caatgcttac cggggttttgt ttgatgagga atgcaatcca agactatcta   1260

cttttggctt gatgaagaat agtcgggatg gaaaaagtta cagcactaat cttgctttca   1320

cccctcctga atatctacga actgggagaa ttactccaga gagtgtaata tacagctttg   1380

gcactcttct gcttgatctt ctcagcggaa aacatatacc tcctagccat gcccttgatc   1440

tgattagaga cagaaatctc cagacgctaa ctgattcttg cctagatggg cagttttctg   1500

atagtgatgg tacagagcta gtacgcctag cttctcgttg tcttcagtat gaagctcgtg   1560

agcggccaaa caccaaatct ttagtgactg ccttgacacc tcttcagaag gagacagagg   1620

tcctgtctca tgttctaatg ggtctacctc acagtggttc agtctctcct ctgtcccctc   1680

ttggtgaggc ttgttcaaga agggacctga ccgctatgct tgagatcctg gagaaacttg   1740

gatacaaaga cgacgagggt gtcaccaatg agctctcgtt tcatatgtgg acagaccaga   1800

tgcaagagtc tttgaactcg aagaagaagg gtgatgtggc tttcaggcaa aaagacttta   1860

gagaggccat cgagtgttac acacagttta ttgatggagg aatgatctct ccaacagtgt   1920

gtgctcggcg tagtctgtgt tacctaatga gtgacatgcc gaaagaagct ttagatgatg   1980

caattcaggc tcaagtgatc tctcccgtgt ggcatgtcgc atcatatctg cagtctgctt   2040

cccttggtat cctgggaatg gagaaggaat ctcaaatcgc actgaaagag ggctcgaacc   2100

ttgaagcaaa gatgaatgga gttccccgag tgaagtaaga tatatagcat ttaagatttt   2160

tcttgttggg aaagatgaaa gaacatctta ccaagtaaaa ggggtatgaa tcttttgagc   2220

acaatgatgg gaaaacactc aagagcaatg caaaactata gaccctcttc ttctggttgt   2280

atgaggtgtt ttgcccttct tgtgcctctt tttatgggca ttgaattgaa ggagtcattt   2340

cctttattag ctttgaaatc catttcctga aactttattg tactaaaaaa cccattattg   2400

cagaaaccaa aagagggttt tgtttctttt gatctatagg tcacacagac taaacatgta   2460

tgaactcttg tcttttgact aaagagatat tcgac                              2495
```

<210> SEQ ID NO 6
<211> LENGTH: 489
<212> TYPE: PRT
<213> ORGANISM: Arabidopsis thaliana

<400> SEQUENCE: 6

```
Met Gly Gly Gln Cys Ser Ser Leu Ser Cys Cys Arg Asn Thr Ser His
1               5                   10                  15

Lys Thr Ala Val Leu Glu Ala Pro Asp Val Asp Asn Gly Glu Ser Ser
            20                  25                  30

Glu Ile Thr Asp Val Pro Asn Phe Arg Glu Tyr Thr Leu Glu Gln Leu
        35                  40                  45

Lys Ala Ala Thr Ser Gly Phe Ala Val Glu Tyr Ile Val Ser Glu His
    50                  55                  60

Gly Glu Lys Ala Pro Asn Val Val Tyr Lys Gly Lys Leu Glu Asn Gln
65                  70                  75                  80

Lys Lys Ile Ala Val Lys Arg Phe Thr Arg Met Ala Trp Pro Asp Ser
                85                  90                  95

Arg Gln Phe Leu Glu Glu Ala Arg Ser Val Gly Gln Leu Arg Ser Glu
            100                 105                 110

Arg Met Ala Asn Leu Leu Gly Cys Cys Cys Glu Gly Asp Glu Arg Leu
        115                 120                 125

Leu Val Ala Glu Phe Met Pro Asn Glu Thr Leu Ala Lys His Leu Phe
    130                 135                 140

His Trp Glu Thr Gln Pro Met Lys Trp Thr Met Arg Leu Arg Val Val
145                 150                 155                 160

Leu Tyr Leu Ala Gln Ala Leu Glu Tyr Cys Thr Ser Lys Gly Arg Thr
                165                 170                 175

Leu Tyr His Asp Leu Asn Ala Tyr Arg Val Leu Phe Asp Glu Glu Cys
            180                 185                 190

Asn Pro Arg Leu Ser Thr Phe Gly Leu Met Lys Asn Ser Arg Asp Gly
        195                 200                 205

Lys Ser Tyr Ser Thr Asn Leu Ala Phe Thr Pro Pro Glu Tyr Leu Arg
    210                 215                 220

Thr Gly Arg Ile Thr Pro Glu Ser Val Ile Tyr Ser Phe Gly Thr Leu
225                 230                 235                 240

Leu Leu Asp Leu Leu Ser Gly Lys His Ile Pro Pro Ser His Ala Leu
                245                 250                 255

Asp Leu Ile Arg Asp Arg Asn Leu Gln Thr Leu Thr Asp Ser Cys Leu
            260                 265                 270

Asp Gly Gln Phe Ser Asp Ser Asp Gly Thr Glu Leu Val Arg Leu Ala
        275                 280                 285

Ser Arg Cys Leu Gln Tyr Glu Ala Arg Glu Arg Pro Asn Thr Lys Ser
    290                 295                 300

Leu Val Thr Ala Leu Thr Pro Leu Gln Lys Glu Thr Glu Val Leu Ser
305                 310                 315                 320

His Val Leu Met Gly Leu Pro His Ser Gly Ser Val Ser Pro Leu Ser
                325                 330                 335

Pro Leu Gly Glu Ala Cys Ser Arg Arg Asp Leu Thr Ala Met Leu Glu
            340                 345                 350

Ile Leu Glu Lys Leu Gly Tyr Lys Asp Asp Glu Gly Val Thr Asn Glu
        355                 360                 365

Leu Ser Phe His Met Trp Thr Asp Gln Met Gln Glu Ser Leu Asn Ser
    370                 375                 380

Lys Lys Lys Gly Asp Val Ala Phe Arg Gln Lys Asp Phe Arg Glu Ala
385                 390                 395                 400

Ile Glu Cys Tyr Thr Gln Phe Ile Asp Gly Gly Met Ile Ser Pro Thr
                405                 410                 415
```

```
Val Cys Ala Arg Arg Ser Leu Cys Tyr Leu Met Ser Asp Met Pro Lys
            420                 425                 430

Glu Ala Leu Asp Asp Ala Ile Gln Ala Gln Val Ile Ser Pro Val Trp
        435                 440                 445

His Val Ala Ser Tyr Leu Gln Ser Ala Ser Leu Gly Ile Leu Gly Met
    450                 455                 460

Glu Lys Glu Ser Gln Ile Ala Leu Lys Glu Gly Ser Asn Leu Glu Ala
465                 470                 475                 480

Lys Met Asn Gly Val Pro Arg Val Lys
                485


<210> SEQ ID NO 7
<211> LENGTH: 1452
<212> TYPE: DNA
<213> ORGANISM: Arabidopsis thaliana

<400> SEQUENCE: 7

atgggaggtc aaagctcaaa gattggtaca tgttgttcac acaagactac tgctcttgaa      60

gctccagatg ttgaaaacaa agagaatggt gaggtaaacg gtgtgcattc ttttcgtgaa     120

tactcactag aacagcttaa gatcgccacc tcttgttttg ctttggagaa tgttgtatct     180

gaacatggag aaacagctcc aaatgttgtc tatcaaggga aattggagaa tcatatgaag     240

attgctatca agcgcttttc tggaactgcc tggcctgatc ctcgccaatt cctggaagaa     300

gcaagattgg ttggtcagct acgcagcaaa agaatggcca atttactcgg ttattgctgt     360

gaaggcggcg agaggttact tgtggctgag tttatgccta atgagacact agccaaacac     420

cttttccact gggatacaga gccaatgaaa tgggcgatgc gactaagggt tgctctatac     480

atttcagaag ctcttgaata ctgtagtaac aatggacaca cgctatatca tgatctcaat     540

gcttacagag ttttatttga cgaggaatgt aatccaagac tttcaacatt tgggttaatg     600

aagaatagtc gggatgggaa aagttatagc acaaatcttg cttttacccc acctgagtat     660

ctacgaactg ggagaatcac agcagagagt gtgatttaca gttttggcac tcttctgctt     720

gatcttctca ccggaaagca tattcctcct agccatgccc ttgatttgat tcgagacaga     780

aatcttcaga ctctaaccga ttcctgcttg gagggacaat tttcagacag tgatggtacg     840

gagttagtac gcctgacatc ttgttgtctt cagtatgaag ctcgtgagcg accaaacata     900

aaatctttgg tcactgcact gatatctctc cagaaagaca cagaggttct gtctcatgtt     960

ctaatgggtc tgcctcaaag tggtactttt gcgtcacctc cgtctccttt tgctgaggct    1020

tgctcgggaa aagacctgac gtctatggtt gagatcttgg aaaaaattgg ttacaaagac    1080

gatgaagatc tttcgtttat gtggacggaa cagatgcaag aagctataaa ctcgaagaaa    1140

aaaggtgata ttgcatttag aagaaaagac tttagtgaag ccattgagtt ttacacgcag    1200

tttcttgatt tgggaatgat ctctgcaaca gtcttggtgc ggcgaagtca aagttaccta    1260

atgagtaaca tggcgaaaga agctttagat gatgcaatga aggctcaagg catttctcct    1320

gtttggtatg ttgcattgta tctccagtct gctgctcttt ctgtcctggg aatggagaag    1380

gaatctcaaa tcgcacttac cgaaggatcc attcttgaag ccagaaagat ttcagcttcc    1440

acacagaact aa                                                        1452


<210> SEQ ID NO 8
<211> LENGTH: 483
<212> TYPE: PRT
<213> ORGANISM: Arabidopsis thaliana

<400> SEQUENCE: 8
```

-continued

```
Met Gly Gly Gln Ser Ser Lys Ile Gly Thr Cys Cys Ser His Lys Thr
1               5                   10                  15

Thr Ala Leu Glu Ala Pro Asp Val Glu Asn Lys Glu Asn Gly Glu Val
            20                  25                  30

Asn Gly Val His Ser Phe Arg Glu Tyr Ser Leu Glu Gln Leu Lys Ile
        35                  40                  45

Ala Thr Ser Cys Phe Ala Leu Glu Asn Val Val Ser Glu His Gly Glu
    50                  55                  60

Thr Ala Pro Asn Val Val Tyr Gln Gly Lys Leu Glu Asn His Met Lys
65                  70                  75                  80

Ile Ala Ile Lys Arg Phe Ser Gly Thr Ala Trp Pro Asp Pro Arg Gln
                85                  90                  95

Phe Leu Glu Glu Ala Arg Leu Val Gly Gln Leu Arg Ser Lys Arg Met
            100                 105                 110

Ala Asn Leu Leu Gly Tyr Cys Cys Glu Gly Gly Glu Arg Leu Leu Val
        115                 120                 125

Ala Glu Phe Met Pro Asn Glu Thr Leu Ala Lys His Leu Phe His Trp
    130                 135                 140

Asp Thr Glu Pro Met Lys Trp Ala Met Arg Leu Arg Val Ala Leu Tyr
145                 150                 155                 160

Ile Ser Glu Ala Leu Glu Tyr Cys Ser Asn Asn Gly His Thr Leu Tyr
                165                 170                 175

His Asp Leu Asn Ala Tyr Arg Val Leu Phe Asp Glu Glu Cys Asn Pro
            180                 185                 190

Arg Leu Ser Thr Phe Gly Leu Met Lys Asn Ser Arg Asp Gly Lys Ser
        195                 200                 205

Tyr Ser Thr Asn Leu Ala Phe Thr Pro Pro Glu Tyr Leu Arg Thr Gly
    210                 215                 220

Arg Ile Thr Ala Glu Ser Val Ile Tyr Ser Phe Gly Thr Leu Leu Leu
225                 230                 235                 240

Asp Leu Leu Thr Gly Lys His Ile Pro Pro Ser His Ala Leu Asp Leu
                245                 250                 255

Ile Arg Asp Arg Asn Leu Gln Thr Leu Thr Asp Ser Cys Leu Glu Gly
            260                 265                 270

Gln Phe Ser Asp Ser Asp Gly Thr Glu Leu Val Arg Leu Thr Ser Cys
        275                 280                 285

Cys Leu Gln Tyr Glu Ala Arg Glu Arg Pro Asn Ile Lys Ser Leu Val
    290                 295                 300

Thr Ala Leu Ile Ser Leu Gln Lys Asp Thr Glu Val Leu Ser His Val
305                 310                 315                 320

Leu Met Gly Leu Pro Gln Ser Gly Thr Phe Ala Ser Pro Pro Ser Pro
                325                 330                 335

Phe Ala Glu Ala Cys Ser Gly Lys Asp Leu Thr Ser Met Val Glu Ile
            340                 345                 350

Leu Glu Lys Ile Gly Tyr Lys Asp Asp Glu Asp Leu Ser Phe Met Trp
        355                 360                 365

Thr Glu Gln Met Gln Glu Ala Ile Asn Ser Lys Lys Lys Gly Asp Ile
    370                 375                 380

Ala Phe Arg Arg Lys Asp Phe Ser Glu Ala Ile Glu Phe Tyr Thr Gln
385                 390                 395                 400

Phe Leu Asp Leu Gly Met Ile Ser Ala Thr Val Leu Val Arg Arg Ser
                405                 410                 415

Gln Ser Tyr Leu Met Ser Asn Met Ala Lys Glu Ala Leu Asp Asp Ala
```

```
            420                 425                 430

Met Lys Ala Gln Gly Ile Ser Pro Val Trp Tyr Val Ala Leu Tyr Leu
        435                 440                 445

Gln Ser Ala Ala Leu Ser Val Leu Gly Met Glu Lys Glu Ser Gln Ile
    450                 455                 460

Ala Leu Thr Glu Gly Ser Ile Leu Glu Ala Arg Lys Ile Ser Ala Ser
465                 470                 475                 480

Thr Gln Asn


<210> SEQ ID NO 9
<211> LENGTH: 1846
<212> TYPE: DNA
<213> ORGANISM: Arabidopsis thaliana

<400> SEQUENCE: 9

cgcagattcc tttctcctcg agaacaaaaa aaacttcttt tttttctct ttctctcttg      60

gcttctcttt agaaagtgac tcaccagaaa aaaaaaaggg tttttgcttt tcgggtttag     120

ctaagaaaaa tctttcaatc ttccttaaat ctttcaaaac cccaaaatgg gacctcgttg     180

ctctaagctc tctctctgtt ggtggccgac ccatctcaaa tcaactcaca acgaagcttc     240

tgatctagat aacggaacgg acgatttgcc gtcgtttacg gagtttagtt tcgaccaact     300

acgagctgct acttgtggat tctctacaga cagtattgtc tccgaacatg gtgttaaagc     360

tcctaatgtt gtgtataaag gcagacttga agatgaccga tggatcgctg ttaaacgatt     420

caatagatcc gcttggcctg atactcgtca atttcttgaa gaagcaaaag ctgtggggca     480

gttgaggaat gagaggttgg cgaatttgat tggattctgt tgtgaaggag acgagagatt     540

gctcgttgct gagtttatgc cttttgaaac tctctcgaag catctctttc actgggatag     600

tcagccaatg aagtggtcta tgaggttgag agtggctttg tatcttgcac aagcacttga     660

gtattgtagc agcaaaggtc gcgccttgta ccacgatctt aatgcttaca ggatcttgtt     720

tgaccaggat ggtaacccga gattatcttg ctttggtctt atgaagaata gtagggatgg     780

gaagagttac agtacaaatt tggctttcac acctcctgaa tacctaagaa cagggagagt     840

gattccggag agtgtggtct acagcttcgg aacgctgttg ctagatcttc tcagcggcaa     900

acacatacca ccaagccatg cgcttgatct gattcgtggg aagaatttcc tgatgctgat     960

ggactcgtgt ctagatggcc atttctcaaa cgatgatgga accgatttgg ttcgtttagc    1020

ttcccgttgt ttgcagtatg aagctcgtga aaggccaaat gtgaaatctc tcgtgtcctc    1080

actcgctcct cttcagaaag aaactgatat tccgtctcat gttttaatgg ggattccaca    1140

tggagctgct tctccaaagg aaacaacttc gcttacccct cttggtgacg cttgttcacg    1200

acatgatctc acagcaatac atgaaattct cgaaaaggtt ggatacaaag atgacgaggg    1260

tgtagcaaat gagctctcgt tccaagtgtg gaccgaccag attcaggaga ctctaaactc    1320

caagaaacaa ggagatgctg cgttcaaagg caaagacttt gtcactgctg ttgaatgtta    1380

cacgcagttc atcgaagatg gcacaatggt atcgccaaca gtttttgcaa ggaggtgttt    1440

gtgttatctg atgagcaata tgcctcaaga ggctcttggt gatgcaatgc aggcgcaagt    1500

agtgtctcct gaatggccaa cggctttcta tcttcaggcc gctgctctct tcagccttgg    1560

aatggataaa gacgcctgtg aaaccctaaa agatggaact tccttggaag ccaagaaaca    1620

taacaacaga aactgaaaac ttcaagtgta taggtttctt ctctcttccg ccttcttcgt    1680

tttgtgattg gattctgaga aagcctcatt gtctctgtct tctttaagca ttatcttaaa    1740

tttgtggttt ccaatttgaa gagatgattc aaatcacatt tgaatcaaga aaagaaggat    1800
```

```
ctttctcatt taagtccaag atccttatat gagatttgtt caaact               1846


<210> SEQ ID NO 10
<211> LENGTH: 489
<212> TYPE: PRT
<213> ORGANISM: Arabidopsis thaliana

<400> SEQUENCE: 10

Met Gly Pro Arg Cys Ser Lys Leu Ser Leu Cys Trp Trp Pro Thr His
1               5                   10                  15

Leu Lys Ser Thr His Asn Glu Ala Ser Asp Leu Asp Asn Gly Thr Asp
            20                  25                  30

Asp Leu Pro Ser Phe Thr Glu Phe Ser Phe Asp Gln Leu Arg Ala Ala
        35                  40                  45

Thr Cys Gly Phe Ser Thr Asp Ser Ile Val Ser Glu His Gly Val Lys
    50                  55                  60

Ala Pro Asn Val Val Tyr Lys Gly Arg Leu Glu Asp Asp Arg Trp Ile
65                  70                  75                  80

Ala Val Lys Arg Phe Asn Arg Ser Ala Trp Pro Asp Thr Arg Gln Phe
                85                  90                  95

Leu Glu Glu Ala Lys Ala Val Gly Gln Leu Arg Asn Glu Arg Leu Ala
            100                 105                 110

Asn Leu Ile Gly Phe Cys Cys Glu Gly Asp Glu Arg Leu Leu Val Ala
        115                 120                 125

Glu Phe Met Pro Phe Glu Thr Leu Ser Lys His Leu Phe His Trp Asp
    130                 135                 140

Ser Gln Pro Met Lys Trp Ser Met Arg Leu Arg Val Ala Leu Tyr Leu
145                 150                 155                 160

Ala Gln Ala Leu Glu Tyr Cys Ser Ser Lys Gly Arg Ala Leu Tyr His
                165                 170                 175

Asp Leu Asn Ala Tyr Arg Ile Leu Phe Asp Gln Asp Gly Asn Pro Arg
            180                 185                 190

Leu Ser Cys Phe Gly Leu Met Lys Asn Ser Arg Asp Gly Lys Ser Tyr
        195                 200                 205

Ser Thr Asn Leu Ala Phe Thr Pro Pro Glu Tyr Leu Arg Thr Gly Arg
    210                 215                 220

Val Ile Pro Glu Ser Val Val Tyr Ser Phe Gly Thr Leu Leu Leu Asp
225                 230                 235                 240

Leu Leu Ser Gly Lys His Ile Pro Pro Ser His Ala Leu Asp Leu Ile
                245                 250                 255

Arg Gly Lys Asn Phe Leu Met Leu Met Asp Ser Cys Leu Asp Gly His
            260                 265                 270

Phe Ser Asn Asp Asp Gly Thr Asp Leu Val Arg Leu Ala Ser Arg Cys
        275                 280                 285

Leu Gln Tyr Glu Ala Arg Glu Arg Pro Asn Val Lys Ser Leu Val Ser
    290                 295                 300

Ser Leu Ala Pro Leu Gln Lys Glu Thr Asp Ile Pro Ser His Val Leu
305                 310                 315                 320

Met Gly Ile Pro His Gly Ala Ala Ser Pro Lys Glu Thr Thr Ser Leu
                325                 330                 335

Thr Pro Leu Gly Asp Ala Cys Ser Arg His Asp Leu Thr Ala Ile His
            340                 345                 350

Glu Ile Leu Glu Lys Val Gly Tyr Lys Asp Asp Glu Gly Val Ala Asn
        355                 360                 365
```

```
Glu Leu Ser Phe Gln Val Trp Thr Asp Gln Ile Gln Glu Thr Leu Asn
    370                 375                 380

Ser Lys Lys Gln Gly Asp Ala Ala Phe Lys Gly Lys Asp Phe Val Thr
385                 390                 395                 400

Ala Val Glu Cys Tyr Thr Gln Phe Ile Glu Asp Gly Thr Met Val Ser
                405                 410                 415

Pro Thr Val Phe Ala Arg Arg Cys Leu Cys Tyr Leu Met Ser Asn Met
            420                 425                 430

Pro Gln Glu Ala Leu Gly Asp Ala Met Gln Ala Gln Val Val Ser Pro
        435                 440                 445

Glu Trp Pro Thr Ala Phe Tyr Leu Gln Ala Ala Ala Leu Phe Ser Leu
    450                 455                 460

Gly Met Asp Lys Asp Ala Cys Glu Thr Leu Lys Asp Gly Thr Ser Leu
465                 470                 475                 480

Glu Ala Lys Lys His Asn Asn Arg Asn
                485


<210> SEQ ID NO 11
<211> LENGTH: 1911
<212> TYPE: DNA
<213> ORGANISM: Arabidopsis thaliana

<400> SEQUENCE: 11

aatattaatt tagaaaagaa aaaaacaatt ctctttgtag agggaagtct gaaaacgccg      60

agaagaagac gaagaagaag aagaagaaga aagcttgaga ctttctctct gtgtgcaatt     120

tcgaaatcga taaagacttc aactttcggt tctaacaatg acaatttccg tatagtttga     180

ttttgtccac ctctttcacc gattacctga tttcatcgct ggcgttagtc atcaaatggg     240

agctcgttgc tcaaagttct cattctgctt gttcccttct cacttcaaat ccgcttcagt     300

tctcgagtct cctgatatcg agaatggagg aaaagtgtgg ccgactttta aggaattcaa     360

attggagcag ctgaaatctg cgaccggagg tttctcttca gacaacattg tatcagaaca     420

cggcgagaaa gctccaaacg ttgtctacag aggaaggctt gatgatggtc gtttgattgc     480

tgtcaaacga ttcaatcgcc ttgcttgggc tgatcatcga cagttcctgg atgaagctaa     540

agctgttggg agcttgagga gtgatagatt agcgaatctg attggatgtt gctttgaagg     600

agaagagaga ttactagttg ctgagtttat gcctcatgaa acgcttgcaa agcatctttt     660

ccactgggag aataatccga tgaaatgggc gatgagatta agagttgcat tgtgtttagc     720

acaagcattg gaatattgta gtaataaagg gagagctttg tatcatgatc tcaatgctta     780

cagggttttg tttgacaagg atgggaatcc caggttgtct tgttttggac tcatgaaaaa     840

tagcagagat gggaagagtt atagcacaaa cttggcattt actcctccag agtatttgcg     900

aacgggtaga gttacaccag agagtgttgt attcagtttt ggaaccgttt tgctcgatct     960

catgagtgga aaacatattc caccgagtca tgcgcttgac ctaatcagag gcaagaactg    1020

tgcaatgtta atggattctg ctctcgaggg tcatttctca aacgaagacg gaactgagct    1080

agtacgctta gccacacgtt gtctgcagta tgaagctcga gaaagaccaa atgtgaaatc    1140

tctcgtgact tcacttgtca cactccagaa ggaatctgat gtagcttcct acgttcttat    1200

gggtataccc catgaaaccg aggctgaaga agagtctccg ctttctttga cacccctttgg    1260

tgatgcatgc ttaagagtgg atcttacagc catacaggaa atactcagta agattggata    1320

caaggatgat gaaggaattg ccaatgagct ctcgtttcaa atgtggacca atcagatgca    1380

ggaatctctc aattcgaaga agcaaggcga cttagctttc cgttccaaag atttacaac    1440
```

```
cgcggtcgat tgctacactc agttcataga tgggggaaca atggtgtcac caacagtaca   1500

cgcacggcgg tgcttgtcat atctgatgaa cgacaacgca caagaggctc tgacagatgc   1560

attgcaggca caggttgtgt ctccggattg gccaaccgcc ttgtatctgc aagcggcttg   1620

cttgttcaag ctgggtatgg aagccgatgc tcagcaagct cttaaggatg ggactacatt   1680

ggaagctaag aagagtaaca agcgctgata aaatagcgtt ttcaaaagct tttgtatatg   1740

ctttattttg tttcctttct ctctatttcc atctatatgc gcatacatac acatatgcgg   1800

gtgtatttat tatatatgtg catatacttt tgatgccttg tttgttgtat ttattttta   1860

gtatgcctca tgggaagatc tcttttatta ttattgaaat cataagtgat g            1911
```

<210> SEQ ID NO 12
<211> LENGTH: 490
<212> TYPE: PRT
<213> ORGANISM: Arabidopsis thaliana

<400> SEQUENCE: 12

```
Met Gly Ala Arg Cys Ser Lys Phe Ser Phe Cys Leu Phe Pro Ser His
1               5                   10                  15

Phe Lys Ser Ala Ser Val Leu Glu Ser Pro Asp Ile Glu Asn Gly Gly
            20                  25                  30

Lys Val Trp Pro Thr Phe Lys Glu Phe Lys Leu Glu Gln Leu Lys Ser
        35                  40                  45

Ala Thr Gly Gly Phe Ser Ser Asp Asn Ile Val Ser Glu His Gly Glu
    50                  55                  60

Lys Ala Pro Asn Val Val Tyr Arg Gly Arg Leu Asp Asp Gly Arg Leu
65                  70                  75                  80

Ile Ala Val Lys Arg Phe Asn Arg Leu Ala Trp Ala Asp His Arg Gln
                85                  90                  95

Phe Leu Asp Glu Ala Lys Ala Val Gly Ser Leu Arg Ser Asp Arg Leu
            100                 105                 110

Ala Asn Leu Ile Gly Cys Cys Phe Glu Gly Glu Glu Arg Leu Leu Val
        115                 120                 125

Ala Glu Phe Met Pro His Glu Thr Leu Ala Lys His Leu Phe His Trp
    130                 135                 140

Glu Asn Asn Pro Met Lys Trp Ala Met Arg Leu Arg Val Ala Leu Cys
145                 150                 155                 160

Leu Ala Gln Ala Leu Glu Tyr Cys Ser Asn Lys Gly Arg Ala Leu Tyr
                165                 170                 175

His Asp Leu Asn Ala Tyr Arg Val Leu Phe Asp Lys Asp Gly Asn Pro
            180                 185                 190

Arg Leu Ser Cys Phe Gly Leu Met Lys Asn Ser Arg Asp Gly Lys Ser
        195                 200                 205

Tyr Ser Thr Asn Leu Ala Phe Thr Pro Pro Glu Tyr Leu Arg Thr Gly
    210                 215                 220

Arg Val Thr Pro Glu Ser Val Val Phe Ser Phe Gly Thr Val Leu Leu
225                 230                 235                 240

Asp Leu Met Ser Gly Lys His Ile Pro Pro Ser His Ala Leu Asp Leu
                245                 250                 255

Ile Arg Gly Lys Asn Cys Ala Met Leu Met Asp Ser Ala Leu Glu Gly
            260                 265                 270

His Phe Ser Asn Glu Asp Gly Thr Glu Leu Val Arg Leu Ala Thr Arg
        275                 280                 285

Cys Leu Gln Tyr Glu Ala Arg Glu Arg Pro Asn Val Lys Ser Leu Val
    290                 295                 300
```

```
Thr Ser Leu Val Thr Leu Gln Lys Glu Ser Asp Val Ala Ser Tyr Val
305                 310                 315                 320

Leu Met Gly Ile Pro His Glu Thr Glu Ala Glu Glu Glu Ser Pro Leu
                325                 330                 335

Ser Leu Thr Pro Phe Gly Asp Ala Cys Leu Arg Val Asp Leu Thr Ala
            340                 345                 350

Ile Gln Glu Ile Leu Ser Lys Ile Gly Tyr Lys Asp Asp Glu Gly Ile
        355                 360                 365

Ala Asn Glu Leu Ser Phe Gln Met Trp Thr Asn Gln Met Gln Glu Ser
    370                 375                 380

Leu Asn Ser Lys Lys Gln Gly Asp Leu Ala Phe Arg Ser Lys Asp Phe
385                 390                 395                 400

Thr Thr Ala Val Asp Cys Tyr Thr Gln Phe Ile Asp Gly Gly Thr Met
                405                 410                 415

Val Ser Pro Thr Val His Ala Arg Arg Cys Leu Ser Tyr Leu Met Asn
            420                 425                 430

Asp Asn Ala Gln Glu Ala Leu Thr Asp Ala Leu Gln Ala Gln Val Val
        435                 440                 445

Ser Pro Asp Trp Pro Thr Ala Leu Tyr Leu Gln Ala Ala Cys Leu Phe
    450                 455                 460

Lys Leu Gly Met Glu Ala Asp Ala Gln Gln Ala Leu Lys Asp Gly Thr
465                 470                 475                 480

Thr Leu Glu Ala Lys Lys Ser Asn Lys Arg
                485                 490
```

<210> SEQ ID NO 13
<211> LENGTH: 2160
<212> TYPE: DNA
<213> ORGANISM: Arabidopsis thaliana

<400> SEQUENCE: 13

```
cctctgttct ttgagctttc cctttgagct ctcacacgag cggcttcttt tgtcatctca     60

ccttttcctt cattctttct tccttcaaat tctggttttt ttcacagatc gttttctcag    120

attttgactc tttttggtgt tgttgttgtt cttctccttc gtgaagtgga agaagaatat    180

aacaaaactg ggttttttat atctggaatt ctgaagaaat tcttcacgga tttgatctgt    240

ttaaactata aaagtcttga tttttataaa tcagctaaaa ataagacacg gtttagggtt    300

tatggtttga ctagaaacaa caatactgaa atgggttgtg aggtttcaaa gttatgtgca    360

ttttgttgtg tttctgatcc tgaaggatct aatcatggtg tcacagggtt agatgaagat    420

aggagaggtg aagggaatga tttgcctcag tttcgtgaat tctcaattga gacgttgagg    480

aacgcaacat caggatttgc tacagagaat atagtatcag agcatggtga aaaagctcca    540

aatgttgtgt ataaagggaa attggataat caaagacgta ttgctgttaa aaggtttaat    600

aggaaagctt ggcctgattc tcgtcagttt ctggaggaag ctaaagctgt tggtcaatta    660

aggaattata gaatggcaaa tcttcttgga tgttgttatg aaggtgaaga gagacttctt    720

gttgctgagt ttatgcctaa tgaaactttg gctaagcatc ttttccattg ggagtcacaa    780

ccgatgaagt gggcgatgcg actaagagta gctttacata ttgctcaagc tttagaatat    840

tgtactggca aaggacgtgc actctaccat gacttaaatg cttatagagt tctctttgat    900

gatgactcaa atccaagact ttcatgcttc ggtctgatga aaaatagtag agacggaaag    960

agttatagca ccaacctggc gttcactcct ccagagtatc tcagaacagg tcgtgtgaca   1020

ccagaaagtg tgatgtacag ttatggaact ctgttgcttg atcttcttag tggaaaacac   1080
```

```
attcctccaa gtcatgctct ggacctcata cgggacagga acattcaaat gttgatcgac   1140

tcatgcttgg agggtcaatt ttcaagcgac gacgggactg aactaatacg gttagcttct   1200

agatgcttgc agtatgagcc ccgggagcgg cctaacccga agtctttagt tactgcaatg   1260

atccctctac agaaggatct tgagactcct tctcatcaac tgatgggcat accaagcagc   1320

gcctcaacga cacccctttc accacttgga gaagcatgcc taagaacaga tctaactgcc   1380

atacatgaga ttcttgaaaa gcttagctat aaagatgacg agggtgcagc aacagagctt   1440

tcgttccaga tgtggaccaa tcagatgcag gactcgctga acttcaagaa gaagggtgat   1500

gttgctttcc gacataaaga atttgcaaat gccatcgact gctattctca gttcattgag   1560

ggtgggacaa tggtttcccc gactgtttat gcaagaagaa gtctgtgtta cctaatgaat   1620

gagatgcccc aagaggcgct gaatgatgca atgcaagccc aagtgatatc tccggcttgg   1680

catatcgcat cgtatcttca agctgtagct ctatcagctc taggacaaga gaacgaagca   1740

cacgctgctc ttaaagacgg atcaatgctt gaaagcaaaa gaaacaggct atgatgatga   1800

taccagaaaa cacgaagagg aaaatgagag aggaaagcta aagaccattt atcttcttac   1860

attaaaccga aacgccccca taggggcttt gtaggataag ttcaaatctc atcctctgaa   1920

gtagaagcta ctacagagtt ctcctatcgt gttcatcatc atcatcatca ctggtcagtt   1980

tcgggttccg ctcgtgtata ccctttcctt ctcttttatt tcttattgga agcattcatt   2040

tggtctacta ccgcgaatta gactcttttt atgttcttgg ttactggcat gaacatttcc   2100

ctgctataca gaagaagaaa aaagtttcat aatttgatgg agatttgatt aaagaaaaaa   2160


<210> SEQ ID NO 14
<211> LENGTH: 487
<212> TYPE: PRT
<213> ORGANISM: Arabidopsis thaliana

<400> SEQUENCE: 14

Met Gly Cys Glu Val Ser Lys Leu Cys Ala Phe Cys Cys Val Ser Asp
1               5                   10                  15

Pro Glu Gly Ser Asn His Gly Val Thr Gly Leu Asp Glu Asp Arg Arg
            20                  25                  30

Gly Glu Gly Asn Asp Leu Pro Gln Phe Arg Glu Phe Ser Ile Glu Thr
        35                  40                  45

Leu Arg Asn Ala Thr Ser Gly Phe Ala Thr Glu Asn Ile Val Ser Glu
    50                  55                  60

His Gly Glu Lys Ala Pro Asn Val Val Tyr Lys Gly Lys Leu Asp Asn
65                  70                  75                  80

Gln Arg Arg Ile Ala Val Lys Arg Phe Asn Arg Lys Ala Trp Pro Asp
                85                  90                  95

Ser Arg Gln Phe Leu Glu Glu Ala Lys Ala Val Gly Gln Leu Arg Asn
            100                 105                 110

Tyr Arg Met Ala Asn Leu Leu Gly Cys Cys Tyr Glu Gly Glu Glu Arg
        115                 120                 125

Leu Leu Val Ala Glu Phe Met Pro Asn Glu Thr Leu Ala Lys His Leu
    130                 135                 140

Phe His Trp Glu Ser Gln Pro Met Lys Trp Ala Met Arg Leu Arg Val
145                 150                 155                 160

Ala Leu His Ile Ala Gln Ala Leu Glu Tyr Cys Thr Gly Lys Gly Arg
                165                 170                 175

Ala Leu Tyr His Asp Leu Asn Ala Tyr Arg Val Leu Phe Asp Asp Asp
            180                 185                 190
```

```
Ser Asn Pro Arg Leu Ser Cys Phe Gly Leu Met Lys Asn Ser Arg Asp
        195                 200                 205

Gly Lys Ser Tyr Ser Thr Asn Leu Ala Phe Thr Pro Pro Glu Tyr Leu
    210                 215                 220

Arg Thr Gly Arg Val Thr Pro Glu Ser Val Met Tyr Ser Tyr Gly Thr
225                 230                 235                 240

Leu Leu Leu Asp Leu Leu Ser Gly Lys His Ile Pro Pro Ser His Ala
                245                 250                 255

Leu Asp Leu Ile Arg Asp Arg Asn Ile Gln Met Leu Ile Asp Ser Cys
            260                 265                 270

Leu Glu Gly Gln Phe Ser Ser Asp Asp Gly Thr Glu Leu Ile Arg Leu
        275                 280                 285

Ala Ser Arg Cys Leu Gln Tyr Glu Pro Arg Glu Arg Pro Asn Pro Lys
    290                 295                 300

Ser Leu Val Thr Ala Met Ile Pro Leu Gln Lys Asp Leu Glu Thr Pro
305                 310                 315                 320

Ser His Gln Leu Met Gly Ile Pro Ser Ser Ala Ser Thr Thr Pro Leu
                325                 330                 335

Ser Pro Leu Gly Glu Ala Cys Leu Arg Thr Asp Leu Thr Ala Ile His
            340                 345                 350

Glu Ile Leu Glu Lys Leu Ser Tyr Lys Asp Asp Glu Gly Ala Ala Thr
        355                 360                 365

Glu Leu Ser Phe Gln Met Trp Thr Asn Gln Met Gln Asp Ser Leu Asn
    370                 375                 380

Phe Lys Lys Lys Gly Asp Val Ala Phe Arg His Lys Glu Phe Ala Asn
385                 390                 395                 400

Ala Ile Asp Cys Tyr Ser Gln Phe Ile Glu Gly Gly Thr Met Val Ser
                405                 410                 415

Pro Thr Val Tyr Ala Arg Arg Ser Leu Cys Tyr Leu Met Asn Glu Met
            420                 425                 430

Pro Gln Glu Ala Leu Asn Asp Ala Met Gln Ala Gln Val Ile Ser Pro
        435                 440                 445

Ala Trp His Ile Ala Ser Tyr Leu Gln Ala Val Ala Leu Ser Ala Leu
    450                 455                 460

Gly Gln Glu Asn Glu Ala His Ala Ala Leu Lys Asp Gly Ser Met Leu
465                 470                 475                 480

Glu Ser Lys Arg Asn Arg Leu
                485
```

<210> SEQ ID NO 15
<211> LENGTH: 2192
<212> TYPE: DNA
<213> ORGANISM: Arabidopsis thaliana

<400> SEQUENCE: 15

```
tcaaagctca cacacacgac cactctattc ctcctttaac ctttgtgttt gtcaatttgt     60

gtttcctctt ttgtcgactc atttctcgat tcaatctcga ttttttttt ttttttttt    120

atggaaatct aatgaacttt ttttatggat ttgatctgtt aaagtttcga ttaagaagat    180

agtggtttag gtttacggtt ttgtaattga tttattatct gtaatgggtt gtgaggtttc    240

aaagttatct gcactttgtt gtgtttcaga gtctggaaga tcgaatcctg atgttacagg    300

cttagatgag gaagggagag gtgaatcgaa tgatttgcct caatttcgtg agttctctat    360

agagactata aggaacgcaa cttcaggatt tgcagcagag aatatagttt cagagcatgg    420
```

```
tgagagagct cctaatgttg tctataaagg caagcttgag aatcaaagac gtattgctgt    480
caaaaggttt aaccggaaat cttggcctga ttctcgtcaa ttcttggaag aagccaaagc    540
tgttggtcaa ttacggaatc ataggatggc aaatctactt gggtgttgtt atgaagatga    600
agagagacta cttattgcag agtttatgcc taatgaaact ttggcaaaac atcttttcca    660
ctgggagtca cagccaatga agtgggcgat gcgactgaga gtagctttgc atattgctca    720
ggcgctagag tattgtacca gcaaaggacg tgcactttac catgacctaa atgcttatag    780
agttctcttt gatgatgatg caaatccaag actttcatgc tttggtttga tgaaaaacag    840
tagagatgga aagagttata gcactaacct ggcattcact cctcccgagt atctgaggac    900
aggtcgcgtg acacctgaaa gtgtaatata cagctttgga actctattac ttgaccttct    960
gagtggaaag catatacctc caagccatgc gttggacctc atacgggaca ggaacattca   1020
gatgctgatg gattcaggtt tggaaggtca attttcgagt gacgatggaa ctgaattaat   1080
aaggttagct tcaagatgct tgcaatatga accccgagag cggcctaacc caaaatcttt   1140
agtctctgca atgattcctc ttcagaaaga tcttgagatt gcttctcatc aattgttggg   1200
cgtacctaac agtgccacaa cgacagctct ttcacctctt ggcgaagcat gcctaagatc   1260
agatctaact gccatacatg agatcattga gaagcttgga tataaggatg acgagggtgc   1320
aaccacagag ctttctttcc agatgtggac cgaccagatg caggacacat tggtcttcaa   1380
gaaaaagggg gattctgcat tccgacataa agactttgca aaggccatcg aatgctattc   1440
tcagttcatc gaggtaggta caatgggttc cccaactgtt catgcaagac agagtctgtg   1500
ttacctaatg aatgatatgc ctagagaagc actaaacaat gcaatgcaag cacaagtcat   1560
atctcctgct tggcatatcg catcgtatct ccaagctgta gctttgtcag ctctaggaca   1620
agagaacgaa gcacacactg ctctaaaaga cggtgcaatg cttgaaagca aaagaaaccc   1680
tttgtgatta taagcaacac aaagaggaga aactggagta caagagaaat ataaccatcc   1740
tttacgctaa cccatacacc cgaagaacca ctgtcgcaac attgtattta agatcaaagc   1800
ataacaagtc tacagcgatt gttcctttcc gaagccttga tcatcacatc acattactgg   1860
ttagtctggt ttttatttca gtttagtgct ccattttgca agatccgcgg ttcaagccac   1920
tgtgattatt cgattacagc gagtggactg tgtttattgt tgttgtttaa gttcaatggt   1980
gcagacgtgt ttcgtatcat agagaagaaa agaagtgtct atggagatat gatgacaaaa   2040
cttaaaaatg tatgattgtg acattgtgta ttattcgctt taatgtaatt caatgtttgt   2100
attattgtat agaatgaagt atgaacctct ctctgctata atgttattcc cctccttttt   2160
tttcttgaat tttgcaaatg ttgaaacgct ta                                 2192
```

```
<210> SEQ ID NO 16
<211> LENGTH: 487
<212> TYPE: PRT
<213> ORGANISM: Arabidopsis thaliana

<400> SEQUENCE: 16

Met Gly Cys Glu Val Ser Lys Leu Ser Ala Leu Cys Cys Val Ser Glu
1               5                   10                  15

Ser Gly Arg Ser Asn Pro Asp Val Thr Gly Leu Asp Glu Glu Gly Arg
            20                  25                  30

Gly Glu Ser Asn Asp Leu Pro Gln Phe Arg Glu Phe Ser Ile Glu Thr
        35                  40                  45

Ile Arg Asn Ala Thr Ser Gly Phe Ala Ala Glu Asn Ile Val Ser Glu
    50                  55                  60
```

```
His Gly Glu Arg Ala Pro Asn Val Val Tyr Lys Gly Lys Leu Glu Asn
65                  70                  75                  80

Gln Arg Arg Ile Ala Val Lys Arg Phe Asn Arg Lys Ser Trp Pro Asp
                85                  90                  95

Ser Arg Gln Phe Leu Glu Glu Ala Lys Ala Val Gly Gln Leu Arg Asn
            100                 105                 110

His Arg Met Ala Asn Leu Leu Gly Cys Cys Tyr Glu Asp Glu Glu Arg
        115                 120                 125

Leu Leu Ile Ala Glu Phe Met Pro Asn Glu Thr Leu Ala Lys His Leu
    130                 135                 140

Phe His Trp Glu Ser Gln Pro Met Lys Trp Ala Met Arg Leu Arg Val
145                 150                 155                 160

Ala Leu His Ile Ala Gln Ala Leu Glu Tyr Cys Thr Ser Lys Gly Arg
                165                 170                 175

Ala Leu Tyr His Asp Leu Asn Ala Tyr Arg Val Leu Phe Asp Asp Asp
            180                 185                 190

Ala Asn Pro Arg Leu Ser Cys Phe Gly Leu Met Lys Asn Ser Arg Asp
        195                 200                 205

Gly Lys Ser Tyr Ser Thr Asn Leu Ala Phe Thr Pro Pro Glu Tyr Leu
    210                 215                 220

Arg Thr Gly Arg Val Thr Pro Glu Ser Val Ile Tyr Ser Phe Gly Thr
225                 230                 235                 240

Leu Leu Leu Asp Leu Leu Ser Gly Lys His Ile Pro Pro Ser His Ala
                245                 250                 255

Leu Asp Leu Ile Arg Asp Arg Asn Ile Gln Met Leu Met Asp Ser Gly
            260                 265                 270

Leu Glu Gly Gln Phe Ser Ser Asp Asp Gly Thr Glu Leu Ile Arg Leu
        275                 280                 285

Ala Ser Arg Cys Leu Gln Tyr Glu Pro Arg Glu Arg Pro Asn Pro Lys
    290                 295                 300

Ser Leu Val Ser Ala Met Ile Pro Leu Gln Lys Asp Leu Glu Ile Ala
305                 310                 315                 320

Ser His Gln Leu Leu Gly Val Pro Asn Ser Ala Thr Thr Thr Ala Leu
                325                 330                 335

Ser Pro Leu Gly Glu Ala Cys Leu Arg Ser Asp Leu Thr Ala Ile His
            340                 345                 350

Glu Ile Ile Glu Lys Leu Gly Tyr Lys Asp Asp Glu Gly Ala Thr Thr
        355                 360                 365

Glu Leu Ser Phe Gln Met Trp Thr Asp Gln Met Gln Asp Thr Leu Val
    370                 375                 380

Phe Lys Lys Lys Gly Asp Ser Ala Phe Arg His Lys Asp Phe Ala Lys
385                 390                 395                 400

Ala Ile Glu Cys Tyr Ser Gln Phe Ile Glu Val Gly Thr Met Gly Ser
                405                 410                 415

Pro Thr Val His Ala Arg Gln Ser Leu Cys Tyr Leu Met Asn Asp Met
            420                 425                 430

Pro Arg Glu Ala Leu Asn Asn Ala Met Gln Ala Gln Val Ile Ser Pro
        435                 440                 445

Ala Trp His Ile Ala Ser Tyr Leu Gln Ala Val Ala Leu Ser Ala Leu
    450                 455                 460

Gly Gln Glu Asn Glu Ala His Thr Ala Leu Lys Asp Gly Ala Met Leu
465                 470                 475                 480

Glu Ser Lys Arg Asn Pro Leu
                485
```

<210> SEQ ID NO 17
<211> LENGTH: 1434
<212> TYPE: DNA
<213> ORGANISM: Arabidopsis thaliana

<400> SEQUENCE: 17

```
atgatcgaga gaactaacct aatagttttg gctgcagata ataaagaaga agatgaagga      60

agtacttgtc ctaatttcct ggagttcagc ttggaacagt tgagagtcgc aactgacgga     120

ttctccgccg acaacatcgt gtcggagcac aacgagaggg ttcctaacat cgtctacaaa     180

ggccagctca acgacggaag aaagatcgcc gtcaagcggt ttcaacggct ttcatggcct     240

gattctttag aattcatcga ggaagcacaa gctgtaggga gatgtaggag tgagcatatg     300

gccaatttga tcggttgttg ctcagaaggt cacgagaggt tgcttgttgc tgagtacatg     360

cctaatgaaa cacttgctaa gcatctcttt cactgggaga aaagaccaat gaagtgggaa     420

atgaggttga gagttgcgtt acatactgca acagccttgg agtactgtaa tgattgggga     480

atagatttgt atcacgatct taacacctac agaatattgt ttgacaaggt tgggaatcct     540

aggctgtctt gttttggtct catgaagtgt agccgagagg gaaagagcta tagtaccaac     600

ttggcatttg ctcctcctga atatttacgt ctaggtactg tgataccgga gagtgtcaca     660

tttagcttcg gaaccttgtt actggatctt atgagcggca gacatattcc accaaaccat     720

gcacttgatc tgttccgtgg taaaaactat ttggtgctaa tggattcagc tctggatggt     780

caattctctg atgaggatag aacagaactt atccatctag cttcccgctg tttgcgccct     840

gaaccagacg agaggccaag cataaagttt cttatgtcag ctctttcaag acttgagaaa     900

agagctgagt tatggcccaa cgtcaaagaa gaaaacatcc ctactccatc atacactgaa     960

cctgcaacaa aggagccatt gcccttgacc cctttcggag aagcatgctg gagagtggat    1020

ctaagtggta tgcacgaact actcgagaaa ctcgggtatg gagaggatga tgtggtggtc    1080

acaaatgagt tctcattcca aatgtggacg ggtcaaatgc aagagaatat ggattacaag    1140

aagcacggag atgccgcatt tcgtgctaaa gattttgaaa ccgcaatcga attctacaca    1200

gagttcatga gtggagcacc agtggtatca ccaacagtat tagccagacg gtgtctatgt    1260

tacctaatga gtgatatgtt ccgcgaggct ctaagtgatg cgatgcaaac tcaggtcgca    1320

tcgccagagt tttcgatcgc tctctactta caagcagctt gtcttttaaa gcttgggatg    1380

gaggctgaag ctaaagaagc tcttagacat ggctcttctc tcgaagcttt ttag          1434
```

<210> SEQ ID NO 18
<211> LENGTH: 477
<212> TYPE: PRT
<213> ORGANISM: Arabidopsis thaliana

<400> SEQUENCE: 18

```
Met Ile Glu Arg Thr Asn Leu Ile Val Leu Ala Ala Asp Asn Lys Glu
1               5                   10                  15

Glu Asp Glu Gly Ser Thr Cys Pro Asn Phe Leu Glu Phe Ser Leu Glu
            20                  25                  30

Gln Leu Arg Val Ala Thr Asp Gly Phe Ser Ala Asp Asn Ile Val Ser
        35                  40                  45

Glu His Asn Glu Arg Val Pro Asn Ile Val Tyr Lys Gly Gln Leu Asn
    50                  55                  60

Asp Gly Arg Lys Ile Ala Val Lys Arg Phe Gln Arg Leu Ser Trp Pro
65                  70                  75                  80
```

```
Asp Ser Leu Glu Phe Ile Glu Glu Ala Gln Ala Val Gly Arg Cys Arg
                85                  90                  95

Ser Glu His Met Ala Asn Leu Ile Gly Cys Cys Ser Glu Gly His Glu
            100                 105                 110

Arg Leu Leu Val Ala Glu Tyr Met Pro Asn Glu Thr Leu Ala Lys His
        115                 120                 125

Leu Phe His Trp Glu Lys Arg Pro Met Lys Trp Glu Met Arg Leu Arg
    130                 135                 140

Val Ala Leu His Thr Ala Thr Ala Leu Glu Tyr Cys Asn Asp Trp Gly
145                 150                 155                 160

Ile Asp Leu Tyr His Asp Leu Asn Thr Tyr Arg Ile Leu Phe Asp Lys
                165                 170                 175

Val Gly Asn Pro Arg Leu Ser Cys Phe Gly Leu Met Lys Cys Ser Arg
            180                 185                 190

Glu Gly Lys Ser Tyr Ser Thr Asn Leu Ala Phe Ala Pro Pro Glu Tyr
        195                 200                 205

Leu Arg Leu Gly Thr Val Ile Pro Glu Ser Val Thr Phe Ser Phe Gly
    210                 215                 220

Thr Leu Leu Leu Asp Leu Met Ser Gly Arg His Ile Pro Pro Asn His
225                 230                 235                 240

Ala Leu Asp Leu Phe Arg Gly Lys Asn Tyr Leu Val Leu Met Asp Ser
                245                 250                 255

Ala Leu Asp Gly Gln Phe Ser Asp Glu Asp Arg Thr Glu Leu Ile His
            260                 265                 270

Leu Ala Ser Arg Cys Leu Arg Pro Glu Pro Asp Glu Arg Pro Ser Ile
        275                 280                 285

Lys Phe Leu Met Ser Ala Leu Ser Arg Leu Glu Lys Arg Ala Glu Leu
    290                 295                 300

Trp Pro Asn Val Lys Glu Glu Asn Ile Pro Thr Pro Ser Tyr Thr Glu
305                 310                 315                 320

Pro Ala Thr Lys Glu Pro Leu Pro Leu Thr Pro Phe Gly Glu Ala Cys
                325                 330                 335

Trp Arg Val Asp Leu Ser Gly Met His Glu Leu Leu Glu Lys Leu Gly
            340                 345                 350

Tyr Gly Glu Asp Asp Val Val Val Thr Asn Glu Phe Ser Phe Gln Met
        355                 360                 365

Trp Thr Gly Gln Met Gln Glu Asn Met Asp Tyr Lys Lys His Gly Asp
    370                 375                 380

Ala Ala Phe Arg Ala Lys Asp Phe Glu Thr Ala Ile Glu Phe Tyr Thr
385                 390                 395                 400

Glu Phe Met Ser Gly Ala Pro Val Val Ser Pro Thr Val Leu Ala Arg
                405                 410                 415

Arg Cys Leu Cys Tyr Leu Met Ser Asp Met Phe Arg Glu Ala Leu Ser
            420                 425                 430

Asp Ala Met Gln Thr Gln Val Ala Ser Pro Glu Phe Ser Ile Ala Leu
        435                 440                 445

Tyr Leu Gln Ala Ala Cys Leu Leu Lys Leu Gly Met Glu Ala Glu Ala
    450                 455                 460

Lys Glu Ala Leu Arg His Gly Ser Ser Leu Glu Ala Phe
465                 470                 475
```

<210> SEQ ID NO 19
<211> LENGTH: 1500
<212> TYPE: DNA
<213> ORGANISM: Arabidopsis thaliana

<400> SEQUENCE: 19

```
atgggatgca tttgcttcaa gtcttggcgc cgatcatctt cttcaccgtc gattacgtca     60
acggtcatag atgatctcga aaacgtcaga gagtacgatg ccgacgacga cggaggacat    120
tatccgttga ttttccgtga gttcagttta gaacagctga gaatcgccac cgacggtttc    180
tccgccggaa acatcgtatc ggagcacaac gattcggtac caaacatcgt ctacaaagga    240
aaactcggcg atggtcgtcg catcgccgtc aaacggtttc aaagactttc ttggcctgat    300
cctttcgaat tcatcaatga agcacaagct gttgggagat tgaggagtga acatatggcg    360
aatttgatcg gttgttgttg tgatgacaac gagagattac ttgttgctga gtatatgcct    420
aatggaacat tagcaaaaca tctttttcac tgggagaaaa gacccatgaa atgggaaatg    480
aggttgaaag ttgctctgca tactgcaaga gctttggagt attgtaatga taaaggaatt    540
gatttatacc atgatcttaa tccttacagg attatgtttg ataagacagg gattcctaag    600
ctttcttgct ttggtctcat gaagaatagc catgaaggga agatttatag caccaactta    660
gcttttgctc ctcccgagta tttgcgcctt ggtactgtga tagcggagag cgtcacattt    720
agctttggaa ccttgttatt ggatcttatg agcggcagac atattcctcc aaaccatgca    780
cttgatttgt tccgtggcaa aaactatttg gtgctaatgg attcagctct tgatggtcag    840
ttctctgatg aagacaggac agaactaata cacgtagctt ctcgatgttt caagactgaa    900
ccagaagaga ggccaagtat aaagtttctt aaggcgactc tttctagact tcagaaacgg    960
gccaagttgt gccctattaa tgtcaaaaga cctatgtctc ctccatcaaa aaatctgcct   1020
gaaaagacta aacctgcaac agagtcattg aagttgactc ctttcggaga tgcatgttct   1080
agagcggatc taagtagtat acatgaacta ctagagaaac tagggtatga agaagataat   1140
ggggttggta acgagttttc attccaaatg tggaccggcg aaatgcaaga gaatatggac   1200
tacaagaagc atggagatgc cgcgtttctt gcgaaagatt ttgatactgc cattgaattc   1260
tacacagagt tcatgactgg agctcctacg gtatcaccaa cagtattggc aagaaggtgt   1320
ctttgttacc taatgactga aatgttcagc gaggctctaa gcgatgcgat gcaagcgcaa   1380
gtagcttcac cggaatggcc aattcctctt tacttacaag cggcttgtct cttcaagcta   1440
gagatggaag ctgaagctaa agaagcactt agacatggtt ctgctcttga ggcttattag   1500
```

<210> SEQ ID NO 20
<211> LENGTH: 499
<212> TYPE: PRT
<213> ORGANISM: Arabidopsis thaliana

<400> SEQUENCE: 20

```
Met Gly Cys Ile Cys Phe Lys Ser Trp Arg Arg Ser Ser Ser Ser Pro
1               5                   10                  15

Ser Ile Thr Ser Thr Val Ile Asp Asp Leu Glu Asn Val Arg Glu Tyr
            20                  25                  30

Asp Ala Asp Asp Asp Gly Gly His Tyr Pro Leu Ile Phe Arg Glu Phe
        35                  40                  45

Ser Leu Glu Gln Leu Arg Ile Ala Thr Asp Gly Phe Ser Ala Gly Asn
    50                  55                  60

Ile Val Ser Glu His Asn Asp Ser Val Pro Asn Ile Val Tyr Lys Gly
65                  70                  75                  80

Lys Leu Gly Asp Gly Arg Arg Ile Ala Val Lys Arg Phe Gln Arg Leu
                85                  90                  95

Ser Trp Pro Asp Pro Phe Glu Phe Ile Asn Glu Ala Gln Ala Val Gly
```

```
            100                 105                 110

Arg Leu Arg Ser Glu His Met Ala Asn Leu Ile Gly Cys Cys Cys Asp
        115                 120                 125

Asp Asn Glu Arg Leu Leu Val Ala Glu Tyr Met Pro Asn Gly Thr Leu
    130                 135                 140

Ala Lys His Leu Phe His Trp Glu Lys Arg Pro Met Lys Trp Glu Met
145                 150                 155                 160

Arg Leu Lys Val Ala Leu His Thr Ala Arg Ala Leu Glu Tyr Cys Asn
                165                 170                 175

Asp Lys Gly Ile Asp Leu Tyr His Asp Leu Asn Pro Tyr Arg Ile Met
            180                 185                 190

Phe Asp Lys Thr Gly Ile Pro Lys Leu Ser Cys Phe Gly Leu Met Lys
        195                 200                 205

Asn Ser His Glu Gly Lys Ile Tyr Ser Thr Asn Leu Ala Phe Ala Pro
    210                 215                 220

Pro Glu Tyr Leu Arg Leu Gly Thr Val Ile Ala Glu Ser Val Thr Phe
225                 230                 235                 240

Ser Phe Gly Thr Leu Leu Leu Asp Leu Met Ser Gly Arg His Ile Pro
                245                 250                 255

Pro Asn His Ala Leu Asp Leu Phe Arg Gly Lys Asn Tyr Leu Val Leu
            260                 265                 270

Met Asp Ser Ala Leu Asp Gly Gln Phe Ser Asp Glu Asp Arg Thr Glu
        275                 280                 285

Leu Ile His Val Ala Ser Arg Cys Phe Lys Thr Glu Pro Glu Glu Arg
    290                 295                 300

Pro Ser Ile Lys Phe Leu Lys Ala Thr Leu Ser Arg Leu Gln Lys Arg
305                 310                 315                 320

Ala Lys Leu Cys Pro Ile Asn Val Lys Arg Pro Met Ser Pro Pro Ser
                325                 330                 335

Lys Asn Leu Pro Glu Lys Thr Lys Pro Ala Thr Glu Ser Leu Lys Leu
            340                 345                 350

Thr Pro Phe Gly Asp Ala Cys Ser Arg Ala Asp Leu Ser Ser Ile His
        355                 360                 365

Glu Leu Leu Glu Lys Leu Gly Tyr Glu Glu Asp Asn Gly Val Gly Asn
    370                 375                 380

Glu Phe Ser Phe Gln Met Trp Thr Gly Glu Met Gln Glu Asn Met Asp
385                 390                 395                 400

Tyr Lys Lys His Gly Asp Ala Ala Phe Leu Ala Lys Asp Phe Asp Thr
                405                 410                 415

Ala Ile Glu Phe Tyr Thr Glu Phe Met Thr Gly Ala Pro Thr Val Ser
            420                 425                 430

Pro Thr Val Leu Ala Arg Arg Cys Leu Cys Tyr Leu Met Thr Glu Met
        435                 440                 445

Phe Ser Glu Ala Leu Ser Asp Ala Met Gln Ala Gln Val Ala Ser Pro
    450                 455                 460

Glu Trp Pro Ile Pro Leu Tyr Leu Gln Ala Ala Cys Leu Phe Lys Leu
465                 470                 475                 480

Glu Met Glu Ala Glu Ala Lys Glu Ala Leu Arg His Gly Ser Ala Leu
                485                 490                 495

Glu Ala Tyr
```

<210> SEQ ID NO 21
<211> LENGTH: 1524
<212> TYPE: DNA

<213> ORGANISM: Arabidopsis thaliana

<400> SEQUENCE: 21

```
atgggttgtt gtcaatcgtc attcttgaaa ccgtcgtcat tgcatgacaa gaaaatcacc      60
tccgacgatt tatccggccg ccgtggaaaa ggagccaaac gtggtaatcg ccaccgtcat     120
gctaacatta atgaaggcag gggatggcat tttccgacg tgccagactt ctccgagttc     180
tcggcatcgg ttcttcgtga cgctacaaat aatttcaaca aaaacgctgt cgtatcagtt     240
tgttctgatc aagaaccaaa ccttgtttac caaggctgca ttaggagcga caaagataaa     300
cgtcttattg ccgttaaaaa attctccaaa acaacatggc ctgatcctaa acaattcgct     360
acagaagctc gggctatcgg cagtttgagg catgtaagac tagtgaattt gataggttat     420
tgttgtgaag gagatgaaag gttgcttgta tcggagtaca tgcctaatga aagcctaacc     480
aaacatctat ttcattggga gaaacaaacc atggaatggg ctatgcgatt gagagttgca     540
ctttatgtag ctgaagcttt agaatattgt aggcagagtg gactcaaatt gtaccatgat     600
ctcaatactt gtcgggttct ctttgatgag aatggaagtc ctcggctttc atgttttgga     660
tggatgaaaa atagcaaaga tggcaagaac ttcagcacaa atcttgctta tacaccgccc     720
gaatatctta gaagtggtac gttaattcca gagagtgttg tcttcagctt tgggacgttt     780
cttttggatc ttcttagtgg gaaacacatt cctccaagtc atgcggttgg tacaattcaa     840
aagcaaaact taaatgtctt gatggattca catttagaag gaaactatcc tgaggaagac     900
gcagccatgg tgtttgattt ggcttccaaa tgccttcaca ataaccctaa tgaacggcca     960
gaaattggag atatcatctc agttatcact acacttcaac aaaaactaga tgttccgtcc    1020
tatactatgc ttggaatttc aaaacttgaa aagcttgaaa tggaacaccc gaaatcttta    1080
atttacgatg catgtcacca aatggacctt gcagctcttc atcaaattct tgaagcaatg    1140
gagtacaaag aagatgaagt tacttgtgag ctctctttcc agcaatgggc tcaacagata    1200
aaagatgtgt gcaacactag acaacaaggc gattcggctt ttcggaacaa acatttcgaa    1260
tctgctattg ataaatatac tcagttcata gaaataggaa tcatgatctc tcccactgtt    1320
tatgcacgaa gaagcatgtg ctatctcttc tgcgaccaac cagatgcagc acttcgagac    1380
gcgatgcaag cacaatgtgt ctattcggac tggccaactg cattttacct tcaggccgtg    1440
gctctttcca aactgaatat ggtcgaagat tcagctacca tgctaaaaga agccttgatc    1500
ttggaagata agagaggctc ataa                                           1524
```

<210> SEQ ID NO 22
<211> LENGTH: 507
<212> TYPE: PRT
<213> ORGANISM: Arabidopsis thaliana

<400> SEQUENCE: 22

```
Met Gly Cys Cys Gln Ser Ser Phe Leu Lys Pro Ser Ser Leu His Asp
1               5                   10                  15

Lys Lys Ile Thr Ser Asp Asp Leu Ser Gly Arg Arg Gly Lys Gly Ala
            20                  25                  30

Lys Arg Gly Asn Arg His Arg His Ala Asn Ile Asn Glu Gly Arg Gly
        35                  40                  45

Trp His Phe Ser Asp Val Pro Asp Phe Ser Glu Phe Ser Ala Ser Val
    50                  55                  60

Leu Arg Asp Ala Thr Asn Asn Phe Asn Lys Asn Ala Val Val Ser Val
65                  70                  75                  80

Cys Ser Asp Gln Glu Pro Asn Leu Val Tyr Gln Gly Cys Ile Arg Ser
```

```
                85                  90                  95

Asp Lys Asp Lys Arg Leu Ile Ala Val Lys Lys Phe Ser Lys Thr Thr
            100                 105                 110

Trp Pro Asp Pro Lys Gln Phe Ala Thr Glu Ala Arg Ala Ile Gly Ser
        115                 120                 125

Leu Arg His Val Arg Leu Val Asn Leu Ile Gly Tyr Cys Cys Glu Gly
    130                 135                 140

Asp Glu Arg Leu Leu Val Ser Glu Tyr Met Pro Asn Glu Ser Leu Thr
145                 150                 155                 160

Lys His Leu Phe His Trp Glu Lys Gln Thr Met Glu Trp Ala Met Arg
                165                 170                 175

Leu Arg Val Ala Leu Tyr Val Ala Glu Ala Leu Glu Tyr Cys Arg Gln
            180                 185                 190

Ser Gly Leu Lys Leu Tyr His Asp Leu Asn Thr Cys Arg Val Leu Phe
        195                 200                 205

Asp Glu Asn Gly Ser Pro Arg Leu Ser Cys Phe Gly Trp Met Lys Asn
    210                 215                 220

Ser Lys Asp Gly Lys Asn Phe Ser Thr Asn Leu Ala Tyr Thr Pro Pro
225                 230                 235                 240

Glu Tyr Leu Arg Ser Gly Thr Leu Ile Pro Glu Ser Val Val Phe Ser
                245                 250                 255

Phe Gly Thr Phe Leu Leu Asp Leu Leu Ser Gly Lys His Ile Pro Pro
            260                 265                 270

Ser His Ala Val Gly Thr Ile Gln Lys Gln Asn Leu Asn Val Leu Met
        275                 280                 285

Asp Ser His Leu Glu Gly Asn Tyr Pro Glu Glu Asp Ala Ala Met Val
    290                 295                 300

Phe Asp Leu Ala Ser Lys Cys Leu His Asn Asn Pro Asn Glu Arg Pro
305                 310                 315                 320

Glu Ile Gly Asp Ile Ile Ser Val Ile Thr Thr Leu Gln Gln Lys Leu
                325                 330                 335

Asp Val Pro Ser Tyr Thr Met Leu Gly Ile Ser Lys Leu Glu Lys Leu
            340                 345                 350

Glu Met Glu His Pro Lys Ser Leu Ile Tyr Asp Ala Cys His Gln Met
        355                 360                 365

Asp Leu Ala Ala Leu His Gln Ile Leu Glu Ala Met Glu Tyr Lys Glu
    370                 375                 380

Asp Glu Val Thr Cys Glu Leu Ser Phe Gln Gln Trp Ala Gln Gln Ile
385                 390                 395                 400

Lys Asp Val Cys Asn Thr Arg Gln Gln Gly Asp Ser Ala Phe Arg Asn
                405                 410                 415

Lys His Phe Glu Ser Ala Ile Asp Lys Tyr Thr Gln Phe Ile Glu Ile
            420                 425                 430

Gly Ile Met Ile Ser Pro Thr Val Tyr Ala Arg Arg Ser Met Cys Tyr
        435                 440                 445

Leu Phe Cys Asp Gln Pro Asp Ala Ala Leu Arg Asp Ala Met Gln Ala
    450                 455                 460

Gln Cys Val Tyr Ser Asp Trp Pro Thr Ala Phe Tyr Leu Gln Ala Val
465                 470                 475                 480

Ala Leu Ser Lys Leu Asn Met Val Glu Asp Ser Ala Thr Met Leu Lys
                485                 490                 495

Glu Ala Leu Ile Leu Glu Asp Lys Arg Gly Ser
            500                 505
```

<210> SEQ ID NO 23
<211> LENGTH: 1398
<212> TYPE: DNA
<213> ORGANISM: Arabidopsis thaliana

<400> SEQUENCE: 23

```
atgggttgtt gttactcact atcttcaaca gtagatcctg ttcaagacca cacgaccgat      60

gcttcttccg aacctagaaa cggcggagga gaagatccac cattgacaaa attctctttt     120

tccgctctca agacggccac aaatcatttt agtcccgaaa acatcgtttc agatcaaacc     180

tccgatgttg tctttaaagg acgtttgcaa aacggtggtt tcgtcgctat caagagattt     240

aataacatgg cttggtctga tcctaaacta tttttggaag aggcacaaag agtagggaag     300

ttaagacaca agagactcgt aaatttgatt ggatattgct gtgatggaga taaaaggttt     360

cttgttgcag atttcatggc taatgatact cttgcgaagc gtttattcca gcggaaatat     420

caaaccatgg attggtctat taggttaaga gtcgcctatt ttgtagctga agcattggat     480

tattgcaaca ctgcaggctt tgcatcatac aataacttaa gcgcttacaa ggttttgttt     540

gatgaggatg gtgatgcatg tctttcttgt ttcggcttga tgaaggagat taataatgat     600

caaattacaa caggaagtgt gaaccctgaa aatgtgatat accgatttgg tactgtcctt     660

gtgaatcttc taagtggaaa gcaaattcct ccaagccacg ctcctgagat gatacatcga     720

aagaatgtgt ttaagttgat ggatccatac ctgaagggga agttctccat agatgaagct     780

aacgtagttt ataaactcgc ctctcaatgt ttgaagtacg agggtcaaga gagtcccaac     840

acaaaagaga ttgttgcaac gcttgaaacc ttgcaaacta gaacagaagc tccatcatat     900

gaagttgttg aaatgacaaa ccaagagaag gatgcatcat cgtcaagtaa tctttcgcca     960

ctaggagagg cttgtttgag aatggacctc gcatcgattc attcaatctt ggtcttggca    1020

ggatatgatg atgacaagga tatcatcgag ttatctttcg aagaatggat acaagaggtg    1080

aaagaacttc aagatgttcg aagaaacggt gatcgagcct tcgtagagca agacttcaaa    1140

accgctattg cctgttattc tcagttcgtt gaagagaggt cattggtata cccaagtgtt    1200

tacgcaaggc gtagtctaag ctatctattc tgcgatgagc cagaaaaggc cctcctcgat    1260

gggatgcatg cacagggagt gtttcctgat tggccaaccg ccttctactt gcagtctgtg    1320

gcattagcca aactcgacat gaacactgat tctgctgata ctttgaaaga agcagctctt    1380

cttgaagtaa agaaatag                                                   1398
```

<210> SEQ ID NO 24
<211> LENGTH: 465
<212> TYPE: PRT
<213> ORGANISM: Arabidopsis thaliana

<400> SEQUENCE: 24

```
Met Gly Cys Cys Tyr Ser Leu Ser Ser Thr Val Asp Pro Val Gln Asp
1               5                   10                  15

His Thr Thr Asp Ala Ser Ser Glu Pro Arg Asn Gly Gly Gly Glu Asp
            20                  25                  30

Pro Pro Leu Thr Lys Phe Ser Phe Ser Ala Leu Lys Thr Ala Thr Asn
        35                  40                  45

His Phe Ser Pro Glu Asn Ile Val Ser Asp Gln Thr Ser Asp Val Val
    50                  55                  60

Phe Lys Gly Arg Leu Gln Asn Gly Gly Phe Val Ala Ile Lys Arg Phe
65                  70                  75                  80

Asn Asn Met Ala Trp Ser Asp Pro Lys Leu Phe Leu Glu Glu Ala Gln
```

```
                85                  90                  95

Arg Val Gly Lys Leu Arg His Lys Arg Leu Val Asn Leu Ile Gly Tyr
            100                 105                 110

Cys Cys Asp Gly Asp Lys Arg Phe Leu Val Ala Asp Phe Met Ala Asn
        115                 120                 125

Asp Thr Leu Ala Lys Arg Leu Phe Gln Arg Lys Tyr Gln Thr Met Asp
    130                 135                 140

Trp Ser Ile Arg Leu Arg Val Ala Tyr Phe Val Ala Glu Ala Leu Asp
145                 150                 155                 160

Tyr Cys Asn Thr Ala Gly Phe Ala Ser Tyr Asn Asn Leu Ser Ala Tyr
                165                 170                 175

Lys Val Leu Phe Asp Glu Asp Gly Asp Ala Cys Leu Ser Cys Phe Gly
            180                 185                 190

Leu Met Lys Glu Ile Asn Asn Asp Gln Ile Thr Thr Gly Ser Val Asn
        195                 200                 205

Pro Glu Asn Val Ile Tyr Arg Phe Gly Thr Val Leu Val Asn Leu Leu
    210                 215                 220

Ser Gly Lys Gln Ile Pro Pro Ser His Ala Pro Glu Met Ile His Arg
225                 230                 235                 240

Lys Asn Val Phe Lys Leu Met Asp Pro Tyr Leu Lys Gly Lys Phe Ser
                245                 250                 255

Ile Asp Glu Ala Asn Val Val Tyr Lys Leu Ala Ser Gln Cys Leu Lys
            260                 265                 270

Tyr Glu Gly Gln Glu Ser Pro Asn Thr Lys Glu Ile Val Ala Thr Leu
        275                 280                 285

Glu Thr Leu Gln Thr Arg Thr Glu Ala Pro Ser Tyr Glu Val Val Glu
    290                 295                 300

Met Thr Asn Gln Glu Lys Asp Ala Ser Ser Ser Ser Asn Leu Ser Pro
305                 310                 315                 320

Leu Gly Glu Ala Cys Leu Arg Met Asp Leu Ala Ser Ile His Ser Ile
                325                 330                 335

Leu Val Leu Ala Gly Tyr Asp Asp Asp Lys Asp Ile Ile Glu Leu Ser
            340                 345                 350

Phe Glu Glu Trp Ile Gln Glu Val Lys Glu Leu Gln Asp Val Arg Arg
        355                 360                 365

Asn Gly Asp Arg Ala Phe Val Glu Gln Asp Phe Lys Thr Ala Ile Ala
    370                 375                 380

Cys Tyr Ser Gln Phe Val Glu Glu Arg Ser Leu Val Tyr Pro Ser Val
385                 390                 395                 400

Tyr Ala Arg Arg Ser Leu Ser Tyr Leu Phe Cys Asp Glu Pro Glu Lys
                405                 410                 415

Ala Leu Leu Asp Gly Met His Ala Gln Gly Val Phe Pro Asp Trp Pro
            420                 425                 430

Thr Ala Phe Tyr Leu Gln Ser Val Ala Leu Ala Lys Leu Asp Met Asn
        435                 440                 445

Thr Asp Ser Ala Asp Thr Leu Lys Glu Ala Ala Leu Leu Glu Val Lys
    450                 455                 460

Lys
465


<210> SEQ ID NO 25
<211> LENGTH: 15
<212> TYPE: PRT
<213> ORGANISM: Arabidopsis thaliana
<220> FEATURE:
```

```
<221> NAME/KEY: MISC_FEATURE
<222> LOCATION: (1)..(1)
<223> OTHER INFORMATION: X is either serine, arginine, or isoleucine
<220> FEATURE:
<221> NAME/KEY: MISC_FEATURE
<222> LOCATION: (2)..(2)
<223> OTHER INFORMATION: X is either tyrosine or phenylalanine
<220> FEATURE:
<221> NAME/KEY: MISC_FEATURE
<222> LOCATION: (8)..(8)
<223> OTHER INFORMATION: X is either tyrosine or phenylalanine
<220> FEATURE:
<221> NAME/KEY: MISC_FEATURE
<222> LOCATION: (9)..(9)
<223> OTHER INFORMATION: X is either threonine or alanine.

<400> SEQUENCE: 25

Xaa Xaa Ser Thr Asn Leu Ala Xaa Xaa Pro Pro Glu Tyr Leu Arg
1               5                   10                  15


<210> SEQ ID NO 26
<211> LENGTH: 512
<212> TYPE: PRT
<213> ORGANISM: Arabidopsis thaliana

<400> SEQUENCE: 26

Met Gly Cys Cys Gln Ser Leu Phe Ser Gly Asp Asn Pro Leu Gly Lys
1               5                   10                  15

Asp Gly Val Gln Pro Gln Pro Leu Ser Gln Asn Asn His Gly Gly Ala
            20                  25                  30

Thr Thr Ala Asp Asn Gly Gly Ser Gly Gly Ala Ser Gly Val Gly Gly
        35                  40                  45

Gly Gly Gly Gly Gly Gly Ile Pro Ser Phe Ser Glu Phe Ser Phe Ala
    50                  55                  60

Asp Leu Lys Ala Ala Thr Asn Asn Phe Ser Ser Asp Asn Ile Val Ser
65                  70                  75                  80

Glu Ser Gly Glu Lys Ala Pro Asn Leu Val Tyr Lys Gly Arg Leu Gln
                85                  90                  95

Asn Arg Arg Trp Ile Ala Val Lys Lys Phe Thr Lys Met Ala Trp Pro
            100                 105                 110

Glu Pro Lys Gln Phe Ala Glu Glu Ala Trp Gly Val Gly Lys Leu Arg
        115                 120                 125

His Asn Arg Leu Ala Asn Leu Ile Gly Tyr Cys Cys Asp Gly Asp Glu
    130                 135                 140

Arg Leu Leu Val Ala Glu Phe Met Pro Asn Asp Thr Leu Ala Lys His
145                 150                 155                 160

Leu Phe His Trp Glu Asn Gln Thr Ile Glu Trp Ala Met Arg Leu Arg
                165                 170                 175

Val Gly Tyr Tyr Ile Ala Glu Ala Leu Asp Tyr Cys Ser Thr Glu Gly
            180                 185                 190

Arg Pro Leu Tyr His Asp Leu Asn Ala Tyr Arg Val Leu Phe Asp Glu
        195                 200                 205

Asp Gly Asp Pro Arg Leu Ser Cys Phe Gly Leu Met Lys Asn Ser Arg
    210                 215                 220

Asp Gly Lys Ser Tyr Ser Thr Asn Leu Ala Tyr Thr Pro Pro Glu Tyr
225                 230                 235                 240

Leu Arg Asn Gly Arg Val Thr Pro Glu Ser Val Thr Tyr Ser Phe Gly
                245                 250                 255

Thr Val Leu Leu Asp Leu Leu Ser Gly Lys His Ile Pro Pro Ser His
            260                 265                 270
```

```
Ala Leu Asp Met Ile Arg Gly Lys Asn Ile Ile Leu Leu Met Asp Ser
        275                 280                 285

His Leu Glu Gly Lys Phe Ser Thr Glu Glu Ala Thr Val Val Val Glu
    290                 295                 300

Leu Ala Ser Gln Cys Leu Gln Tyr Glu Pro Arg Glu Arg Pro Asn Thr
305                 310                 315                 320

Lys Asp Leu Val Ala Thr Leu Ala Pro Leu Gln Thr Lys Ser Asp Val
                325                 330                 335

Pro Ser Tyr Val Met Leu Gly Ile Lys Lys Gln Glu Glu Ala Pro Ser
            340                 345                 350

Thr Pro Gln Arg Pro Leu Ser Pro Leu Gly Glu Ala Cys Ser Arg Met
        355                 360                 365

Asp Leu Thr Ala Ile His Gln Ile Leu Val Met Thr His Tyr Arg Asp
    370                 375                 380

Asp Glu Gly Thr Asn Glu Leu Ser Phe Gln Glu Trp Thr Gln Gln Met
385                 390                 395                 400

Lys Asp Met Leu Asp Ala Arg Lys Arg Gly Asp Gln Ser Phe Arg Glu
                405                 410                 415

Lys Asp Phe Lys Thr Ala Ile Asp Cys Tyr Ser Gln Phe Ile Asp Val
            420                 425                 430

Gly Thr Met Val Ser Pro Thr Val Phe Gly Arg Arg Ser Leu Cys Tyr
        435                 440                 445

Leu Leu Cys Asp Gln Pro Asp Ala Ala Leu Arg Asp Ala Met Gln Ala
    450                 455                 460

Gln Cys Val Tyr Pro Asp Trp Pro Thr Ala Phe Tyr Met Gln Ser Val
465                 470                 475                 480

Ala Leu Ala Lys Leu Asn Met Asn Thr Asp Ala Ala Asp Met Leu Asn
                485                 490                 495

Glu Ala Ala Gln Leu Glu Glu Lys Arg Gln Arg Gly Gly Arg Gly Ser
            500                 505                 510


<210> SEQ ID NO 27
<211> LENGTH: 489
<212> TYPE: PRT
<213> ORGANISM: Arabidopsis thaliana

<400> SEQUENCE: 27

Met Gly Cys Leu His Ser Lys Thr Ala Asn Leu Pro Ser Ser Asp Asp
1               5                   10                  15

Pro Ser Ala Pro Asn Lys Pro Glu Ser Val Asn Gly Asp Gln Val Asp
            20                  25                  30

Gln Glu Ile Gln Asn Phe Lys Glu Phe Glu Leu Asn Glu Leu Arg Lys
        35                  40                  45

Ala Thr Asn Gly Phe Ser Pro Ser Cys Ile Val Ser Glu Gly Gly Glu
    50                  55                  60

Lys Ala Pro Asn Val Val Tyr Arg Gly Lys Leu Glu Gly Asn His Leu
65                  70                  75                  80

Val Ala Ile Lys Arg Phe Ser Arg Gln Ser Trp Pro Asp Ala Gln Gln
                85                  90                  95

Phe Val Val Glu Ala Thr Gly Val Gly Lys Leu Arg Asn Lys Arg Ile
            100                 105                 110

Val Ser Leu Ile Gly Cys Cys Ala Glu Gly Asp Glu Arg Leu Leu Val
        115                 120                 125

Ala Glu Tyr Met Pro Asn Asp Thr Leu Ser Lys His Leu Phe His Trp
    130                 135                 140
```

```
Glu Lys Gln Pro Leu Pro Trp Asp Met Arg Val Arg Ile Ala Asp Tyr
145                 150                 155                 160

Ile Ala Glu Ala Leu Asp Tyr Cys Asn Ile Glu Asn Arg Lys Ile Tyr
                165                 170                 175

His Asp Leu Asn Ala Tyr Arg Ile Leu Phe Asp Glu Glu Gly Asp Pro
            180                 185                 190

Arg Leu Ser Thr Phe Gly Leu Met Lys Asn Ser Arg Asp Gly Lys Ser
        195                 200                 205

Tyr Ser Thr Asn Leu Ala Tyr Thr Pro Pro Glu Phe Leu Arg Thr Gly
    210                 215                 220

Arg Val Ile Pro Glu Ser Val Ile Phe Ser Tyr Gly Thr Ile Leu Leu
225                 230                 235                 240

Asp Leu Leu Ser Gly Lys His Ile Pro Pro Ser His Ala Leu Asp Ile
                245                 250                 255

Ile Arg Gly Lys Asn Ala Leu Leu Leu Met Asp Ser Ser Leu Glu Gly
            260                 265                 270

Gln Tyr Ala Asn Asp Asp Ala Thr Lys Leu Val Asp Leu Ala Ser Lys
        275                 280                 285

Cys Leu Gln Ser Glu Ala Lys Asp Arg Pro Asp Thr Lys Phe Leu Leu
    290                 295                 300

Ser Ala Val Ala Pro Leu Gln Lys Gln Glu Glu Val Ala Ser His Val
305                 310                 315                 320

Leu Met Gly Leu Pro Lys Asn Thr Val Ile Leu Pro Thr Met Leu Ser
                325                 330                 335

Pro Leu Gly Lys Ala Cys Ala Lys Met Asp Leu Ala Thr Phe His Asp
            340                 345                 350

Ile Leu Leu Lys Thr Gly Tyr Arg Asp Glu Glu Gly Ala Glu Asn Glu
        355                 360                 365

Leu Ser Phe Gln Glu Trp Thr Gln Gln Val Gln Glu Met Leu Asn Thr
    370                 375                 380

Lys Lys Phe Gly Asp Ile Ala Phe Arg Asp Lys Asp Phe Lys Asn Ser
385                 390                 395                 400

Ile Glu Tyr Tyr Ser Lys Leu Val Gly Met Met Pro Val Pro Ser Ala
                405                 410                 415

Thr Val Phe Ala Arg Arg Ala Phe Ser Tyr Leu Met Thr Asp Gln Gln
            420                 425                 430

Glu Leu Ala Leu Arg Asp Ala Met Gln Ala Gln Val Cys Ile Pro Glu
        435                 440                 445

Trp Pro Thr Ala Phe Tyr Leu Gln Ala Leu Ala Leu Ser Lys Leu Gly
    450                 455                 460

Met Glu Thr Asp Ala Gln Asp Met Leu Asn Asp Gly Ala Ala Tyr Asp
465                 470                 475                 480

Ala Lys Arg Gln Asn Ser Trp Arg Cys
                485


<210> SEQ ID NO 28
<211> LENGTH: 489
<212> TYPE: PRT
<213> ORGANISM: Arabidopsis thaliana

<400> SEQUENCE: 28

Met Gly Gly Gln Cys Ser Ser Leu Ser Cys Cys Arg Asn Thr Ser His
1               5                   10                  15

Lys Thr Ala Val Leu Glu Ala Pro Asp Val Asp Asn Gly Glu Ser Ser
            20                  25                  30
```

```
Glu Ile Thr Asp Val Pro Asn Phe Arg Glu Tyr Thr Leu Glu Gln Leu
        35                  40                  45

Lys Ala Ala Thr Ser Gly Phe Ala Val Glu Tyr Ile Val Ser Glu His
    50                  55                  60

Gly Glu Lys Ala Pro Asn Val Val Tyr Lys Gly Lys Leu Glu Asn Gln
65                  70                  75                  80

Lys Lys Ile Ala Val Lys Arg Phe Thr Arg Met Ala Trp Pro Asp Ser
                85                  90                  95

Arg Gln Phe Leu Glu Glu Ala Arg Ser Val Gly Gln Leu Arg Ser Glu
            100                 105                 110

Arg Met Ala Asn Leu Leu Gly Cys Cys Cys Glu Gly Asp Glu Arg Leu
        115                 120                 125

Leu Val Ala Glu Phe Met Pro Asn Glu Thr Leu Ala Lys His Leu Phe
    130                 135                 140

His Trp Glu Thr Gln Pro Met Lys Trp Thr Met Arg Leu Arg Val Val
145                 150                 155                 160

Leu Tyr Leu Ala Gln Ala Leu Glu Tyr Cys Thr Ser Lys Gly Arg Thr
                165                 170                 175

Leu Tyr His Asp Leu Asn Ala Tyr Arg Val Leu Phe Asp Glu Glu Cys
            180                 185                 190

Asn Pro Arg Leu Ser Thr Phe Gly Leu Met Lys Asn Ser Arg Asp Gly
        195                 200                 205

Lys Ser Tyr Ser Thr Asn Leu Ala Phe Thr Pro Pro Glu Tyr Leu Arg
    210                 215                 220

Thr Gly Arg Ile Thr Pro Glu Ser Val Ile Tyr Ser Phe Gly Thr Leu
225                 230                 235                 240

Leu Leu Asp Leu Leu Ser Gly Lys His Ile Pro Pro Ser His Ala Leu
                245                 250                 255

Asp Leu Ile Arg Asp Arg Asn Leu Gln Thr Leu Thr Asp Ser Cys Leu
            260                 265                 270

Asp Gly Gln Phe Ser Asp Ser Asp Gly Thr Glu Leu Val Arg Leu Ala
        275                 280                 285

Ser Arg Cys Leu Gln Tyr Glu Ala Arg Glu Arg Pro Asn Thr Lys Ser
    290                 295                 300

Leu Val Thr Ala Leu Thr Pro Leu Gln Lys Glu Thr Glu Val Leu Ser
305                 310                 315                 320

His Val Leu Met Gly Leu Pro His Ser Gly Ser Val Ser Pro Leu Ser
                325                 330                 335

Pro Leu Gly Glu Ala Cys Ser Arg Arg Asp Leu Thr Ala Met Leu Glu
            340                 345                 350

Ile Leu Glu Lys Leu Gly Tyr Lys Asp Asp Glu Gly Val Thr Asn Glu
        355                 360                 365

Leu Ser Phe His Met Trp Thr Asp Gln Met Gln Glu Ser Leu Asn Ser
    370                 375                 380

Lys Lys Lys Gly Asp Val Ala Phe Arg Gln Lys Asp Phe Arg Glu Ala
385                 390                 395                 400

Ile Glu Cys Tyr Thr Gln Phe Ile Asp Gly Gly Met Ile Ser Pro Thr
                405                 410                 415

Val Cys Ala Arg Arg Ser Leu Cys Tyr Leu Met Ser Asp Met Pro Lys
            420                 425                 430

Glu Ala Leu Asp Asp Ala Ile Gln Ala Gln Val Ile Ser Pro Val Trp
        435                 440                 445

His Val Ala Ser Tyr Leu Gln Ser Ala Ser Leu Gly Ile Leu Gly Met
    450                 455                 460
```

```
Glu Lys Glu Ser Gln Ile Ala Leu Lys Glu Gly Ser Asn Leu Glu Ala
465                 470                 475                 480

Lys Met Asn Gly Val Pro Arg Val Lys
                485
```

<210> SEQ ID NO 29
<211> LENGTH: 483
<212> TYPE: PRT
<213> ORGANISM: Arabidopsis thaliana

<400> SEQUENCE: 29

```
Met Gly Gly Gln Ser Ser Lys Ile Gly Thr Cys Cys Ser His Lys Thr
1               5                   10                  15

Thr Ala Leu Glu Ala Pro Asp Val Glu Asn Lys Glu Asn Gly Glu Val
            20                  25                  30

Asn Gly Val His Ser Phe Arg Glu Tyr Ser Leu Glu Gln Leu Lys Ile
        35                  40                  45

Ala Thr Ser Cys Phe Ala Leu Glu Asn Val Val Ser Glu His Gly Glu
    50                  55                  60

Thr Ala Pro Asn Val Val Tyr Gln Gly Lys Leu Glu Asn His Met Lys
65                  70                  75                  80

Ile Ala Ile Lys Arg Phe Ser Gly Thr Ala Trp Pro Asp Pro Arg Gln
                85                  90                  95

Phe Leu Glu Glu Ala Arg Leu Val Gly Gln Leu Arg Ser Lys Arg Met
            100                 105                 110

Ala Asn Leu Leu Gly Tyr Cys Cys Glu Gly Gly Glu Arg Leu Leu Val
        115                 120                 125

Ala Glu Phe Met Pro Asn Glu Thr Leu Ala Lys His Leu Phe His Trp
    130                 135                 140

Asp Thr Glu Pro Met Lys Trp Ala Met Arg Leu Arg Val Ala Leu Tyr
145                 150                 155                 160

Ile Ser Glu Ala Leu Glu Tyr Cys Ser Asn Asn Gly His Thr Leu Tyr
                165                 170                 175

His Asp Leu Asn Ala Tyr Arg Val Leu Phe Asp Glu Glu Cys Asn Pro
            180                 185                 190

Arg Leu Ser Thr Phe Gly Leu Met Lys Asn Ser Arg Asp Gly Lys Ser
        195                 200                 205

Tyr Ser Thr Asn Leu Ala Phe Thr Pro Pro Glu Tyr Leu Arg Thr Gly
    210                 215                 220

Arg Ile Thr Ala Glu Ser Val Ile Tyr Ser Phe Gly Thr Leu Leu Leu
225                 230                 235                 240

Asp Leu Leu Thr Gly Lys His Ile Pro Pro Ser His Ala Leu Asp Leu
                245                 250                 255

Ile Arg Asp Arg Asn Leu Gln Thr Leu Thr Asp Ser Cys Leu Glu Gly
            260                 265                 270

Gln Phe Ser Asp Ser Asp Gly Thr Glu Leu Val Arg Leu Thr Ser Cys
        275                 280                 285

Cys Leu Gln Tyr Glu Ala Arg Glu Arg Pro Asn Ile Lys Ser Leu Val
    290                 295                 300

Thr Ala Leu Ile Ser Leu Gln Lys Asp Thr Glu Val Leu Ser His Val
305                 310                 315                 320

Leu Met Gly Leu Pro Gln Ser Gly Thr Phe Ala Ser Pro Pro Ser Pro
                325                 330                 335

Phe Ala Glu Ala Cys Ser Gly Lys Asp Leu Thr Ser Met Val Glu Ile
            340                 345                 350
```

```
Leu Glu Lys Ile Gly Tyr Lys Asp Asp Glu Asp Leu Ser Phe Met Trp
        355                 360                 365

Thr Glu Gln Met Gln Glu Ala Ile Asn Ser Lys Lys Lys Gly Asp Ile
    370                 375                 380

Ala Phe Arg Arg Lys Asp Phe Ser Glu Ala Ile Glu Phe Tyr Thr Gln
385                 390                 395                 400

Phe Leu Asp Leu Gly Met Ile Ser Ala Thr Val Leu Val Arg Arg Ser
                405                 410                 415

Gln Ser Tyr Leu Met Ser Asn Met Ala Lys Glu Ala Leu Asp Asp Ala
            420                 425                 430

Met Lys Ala Gln Gly Ile Ser Pro Val Trp Tyr Val Ala Leu Tyr Leu
        435                 440                 445

Gln Ser Ala Ala Leu Ser Val Leu Gly Met Glu Lys Glu Ser Gln Ile
    450                 455                 460

Ala Leu Thr Glu Gly Ser Ile Leu Glu Ala Arg Lys Ile Ser Ala Ser
465                 470                 475                 480

Thr Gln Asn


<210> SEQ ID NO 30
<211> LENGTH: 359
<212> TYPE: PRT
<213> ORGANISM: Arabidopsis thaliana

<400> SEQUENCE: 30

Met Pro Phe Glu Thr Leu Ser Lys His Leu Phe His Trp Asp Ser Gln
1               5                   10                  15

Pro Met Lys Trp Ser Met Arg Leu Arg Val Ala Leu Tyr Leu Ala Gln
            20                  25                  30

Ala Leu Glu Tyr Cys Ser Ser Lys Gly Arg Ala Leu Tyr His Asp Leu
        35                  40                  45

Asn Ala Tyr Arg Ile Leu Phe Asp Gln Asp Gly Asn Pro Arg Leu Ser
    50                  55                  60

Cys Phe Gly Leu Met Lys Asn Ser Arg Asp Gly Lys Ser Tyr Ser Thr
65                  70                  75                  80

Asn Leu Ala Phe Thr Pro Pro Glu Tyr Leu Arg Thr Gly Arg Val Ile
                85                  90                  95

Pro Glu Ser Val Val Tyr Ser Phe Gly Thr Leu Leu Leu Asp Leu Leu
            100                 105                 110

Ser Gly Lys His Ile Pro Pro Ser His Ala Leu Asp Leu Ile Arg Gly
        115                 120                 125

Lys Asn Phe Leu Met Leu Met Asp Ser Cys Leu Asp Gly His Phe Ser
    130                 135                 140

Asn Asp Asp Gly Thr Asp Leu Val Arg Leu Ala Ser Arg Cys Leu Gln
145                 150                 155                 160

Tyr Glu Ala Arg Glu Arg Pro Asn Val Lys Ser Leu Val Ser Ser Leu
                165                 170                 175

Ala Pro Leu Gln Lys Glu Thr Asp Ile Pro Ser His Val Leu Met Gly
            180                 185                 190

Ile Pro His Gly Ala Ala Ser Pro Lys Glu Thr Thr Ser Leu Thr Pro
        195                 200                 205

Leu Gly Asp Ala Cys Ser Arg His Asp Leu Thr Ala Ile His Glu Ile
    210                 215                 220

Leu Glu Lys Val Gly Tyr Lys Asp Asp Glu Gly Val Ala Asn Glu Leu
225                 230                 235                 240
```

```
Ser Phe Gln Val Trp Thr Asp Gln Ile Gln Glu Thr Leu Asn Ser Lys
                245                 250                 255

Lys Gln Gly Asp Ala Ala Phe Lys Gly Lys Asp Phe Val Thr Ala Val
            260                 265                 270

Glu Cys Tyr Thr Gln Phe Ile Glu Asp Gly Thr Met Val Ser Pro Thr
        275                 280                 285

Val Phe Ala Arg Arg Cys Leu Cys Tyr Leu Met Ser Asn Met Pro Gln
    290                 295                 300

Glu Ala Leu Gly Asp Ala Met Gln Ala Gln Val Val Ser Pro Glu Trp
305                 310                 315                 320

Pro Thr Ala Phe Tyr Leu Gln Ala Ala Ala Leu Phe Ser Leu Gly Met
                325                 330                 335

Asp Lys Asp Ala Cys Glu Thr Leu Lys Asp Gly Thr Ser Leu Glu Ala
            340                 345                 350

Lys Lys His Asn Asn Arg Asn
        355


<210> SEQ ID NO 31
<211> LENGTH: 490
<212> TYPE: PRT
<213> ORGANISM: Arabidopsis thaliana

<400> SEQUENCE: 31

Met Gly Ala Arg Cys Ser Lys Phe Ser Phe Cys Leu Phe Pro Ser His
1               5                   10                  15

Phe Lys Ser Ala Ser Val Leu Glu Ser Pro Asp Ile Glu Asn Gly Gly
            20                  25                  30

Lys Val Trp Pro Thr Phe Lys Glu Phe Lys Leu Glu Gln Leu Lys Ser
        35                  40                  45

Ala Thr Gly Gly Phe Ser Ser Asp Asn Ile Val Ser Glu His Gly Glu
    50                  55                  60

Lys Ala Pro Asn Val Val Tyr Arg Gly Arg Leu Asp Asp Gly Arg Leu
65                  70                  75                  80

Ile Ala Val Lys Arg Phe Asn Arg Leu Ala Trp Ala Asp His Arg Gln
                85                  90                  95

Phe Leu Asp Glu Ala Lys Ala Val Gly Ser Leu Arg Ser Asp Arg Leu
            100                 105                 110

Ala Asn Leu Ile Gly Cys Cys Phe Glu Gly Glu Glu Arg Leu Leu Val
        115                 120                 125

Ala Glu Phe Met Pro His Glu Thr Leu Ala Lys His Leu Phe His Trp
    130                 135                 140

Glu Asn Asn Pro Met Lys Trp Ala Met Arg Leu Arg Val Ala Leu Cys
145                 150                 155                 160

Leu Ala Gln Ala Leu Glu Tyr Cys Ser Asn Lys Gly Arg Ala Leu Tyr
                165                 170                 175

His Asp Leu Asn Ala Tyr Arg Val Leu Phe Asp Lys Asp Gly Asn Pro
            180                 185                 190

Arg Leu Ser Cys Phe Gly Leu Met Lys Asn Ser Arg Asp Gly Lys Ser
        195                 200                 205

Tyr Ser Thr Asn Leu Ala Phe Thr Pro Pro Glu Tyr Leu Arg Thr Gly
    210                 215                 220

Arg Val Thr Pro Glu Ser Val Val Phe Ser Phe Gly Thr Val Leu Leu
225                 230                 235                 240

Asp Leu Met Ser Gly Lys His Ile Pro Pro Ser His Ala Leu Asp Leu
                245                 250                 255
```

```
Ile Arg Gly Lys Asn Cys Ala Met Leu Met Asp Ser Ala Leu Glu Gly
            260                 265                 270

His Phe Ser Asn Glu Asp Gly Thr Glu Leu Val Arg Leu Ala Thr Arg
        275                 280                 285

Cys Leu Gln Tyr Glu Ala Arg Glu Arg Pro Asn Val Lys Ser Leu Val
    290                 295                 300

Thr Ser Leu Val Thr Leu Gln Lys Glu Ser Asp Val Ala Ser Tyr Val
305                 310                 315                 320

Leu Met Gly Ile Pro His Glu Thr Glu Ala Glu Glu Glu Ser Pro Leu
                325                 330                 335

Ser Leu Thr Pro Phe Gly Asp Ala Cys Leu Arg Val Asp Leu Thr Ala
            340                 345                 350

Ile Gln Glu Ile Leu Ser Lys Ile Gly Tyr Lys Asp Asp Glu Gly Ile
        355                 360                 365

Ala Asn Glu Leu Ser Phe Gln Met Trp Thr Asn Gln Met Gln Glu Ser
    370                 375                 380

Leu Asn Ser Lys Lys Gln Gly Asp Leu Ala Phe Arg Ser Lys Asp Phe
385                 390                 395                 400

Thr Thr Ala Val Asp Cys Tyr Thr Gln Phe Ile Asp Gly Gly Thr Met
                405                 410                 415

Val Ser Pro Thr Val His Ala Arg Arg Cys Leu Ser Tyr Leu Met Asn
            420                 425                 430

Asp Asn Ala Gln Glu Ala Leu Thr Asp Ala Leu Gln Ala Gln Val Val
        435                 440                 445

Ser Pro Asp Trp Pro Thr Ala Leu Tyr Leu Gln Ala Ala Cys Leu Phe
    450                 455                 460

Lys Leu Gly Met Glu Ala Asp Ala Gln Gln Ala Leu Lys Asp Gly Thr
465                 470                 475                 480

Thr Leu Glu Ala Lys Lys Ser Asn Lys Arg
                485                 490
```

<210> SEQ ID NO 32
<211> LENGTH: 487
<212> TYPE: PRT
<213> ORGANISM: Arabidopsis thaliana

<400> SEQUENCE: 32

```
Met Gly Cys Glu Val Ser Lys Leu Cys Ala Phe Cys Cys Val Ser Asp
1               5                   10                  15

Pro Glu Gly Ser Asn His Gly Val Thr Gly Leu Asp Glu Asp Arg Arg
            20                  25                  30

Gly Glu Gly Asn Asp Leu Pro Gln Phe Arg Glu Phe Ser Ile Glu Thr
        35                  40                  45

Leu Arg Asn Ala Thr Ser Gly Phe Ala Thr Glu Asn Ile Val Ser Glu
    50                  55                  60

His Gly Glu Lys Ala Pro Asn Val Val Tyr Lys Gly Lys Leu Asp Asn
65                  70                  75                  80

Gln Arg Arg Ile Ala Val Lys Arg Phe Asn Arg Lys Ala Trp Pro Asp
                85                  90                  95

Ser Arg Gln Phe Leu Glu Glu Ala Lys Ala Val Gly Gln Leu Arg Asn
            100                 105                 110

Tyr Arg Met Ala Asn Leu Leu Gly Cys Cys Tyr Glu Gly Glu Glu Arg
        115                 120                 125

Leu Leu Val Ala Glu Phe Met Pro Asn Glu Thr Leu Ala Lys His Leu
    130                 135                 140
```

```
Phe His Trp Glu Ser Gln Pro Met Lys Trp Ala Met Arg Leu Arg Val
145                 150                 155                 160

Ala Leu His Ile Ala Gln Ala Leu Glu Tyr Cys Thr Gly Lys Gly Arg
                165                 170                 175

Ala Leu Tyr His Asp Leu Asn Ala Tyr Arg Val Leu Phe Asp Asp Asp
            180                 185                 190

Ser Asn Pro Arg Leu Ser Cys Phe Gly Leu Met Lys Asn Ser Arg Asp
        195                 200                 205

Gly Lys Ser Tyr Ser Thr Asn Leu Ala Phe Thr Pro Pro Glu Tyr Leu
    210                 215                 220

Arg Thr Gly Arg Val Thr Pro Glu Ser Val Met Tyr Ser Tyr Gly Thr
225                 230                 235                 240

Leu Leu Leu Asp Leu Leu Ser Gly Lys His Ile Pro Pro Ser His Ala
                245                 250                 255

Leu Asp Leu Ile Arg Asp Arg Asn Ile Gln Met Leu Ile Asp Ser Cys
            260                 265                 270

Leu Glu Gly Gln Phe Ser Ser Asp Asp Gly Thr Glu Leu Ile Arg Leu
        275                 280                 285

Ala Ser Arg Cys Leu Gln Tyr Glu Pro Arg Glu Arg Pro Asn Pro Lys
    290                 295                 300

Ser Leu Val Thr Ala Met Ile Pro Leu Gln Lys Asp Leu Glu Thr Pro
305                 310                 315                 320

Ser His Gln Leu Met Gly Ile Pro Ser Ser Ala Ser Thr Thr Pro Leu
                325                 330                 335

Ser Pro Leu Gly Glu Ala Cys Leu Arg Thr Asp Leu Thr Ala Ile His
            340                 345                 350

Glu Ile Leu Glu Lys Leu Ser Tyr Lys Asp Asp Glu Gly Ala Ala Thr
        355                 360                 365

Glu Leu Ser Phe Gln Met Trp Thr Asn Gln Met Gln Asp Ser Leu Asn
    370                 375                 380

Phe Lys Lys Lys Gly Asp Val Ala Phe Arg His Lys Glu Phe Ala Asn
385                 390                 395                 400

Ala Ile Asp Cys Tyr Ser Gln Phe Ile Glu Gly Gly Thr Met Val Ser
                405                 410                 415

Pro Thr Val Tyr Ala Arg Arg Ser Leu Cys Tyr Leu Met Asn Glu Met
            420                 425                 430

Pro Gln Glu Ala Leu Asn Asp Ala Met Gln Ala Gln Val Ile Ser Pro
        435                 440                 445

Ala Trp His Ile Ala Ser Tyr Leu Gln Ala Val Ala Leu Ser Ala Leu
    450                 455                 460

Gly Gln Glu Asn Glu Ala His Ala Ala Leu Lys Asp Gly Ser Met Leu
465                 470                 475                 480

Glu Ser Lys Arg Asn Arg Leu
                485


<210> SEQ ID NO 33
<211> LENGTH: 487
<212> TYPE: PRT
<213> ORGANISM: Arabidopsis thaliana

<400> SEQUENCE: 33

Met Gly Cys Glu Val Ser Lys Leu Ser Ala Leu Cys Cys Val Ser Glu
1               5                   10                  15

Ser Gly Arg Ser Asn Pro Asp Val Thr Gly Leu Asp Glu Glu Gly Arg
            20                  25                  30
```

```
Gly Glu Ser Asn Asp Leu Pro Gln Phe Arg Glu Phe Ser Ile Glu Thr
        35                  40                  45

Ile Arg Asn Ala Thr Ser Gly Phe Ala Ala Glu Asn Ile Val Ser Glu
    50                  55                  60

His Gly Glu Arg Ala Pro Asn Val Val Tyr Lys Gly Lys Leu Glu Asn
65                  70                  75                  80

Gln Arg Arg Ile Ala Val Lys Arg Phe Asn Arg Lys Ser Trp Pro Asp
                85                  90                  95

Ser Arg Gln Phe Leu Glu Glu Ala Lys Ala Val Gly Gln Leu Arg Asn
            100                 105                 110

His Arg Met Ala Asn Leu Leu Gly Cys Cys Tyr Glu Asp Glu Glu Arg
        115                 120                 125

Leu Leu Ile Ala Glu Phe Met Pro Asn Glu Thr Leu Ala Lys His Leu
    130                 135                 140

Phe His Trp Glu Ser Gln Pro Met Lys Trp Ala Met Arg Leu Arg Val
145                 150                 155                 160

Ala Leu His Ile Ala Gln Ala Leu Glu Tyr Cys Thr Ser Lys Gly Arg
                165                 170                 175

Ala Leu Tyr His Asp Leu Asn Ala Tyr Arg Val Leu Phe Asp Asp Asp
            180                 185                 190

Ala Asn Pro Arg Leu Ser Cys Phe Gly Leu Met Lys Asn Ser Arg Asp
        195                 200                 205

Gly Lys Ser Tyr Ser Thr Asn Leu Ala Phe Thr Pro Pro Glu Tyr Leu
    210                 215                 220

Arg Thr Gly Arg Val Thr Pro Glu Ser Val Ile Tyr Ser Phe Gly Thr
225                 230                 235                 240

Leu Leu Leu Asp Leu Leu Ser Gly Lys His Ile Pro Pro Ser His Ala
                245                 250                 255

Leu Asp Leu Ile Arg Asp Arg Asn Ile Gln Met Leu Met Asp Ser Gly
            260                 265                 270

Leu Glu Gly Gln Phe Ser Ser Asp Asp Gly Thr Glu Leu Ile Arg Leu
        275                 280                 285

Ala Ser Arg Cys Leu Gln Tyr Glu Pro Arg Glu Arg Pro Asn Pro Lys
    290                 295                 300

Ser Leu Val Ser Ala Met Ile Pro Leu Gln Lys Asp Leu Glu Ile Ala
305                 310                 315                 320

Ser His Gln Leu Leu Gly Val Pro Asn Ser Ala Thr Thr Thr Ala Leu
                325                 330                 335

Ser Pro Leu Gly Glu Ala Cys Leu Arg Ser Asp Leu Thr Ala Ile His
            340                 345                 350

Glu Ile Ile Glu Lys Leu Gly Tyr Lys Asp Asp Glu Gly Ala Thr Thr
        355                 360                 365

Glu Leu Ser Phe Gln Met Trp Thr Asp Gln Met Gln Asp Thr Leu Val
    370                 375                 380

Phe Lys Lys Lys Gly Asp Ser Ala Phe Arg His Lys Asp Phe Ala Lys
385                 390                 395                 400

Ala Ile Glu Cys Tyr Ser Gln Phe Ile Glu Val Gly Thr Met Gly Ser
                405                 410                 415

Pro Thr Val His Ala Arg Gln Ser Leu Cys Tyr Leu Met Asn Asp Met
            420                 425                 430

Pro Arg Glu Ala Leu Asn Asn Ala Met Gln Ala Gln Val Ile Ser Pro
        435                 440                 445

Ala Trp His Ile Ala Ser Tyr Leu Gln Ala Val Ala Leu Ser Ala Leu
    450                 455                 460
```

```
Gly Gln Glu Asn Glu Ala His Thr Ala Leu Lys Asp Gly Ala Met Leu
465                 470                 475                 480

Glu Ser Lys Arg Asn Pro Leu
                485


<210> SEQ ID NO 34
<211> LENGTH: 477
<212> TYPE: PRT
<213> ORGANISM: Arabidopsis thaliana

<400> SEQUENCE: 34

Met Ile Glu Arg Thr Asn Leu Ile Val Leu Ala Ala Asp Asn Lys Glu
1               5                   10                  15

Glu Asp Glu Gly Ser Thr Cys Pro Asn Phe Leu Glu Phe Ser Leu Glu
            20                  25                  30

Gln Leu Arg Val Ala Thr Asp Gly Phe Ser Ala Asp Asn Ile Val Ser
        35                  40                  45

Glu His Asn Glu Arg Val Pro Asn Ile Val Tyr Lys Gly Gln Leu Asn
    50                  55                  60

Asp Gly Arg Lys Ile Ala Val Lys Arg Phe Gln Arg Leu Ser Trp Pro
65                  70                  75                  80

Asp Ser Leu Glu Phe Ile Glu Glu Ala Gln Ala Val Gly Arg Cys Arg
                85                  90                  95

Ser Glu His Met Ala Asn Leu Ile Gly Cys Cys Ser Glu Gly His Glu
            100                 105                 110

Arg Leu Leu Val Ala Glu Tyr Met Pro Asn Glu Thr Leu Ala Lys His
        115                 120                 125

Leu Phe His Trp Glu Lys Arg Pro Met Lys Trp Glu Met Arg Leu Arg
    130                 135                 140

Val Ala Leu His Thr Ala Thr Ala Leu Glu Tyr Cys Asn Asp Trp Gly
145                 150                 155                 160

Ile Asp Leu Tyr His Asp Leu Asn Thr Tyr Arg Ile Leu Phe Asp Lys
                165                 170                 175

Val Gly Asn Pro Arg Leu Ser Cys Phe Gly Leu Met Lys Cys Ser Arg
            180                 185                 190

Glu Gly Lys Ser Tyr Ser Thr Asn Leu Ala Phe Ala Pro Pro Glu Tyr
        195                 200                 205

Leu Arg Leu Gly Thr Val Ile Pro Glu Ser Val Thr Phe Ser Phe Gly
    210                 215                 220

Thr Leu Leu Leu Asp Leu Met Ser Gly Arg His Ile Pro Pro Asn His
225                 230                 235                 240

Ala Leu Asp Leu Phe Arg Gly Lys Asn Tyr Leu Val Leu Met Asp Ser
                245                 250                 255

Ala Leu Asp Gly Gln Phe Ser Asp Glu Asp Arg Thr Glu Leu Ile His
            260                 265                 270

Leu Ala Ser Arg Cys Leu Arg Pro Glu Pro Asp Glu Arg Pro Ser Ile
        275                 280                 285

Lys Phe Leu Met Ser Ala Leu Ser Arg Leu Glu Lys Arg Ala Glu Leu
    290                 295                 300

Trp Pro Asn Val Lys Glu Glu Asn Ile Pro Thr Pro Ser Tyr Thr Glu
305                 310                 315                 320

Pro Ala Thr Lys Glu Pro Leu Pro Leu Thr Pro Phe Gly Glu Ala Cys
                325                 330                 335

Trp Arg Val Asp Leu Ser Gly Met His Glu Leu Leu Glu Lys Leu Gly
            340                 345                 350
```

```
Tyr Gly Glu Asp Asp Val Val Val Thr Asn Glu Phe Ser Phe Gln Met
        355                 360                 365

Trp Thr Gly Gln Met Gln Glu Asn Met Asp Tyr Lys Lys His Gly Asp
    370                 375                 380

Ala Ala Phe Arg Ala Lys Asp Phe Glu Thr Ala Ile Glu Phe Tyr Thr
385                 390                 395                 400

Glu Phe Met Ser Gly Ala Pro Val Val Ser Pro Thr Val Leu Ala Arg
                405                 410                 415

Arg Cys Leu Cys Tyr Leu Met Ser Asp Met Phe Arg Glu Ala Leu Ser
            420                 425                 430

Asp Ala Met Gln Thr Gln Val Ala Ser Pro Glu Phe Ser Ile Ala Leu
        435                 440                 445

Tyr Leu Gln Ala Ala Cys Leu Leu Lys Leu Gly Met Glu Ala Glu Ala
    450                 455                 460

Lys Glu Ala Leu Arg His Gly Ser Ser Leu Glu Ala Phe
465                 470                 475


<210> SEQ ID NO 35
<211> LENGTH: 499
<212> TYPE: PRT
<213> ORGANISM: Arabidopsis thaliana

<400> SEQUENCE: 35

Met Gly Cys Ile Cys Phe Lys Ser Trp Arg Arg Ser Ser Ser Ser Pro
1               5                   10                  15

Ser Ile Thr Ser Thr Val Ile Asp Asp Leu Glu Asn Val Arg Glu Tyr
            20                  25                  30

Asp Ala Asp Asp Asp Gly Gly His Tyr Pro Leu Ile Phe Arg Glu Phe
        35                  40                  45

Ser Leu Glu Gln Leu Arg Ile Ala Thr Asp Gly Phe Ser Ala Gly Asn
    50                  55                  60

Ile Val Ser Glu His Asn Asp Ser Val Pro Asn Ile Val Tyr Lys Gly
65                  70                  75                  80

Lys Leu Gly Asp Gly Arg Arg Ile Ala Val Lys Arg Phe Gln Arg Leu
                85                  90                  95

Ser Trp Pro Asp Pro Phe Glu Phe Ile Asn Glu Ala Gln Ala Val Gly
            100                 105                 110

Arg Leu Arg Ser Glu His Met Ala Asn Leu Ile Gly Cys Cys Cys Asp
        115                 120                 125

Asp Asn Glu Arg Leu Leu Val Ala Glu Tyr Met Pro Asn Gly Thr Leu
    130                 135                 140

Ala Lys His Leu Phe His Trp Glu Lys Arg Pro Met Lys Trp Glu Met
145                 150                 155                 160

Arg Leu Lys Val Ala Leu His Thr Ala Arg Ala Leu Glu Tyr Cys Asn
                165                 170                 175

Asp Lys Gly Ile Asp Leu Tyr His Asp Leu Asn Pro Tyr Arg Ile Met
            180                 185                 190

Phe Asp Lys Thr Gly Ile Pro Lys Leu Ser Cys Phe Gly Leu Met Lys
        195                 200                 205

Asn Ser His Glu Gly Lys Ile Tyr Ser Thr Asn Leu Ala Phe Ala Pro
    210                 215                 220

Pro Glu Tyr Leu Arg Leu Gly Thr Val Ile Ala Glu Ser Val Thr Phe
225                 230                 235                 240

Ser Phe Gly Thr Leu Leu Leu Asp Leu Met Ser Gly Arg His Ile Pro
                245                 250                 255
```

```
Pro Asn His Ala Leu Asp Leu Phe Arg Gly Lys Asn Tyr Leu Val Leu
            260                 265                 270

Met Asp Ser Ala Leu Asp Gly Gln Phe Ser Asp Glu Asp Arg Thr Glu
        275                 280                 285

Leu Ile His Val Ala Ser Arg Cys Phe Lys Thr Glu Pro Glu Glu Arg
    290                 295                 300

Pro Ser Ile Lys Phe Leu Lys Ala Thr Leu Ser Arg Leu Gln Lys Arg
305                 310                 315                 320

Ala Lys Leu Cys Pro Ile Asn Val Lys Arg Pro Met Ser Pro Pro Ser
                325                 330                 335

Lys Asn Leu Pro Glu Lys Thr Lys Pro Ala Thr Glu Ser Leu Lys Leu
            340                 345                 350

Thr Pro Phe Gly Asp Ala Cys Ser Arg Ala Asp Leu Ser Ser Ile His
        355                 360                 365

Glu Leu Leu Glu Lys Leu Gly Tyr Glu Glu Asp Asn Gly Val Gly Asn
    370                 375                 380

Glu Phe Ser Phe Gln Met Trp Thr Gly Glu Met Gln Glu Asn Met Asp
385                 390                 395                 400

Tyr Lys Lys His Gly Asp Ala Ala Phe Leu Ala Lys Asp Phe Asp Thr
                405                 410                 415

Ala Ile Glu Phe Tyr Thr Glu Phe Met Thr Gly Ala Pro Thr Val Ser
            420                 425                 430

Pro Thr Val Leu Ala Arg Arg Cys Leu Cys Tyr Leu Met Thr Glu Met
        435                 440                 445

Phe Ser Glu Ala Leu Ser Asp Ala Met Gln Ala Gln Val Ala Ser Pro
    450                 455                 460

Glu Trp Pro Ile Pro Leu Tyr Leu Gln Ala Ala Cys Leu Phe Lys Leu
465                 470                 475                 480

Glu Met Glu Ala Glu Ala Lys Glu Ala Leu Arg His Gly Ser Ala Leu
                485                 490                 495

Glu Ala Tyr


<210> SEQ ID NO 36
<211> LENGTH: 507
<212> TYPE: PRT
<213> ORGANISM: Arabidopsis thaliana

<400> SEQUENCE: 36

Met Gly Cys Cys Gln Ser Ser Phe Leu Lys Pro Ser Ser Leu His Asp
1               5                   10                  15

Lys Lys Ile Thr Ser Asp Asp Leu Ser Gly Arg Arg Gly Lys Gly Ala
            20                  25                  30

Lys Arg Gly Asn Arg His Arg His Ala Asn Ile Asn Glu Gly Arg Gly
        35                  40                  45

Trp His Phe Ser Asp Val Pro Asp Phe Ser Glu Phe Ser Ala Ser Val
    50                  55                  60

Leu Arg Asp Ala Thr Asn Asn Phe Asn Lys Asn Ala Val Val Ser Val
65                  70                  75                  80

Cys Ser Asp Gln Glu Pro Asn Leu Val Tyr Gln Gly Cys Ile Arg Ser
                85                  90                  95

Asp Lys Asp Lys Arg Leu Ile Ala Val Lys Lys Phe Ser Lys Thr Thr
            100                 105                 110

Trp Pro Asp Pro Lys Gln Phe Ala Thr Glu Ala Arg Ala Ile Gly Ser
        115                 120                 125
```

```
Leu Arg His Val Arg Leu Val Asn Leu Ile Gly Tyr Cys Cys Glu Gly
    130                 135                 140

Asp Glu Arg Leu Leu Val Ser Glu Tyr Met Pro Asn Glu Ser Leu Thr
145                 150                 155                 160

Lys His Leu Phe His Trp Glu Lys Gln Thr Met Glu Trp Ala Met Arg
                165                 170                 175

Leu Arg Val Ala Leu Tyr Val Ala Glu Ala Leu Glu Tyr Cys Arg Gln
            180                 185                 190

Ser Gly Leu Lys Leu Tyr His Asp Leu Asn Thr Cys Arg Val Leu Phe
        195                 200                 205

Asp Glu Asn Gly Ser Pro Arg Leu Ser Cys Phe Gly Trp Met Lys Asn
    210                 215                 220

Ser Lys Asp Gly Lys Asn Phe Ser Thr Asn Leu Ala Tyr Thr Pro Pro
225                 230                 235                 240

Glu Tyr Leu Arg Ser Gly Thr Leu Ile Pro Glu Ser Val Val Phe Ser
                245                 250                 255

Phe Gly Thr Phe Leu Leu Asp Leu Leu Ser Gly Lys His Ile Pro Pro
            260                 265                 270

Ser His Ala Val Gly Thr Ile Gln Lys Gln Asn Leu Asn Val Leu Met
        275                 280                 285

Asp Ser His Leu Glu Gly Asn Tyr Pro Glu Glu Asp Ala Ala Met Val
    290                 295                 300

Phe Asp Leu Ala Ser Lys Cys Leu His Asn Asn Pro Asn Glu Arg Pro
305                 310                 315                 320

Glu Ile Gly Asp Ile Ile Ser Val Ile Thr Thr Leu Gln Gln Lys Leu
                325                 330                 335

Asp Val Pro Ser Tyr Thr Met Leu Gly Ile Ser Lys Leu Glu Lys Leu
            340                 345                 350

Glu Met Glu His Pro Lys Ser Leu Ile Tyr Asp Ala Cys His Gln Met
        355                 360                 365

Asp Leu Ala Ala Leu His Gln Ile Leu Glu Ala Met Glu Tyr Lys Glu
    370                 375                 380

Asp Glu Val Thr Cys Glu Leu Ser Phe Gln Gln Trp Ala Gln Gln Ile
385                 390                 395                 400

Lys Asp Val Cys Asn Thr Arg Gln Gln Gly Asp Ser Ala Phe Arg Asn
                405                 410                 415

Lys His Phe Glu Ser Ala Ile Asp Lys Tyr Thr Gln Phe Ile Glu Ile
            420                 425                 430

Gly Ile Met Ile Ser Pro Thr Val Tyr Ala Arg Arg Ser Met Cys Tyr
        435                 440                 445

Leu Phe Cys Asp Gln Pro Asp Ala Ala Leu Arg Asp Ala Met Gln Ala
    450                 455                 460

Gln Cys Val Tyr Ser Asp Trp Pro Thr Ala Phe Tyr Leu Gln Ala Val
465                 470                 475                 480

Ala Leu Ser Lys Leu Asn Met Val Glu Asp Ser Ala Thr Met Leu Lys
                485                 490                 495

Glu Ala Leu Ile Leu Glu Asp Lys Arg Gly Ser
            500                 505
```

<210> SEQ ID NO 37
<211> LENGTH: 465
<212> TYPE: PRT
<213> ORGANISM: Arabidopsis thaliana

<400> SEQUENCE: 37

```
Met Gly Cys Cys Tyr Ser Leu Ser Ser Thr Val Asp Pro Val Gln Asp
1               5                   10                  15

His Thr Thr Asp Ala Ser Ser Glu Pro Arg Asn Gly Gly Gly Glu Asp
            20                  25                  30

Pro Pro Leu Thr Lys Phe Ser Phe Ser Ala Leu Lys Thr Ala Thr Asn
        35                  40                  45

His Phe Ser Pro Glu Asn Ile Val Ser Asp Gln Thr Ser Asp Val Val
    50                  55                  60

Phe Lys Gly Arg Leu Gln Asn Gly Gly Phe Val Ala Ile Lys Arg Phe
65                  70                  75                  80

Asn Asn Met Ala Trp Ser Asp Pro Lys Leu Phe Leu Glu Glu Ala Gln
                85                  90                  95

Arg Val Gly Lys Leu Arg His Lys Arg Leu Val Asn Leu Ile Gly Tyr
            100                 105                 110

Cys Cys Asp Gly Asp Lys Arg Phe Leu Val Ala Asp Phe Met Ala Asn
        115                 120                 125

Asp Thr Leu Ala Lys Arg Leu Phe Gln Arg Lys Tyr Gln Thr Met Asp
    130                 135                 140

Trp Ser Ile Arg Leu Arg Val Ala Tyr Phe Val Ala Glu Ala Leu Asp
145                 150                 155                 160

Tyr Cys Asn Thr Ala Gly Phe Ala Ser Tyr Asn Asn Leu Ser Ala Tyr
                165                 170                 175

Lys Val Leu Phe Asp Glu Asp Gly Asp Ala Cys Leu Ser Cys Phe Gly
            180                 185                 190

Leu Met Lys Glu Ile Asn Asn Asp Gln Ile Thr Thr Gly Ser Val Asn
        195                 200                 205

Pro Glu Asn Val Ile Tyr Arg Phe Gly Thr Val Leu Val Asn Leu Leu
    210                 215                 220

Ser Gly Lys Gln Ile Pro Pro Ser His Ala Pro Glu Met Ile His Arg
225                 230                 235                 240

Lys Asn Val Phe Lys Leu Met Asp Pro Tyr Leu Lys Gly Lys Phe Ser
                245                 250                 255

Ile Asp Glu Ala Asn Val Val Tyr Lys Leu Ala Ser Gln Cys Leu Lys
            260                 265                 270

Tyr Glu Gly Gln Glu Ser Pro Asn Thr Lys Glu Ile Val Ala Thr Leu
        275                 280                 285

Glu Thr Leu Gln Thr Arg Thr Glu Ala Pro Ser Tyr Glu Val Val Glu
    290                 295                 300

Met Thr Asn Gln Glu Lys Asp Ala Ser Ser Ser Ser Asn Leu Ser Pro
305                 310                 315                 320

Leu Gly Glu Ala Cys Leu Arg Met Asp Leu Ala Ser Ile His Ser Ile
                325                 330                 335

Leu Val Leu Ala Gly Tyr Asp Asp Asp Lys Asp Ile Ile Glu Leu Ser
            340                 345                 350

Phe Glu Glu Trp Ile Gln Glu Val Lys Glu Leu Gln Asp Val Arg Arg
        355                 360                 365

Asn Gly Asp Arg Ala Phe Val Glu Gln Asp Phe Lys Thr Ala Ile Ala
    370                 375                 380

Cys Tyr Ser Gln Phe Val Glu Glu Arg Ser Leu Val Tyr Pro Ser Val
385                 390                 395                 400

Tyr Ala Arg Arg Ser Leu Ser Tyr Leu Phe Cys Asp Glu Pro Glu Lys
                405                 410                 415

Ala Leu Leu Asp Gly Met His Ala Gln Gly Val Phe Pro Asp Trp Pro
            420                 425                 430
```

-continued

```
Thr Ala Phe Tyr Leu Gln Ser Val Ala Leu Ala Lys Leu Asp Met Asn
        435                 440                 445

Thr Asp Ser Ala Asp Thr Leu Lys Glu Ala Ala Leu Leu Glu Val Lys
    450                 455                 460

Lys
465
```

BRASSINOSTEROID REGULATED KINASES (BRKS) THAT MEDIATE BRASSINOSTEROID SIGNAL TRANSDUCTION AND USES THEREOF

RELATED APPLICATIONS

This application claims priority to U.S. Provisional Application No. 61/082,444, filed Jul. 21, 2008, which is hereby incorporated in its entirety.

GOVERNMENT SUPPORT

The work leading to this invention was supported by grants from the National Science Foundation (NSF 0724688), U.S. Department of Energy (DE-FG02-04ER15525), and NIH (R01GM066258). The government may have certain rights to the invention.

SEQUENCE LISTING SUBMISSION VIA EFS-WEB

A computer readable text file, entitled "056100-5074-US-SubstituteSequenceListing.txt," created on or about Dec. 1, 2011 with a file size of about 128 kb contains the sequence listing for this application and is hereby incorporated by reference in its entirety.

FIELD OF THE INVENTION

The present invention relates to the identification of a novel family of kinase proteins regulated by brassinosteroids.

BACKGROUND

Brassinosteroids

Brassinosteroids (BRs) are a group of naturally occurring steroidal plant hormones that are required for plant growth and development. The first identified BR, Brassinolide, was discovered in 1973, when it was shown that pollen extract from *Brassica napus* could promote stem elongation and cell division. There are few reports on the physiological effects of brassinosteroids in the growth and development of rice and other plants of the Gramineae family. Physiological research indicates that exogenous brassinosteroids alone, or in combination with auxin, enhance bending of the lamina joint in rice. The total yield of Brassinosteroids from 230 kg of *Brassica napus* pollen, however, was only 10 mg. Extract from the plant *Lychnis viscaria* contains a relatively high amount of BRs. *Lychnis viscaria* is said to increase the disease resistance of surrounding plants. In Germany, extract from the plant is allowed for use as a "plant strengthening substance." Since their initial discovery, over seventy BR compounds have been isolated from plants.

BRs have been shown to be involved in numerous plant processes: promotion of cell expansion and cell elongation (working with auxin); cell division and cell wall regeneration (the mechanism of which is still to be determined); promotion of vascular differentiation; pollen elongation for pollen tube formation; acceleration of senescence in dying tissue cultured cells; and providing protection during chilling and drought stress.

Treatment with low or high concentrations of brassinosteroids promotes or inhibits the growth of roots in rice, respectively (Radiet al. J. Crop Sci. 57, 191 198 (1988)). Brassinosteroids also promote the germination of rice seeds (Yamaguchi et al. *Stimulation of germination in aged rice seeds by pre-treatment with brassinolide*, in Proceeding of the fourteenth annual plant growth regulator society of America Meeting Honolulu, ed. Cooke A R), pp. 26 27 (1987)). The lamina joint of rice has been used for a sensitive bioassay of brassinosteroids (Maeda Physiol. Plant. 18, 813 827 (1965); Wada et al. Plant and Cell Physiol. 22, 323 325 (1981); Takeno et al. Plant Cell Physiol. 23, 1275 1281 (1982)), because of high sensitivity thereof to brassinosteroids. In etiolated wheat seedlings treatment with brassinolide or its derivative, castasterone, stimulates unrolling of the leaf blades (Wada et al. Agric. Biol. Chem. 49, 2249 2251 (1985)).

Brassinosteroids are recognized as a class of plant hormones through the combination of molecular genetics and researches on biosyntheses (Yokota Trends in Plant Sci., 2, 137 143 (1997)). Most of the C28-brassinosteroids are common vegetable sterols, and they are considered to be biosynthesized from campesterol, which has the same carbon side chain as that of brassinolide. The basic structure of BR is presented below.

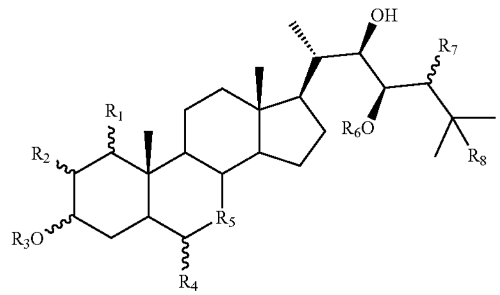

Although the sites for BR synthesis in plants have not, to date, been experimentally demonstrated, one well-supported hypothesis is that as BR biosynthetic and signal transduction genes are expressed in a wide range of plant organs, all tissues produce BRs. Since the chemistry of brassinosteroids was established, biological activities of these homologues have been extensively studied, and their notable actions on plant growth have been revealed, which include elongation of stalks, growth of pollen tubes, inclination of leaves, opening of leaves, suppression of roots, activation of proton pump (Mananda, Annu. Rev. Plant Physiol. Plant Mol. Biol. 39, 23 52 (1988)), acceleration of ethylene production (Schlagnhaufer et al., Physiol. Plant 61, 555 558 (1984)), differentiation of vessel elements (Iwasaki et al., Plant Cell Physiol., 32, pp. 1007 1014 (1991); Yamamoto et al. Plant Cell Physiol., 38, 980 983 (1997)), and cell extension (Azpiroz et al. Plant Cell, 10, 219 230 (1998)). Furthermore, mechanisms and regulations of physiological actions of brassinosteroids have been revealed by a variety of studies on their biosynthesis (Clouse, Plant J. 10, 18 (1996); Fujioka et al. Physiol. Plant 100, 710 715 (1997)).

Brassionsteroid Signaling

In the 1990s, it was discovered in *Arabidopsis* that BRs are essential plant hormones through analysis of mutant plants unable to naturally synthesize BRs. These *Arabidopsis* mutants which show characteristic dwarfism, e.g. dwf1: Feldman et al. Science 243, 1351 1354 (1989); dim: Takahashi et al. Genes Dev. 9, 97 107 (1995); and cbb1: Kauschmann et al. Plant J. 9, 701 703 (1996) and their corresponding structural photomorphogenesis and dwarfism are known (e.g. cpd: Szekeres et al. Cell, 85, 171 182 (1997)) and de-etiolation (det2: Li et al., Science 272, 398 401 (1996); Fujioka et al. Plant Cell 9, 1951 1962 (1997)). The morphologic changes are directly related to their deficiency in BR biosynthesis. BRs are also essential in other plants, as demonstrated with studies on a dwarf mutant of *Pisum sativum* (Nomura et al. Plant Physiol. 113, 31 37, 1997). In all these mutant plants, use of brassinolide will negate the severe dwarfism.

The mechanism by which BR can propagate its effects starts with a cell receptor to interact with a BR. Receptors may be located on the surface of a cell, or within the cell itself Cell-surface receptor kinases activate cellular signal transduction pathways upon perception of extracellular signals, thereby mediating cellular responses to the environment and to other cells. The *Arabidopsis* genome encodes over 400 receptor-like kinases (RLKs) (Shiu et al., *Plant Cell* 16, 1220 (May, 2004)). Some of these RLKs function in growth regulation and plant responses to hormonal and environmental signals. However, the molecular mechanism of RLK signaling to immediate downstream components remains poorly understood, as no RLK substrate that mediates signal transduction has been established in *Arabidopsis* (Johnson et al., *Curr Opin Plant Biol* 8, 648 (December, 2005)).

The use of Brassionsteroid-insensitive *Arabidopsis* mutants allowed for the identification of several components of Brassinosteroid signal transduction, including the leucine-rich-repeat (LRR) receptor-like kinases (RLK), brassinosteroid-insensitive 1 (BRI1) and BRI1-associated receptor-kinase (BAK1), the glycogen synthase kinase 3 (GSK3)-like kinase brassinosteroid-insensitive 2 (BIN2), the phosphatase bri1 suppressor 1 (BSU1), and two transcription factors brassinazole-resistant 1 (BZR1) and brassinazole resistant 2 (BZR2)/bri1-EMS-suppressor 1 (BES1). Meanwhile, it has been reported that genetic regulation of the brassinosteroid metabolism makes plants highly sensitive to brassinosteroids, and thus an effect of brassinosteroid administration is markedly enhanced (Neff et al. Proc. Natl. Acad. Sci., USA 96, 15316 23 (1999)).

Brassinosteroids bind to the extracellular domain of the receptor kinase BRI1 to activate a signal transduction cascade that regulates nuclear gene expression and plant development. Many components of the brassinosteroid signaling pathway have been identified and studied in detail. However, the substrate of BRI1 kinase that transduces the signal to downstream components remains unknown.

BRI1 is an RLK that functions as the major receptor for the steroid hormones brassinosteroids (Johnson et al., Curr Opin Plant Biol 8, 648 (December, 2005)). Brassinosteroids bind the extracellular domain of BRI1 to activate its kinase activity, initiating a signal transduction cascade that regulates nuclear gene expression and a wide range of developmental and physiological processes (FIG. 5) (Vert et al., Annu Rev Cell Dev Biol 21, 177 (2005)). Many components of the BR signaling pathway have been identified and much detail has been revealed about how BR activates BRI1 (Wang et al., Nature 410, 380 (Mar. 15, 2001); Kinoshita et al., Nature 433, 167 (Jan. 13, 2005); Wang et al., Plant Cell 17, 1685 (June, 2005); Wang et al., Science 313, 1118 (Aug. 25, 2006); Wang et al., Dev Cell 8, 855 (June, 2005)) and how phosphorylation by downstream GSK3-like kinase, BIN2, regulates the activity of the nuclear transcription factors that mediate BR-responsive gene expression (FIG. 5) (Vert et al., Annu Rev Cell Dev Biol 21, 177 (2005); Wang et al., Dev Cell 2, 505 (April, 2002); He et al., Science 307, 1634 (2005); Yin et al., Cell 120, 249 (Jan. 28, 2005); Vert et al., Nature 441, 96 (May 4, 2006); Gampala et al., Dev Cell 13, 177 (August, 2007)). However, no direct interaction has been observed between BRI1 and BIN2, and it remains unclear how BRI1 kinase at the plasma membrane transduce the signal to cytoplasmic components of the BR pathway (Gendron et al., Curr Opin Plant Biol 10, 436 (October 2007)). Thus, there is a need to identify the kinases that transduce the signal from the BRI1 receptor to BIN2.

SUMMARY OF THE INVENTION

The present invention is directed to the discovery of a novel family of kinases that are activated by the binding of brassinosteroid to the brassinosteroid plasma membrane receptor BIN1. This family of kinases is referred to as BRKs (brassinosteroid regulated kinases) or BRKs (brassinosteroid receptor signaling kinases) (also referred to as BSK or brassinosteroid signaling kinase). This novel family of kinases interacts with the BIN1 receptors at the plasma membrane and mediates the signaling from the receptor to gene expression. Proteomic studies of plasma membrane proteins led to the identification of three homologous BR-regulated kinases (BRK1, BRK2 and BRK3). The BRKs are phosphorylated by BRI1 in vitro and interact with BRI1 in vivo. Loss-of-function mutation of BRK3 greatly reduces plant's responsiveness to BRs, and overexpression of the BRKs activates downstream BR responses, including gene expression and cell elongation. These genetic and transgenic studies demonstrate that the BRKs represent a small family of kinases that activate BR signaling downstream of BRI1. These results demonstrate that BRKs are the substrates of BRI1 kinase that activate downstream BR signal transduction.

The present invention is based in part on the discovery of a novel family of kinases that are activated by the binding of brassinosteroid with the brassinosteroid plasma membrane receptor BIN1. The present invention provides methods of measuring and determining the signaling generated by brassinosteroids. The present invention also provides methods of modulating the BR signal transduction in a cell. The methods may comprise assaying the kinase activity of a BRK.

The present invention provides nucleic acid molecules encoding the BRK kinase proteins in plants and animals, such as mammals. The present invention provides a novel family of plant kinases involved in the signaling cascades induced by brassinosteroids. The present invention also provides for fusion proteins comprising BRKs. The present invention provides an isolated nucleic acid molecule comprising a sequence of nucleotides that encodes a brassinosteroid receptor regulated kinase (BRK), wherein the nucleic acid is not derived from *Arabidopsis thaliana*. The nucleic acid may encode another plant BRK. The present invention provides polypeptides encoded by the nucleic acids of the present invention. The isolated nucleic acid encoding a BRK may hybridize to SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, or SEQ ID NO: 23 under stringent conditions and wherein the nucleic acid does not encode a BRK derived from *Arabidopsis thaliana*. The isolated nucleic acid may have at least 60%, 70%, 80% 85%, 90%, 95%, or 99% sequence identity with SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, or SEQ ID NO: 23.

The isolated nucleic acid may encode a BRK polypeptide having an amino acid sequence having at least 80%, 85%, 90%, 95%, or 99% sequence identity with SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, or SEQ ID NO: 24.

The present invention provides an expression construct comprising a nucleic acid sequence encoding a BRK of the present invention operably linked to a promoter. The present invention also provides a host cell transformed with a recombinant nucleic acid molecule encoding a BRK of the present invention. The host cell may be a plant cell.

The present invention provides a sequence of nucleotides encoding a BRK comprising the peptide $X_1X_2$STNLA$X_3X_4$PPEYLR (SEQ ID NO: 25), wherein $X_1$ is either serine, arginine, or isoleucine, $X_2$ and $X_3$ are either tyrosine or phenylalanine, and $X_4$ is either threonine or alanine. The serine at amino acid position three may be phosphorylated. The serine at amino acid position three may be mutated to an alanine, a glutamate or an aspartate.

The present invention provides an immunogenic composition, comprising a recombinant nucleic acid molecule encoding a BRK, together with a pharmaceutically acceptable carrier.

The present invention provides methods for expressing a BRK of the present invention in a cell. The BRK may be a wild-type BRK. The method may comprise expressing mutant BRK proteins into a cell. The present invention provides a transgenic plant comprising a nucleic acid encoding a BRK.

The present invention provides methods for producing a BRK polypeptide, comprising introducing a nucleic acid encoding a BRK into a host cell and culturing the cell under conditions that allow expression of the BRK polypeptide. The nucleic acid may be operably linked to a promoter. The nucleic acid may be contained in an expression vector. The host cell may be a prokaryotic cell or a eukaryotic cell. The host cell may be a plant cell. The plant cell may be derived from *Arabidopsis*.

The present invention provides methods for modulating cellular processes of a plant cell comprising introducing a nucleic acid into the plant cell, wherein the nucleic acid encodes a BRK protein. The cellular process may be cell expansion, cell elongation, cell division, cell growth, protection of the cell during exposure to cold, protection of the cell during exposure to heat, protection of the cell during drought, protection of the cell from a pathogen, fertility/sterility of the cell, acceleration of senescence of the cell when it is dying, promotion of vascular differentiation, cell wall regeneration, or pollen elongation. The cellular process may be inhibited by the BRK as compared to wild-type BRK. The cellular process may be enhanced as compared to wild-type BRK. The nucleic acid may encode a mutant BRK that cannot function as a kinase. The kinase may be inactivated as a kinase by mutating a phosphorylated serine to an alanine residue. The nucleic acid may encode a constitutively active BRK. The method may further comprise contacting the cell with a brassinosteroid.

The present invention provides methods of inhibiting growth of a plant comprising introducing into a cell a ribonucleic acid that hybridizes under stringent conditions to a nucleic acid encoding a BRK polypeptide.

The present invention provides methods for producing a transgenic plant comprising introducing into a plant cell a nucleic acid encoding a BRK. The present invention also provides methods for producing a transgenic plant that has an endogenous BRK knocked-out, or that over-expresses a mutant BRK that cannot function as a kinase. The plant may exhibit modulated fertility. The plant may be a sterile male. The plant may exhibit modulated growth.

The present invention provides methods for identifying compounds that interact with BRK comprising incubating recombinant BRK with a test compound and a BRK antibody and detecting binding of the antibody to BRK, wherein inability of the antibody to bind BRK indicates the test compound interacts with BRK. The present invention provides methods for determining the effects of a test substrate on brassinosteroid signaling comprising assaying the kinase activity of BRKs. The present invention also discloses methods for identifying compounds, such as small molecules, that inhibit the kinase activity of BRKs.

The present invention also discloses methods for identifying the signaling cascade of BRKs. These methods may be achieved through use of in vitro and in vivo methods. The methods may be performed using in vitro or in vivo cellular systems.

The present invention provides methods for identifying proteins that interact with BRKs. The interaction may be specific to a non-phosphorylated state of a BRK. The interaction may be specific to a phosphorylated state of a BRK. The interacting protein may be a scaffold protein, a cofactor, or a substrate.

The present invention also provides for methods for identifying BRKs in different plant cells.

BRIEF DESCRIPTION OF THE DRAWINGS

FIG. 1A shows a 2-D DIGE image of plasma membrane proteins isolated from 7-day-old det2 seedlings treated for 2 hr with either 100 nM BL (labeled with Cy5, red) or mock solution (Cy3, green). FIG. 1B shows a zoom-in view of an area of panel A showing BR-induced (black arrows, red spots) and BR-repressed (white arrows, green spots) protein spots. The table summarizes the protein identity, number of unique peptides, and the percentage of protein sequence coverage of mass spectrometry data for the spots numbered in the upper panel. FIGS. 1C-1E show 2-dimensional gel immunoblotting analysis of BR-regulation of post-translational modification of BRK1 in det2 (C) and bri1-5 (D) background. Transgenic det2 or bri1-5 mutant seedlings expressing BRK1-YFP fusion protein were treated for 15 min with mock solution (−BL) or 100 nM BL (+BL). The proteins were separated by 2-DE and immunoblotted using anti-YFP antibody. FIG. 1E shows quantitation of relative spot intensity along the IEF dimension in panels C and D. FIG. 1F shows confocal microcopy images show localization of BRK1-YFP in hypocotyl cells of 3-day-old dark-grown transgenic det2 seedlings before (−BL) and 2 hr after treatment with 100 nM brassinolide (+BL). Scale bar, 10 μm.

FIGS. 2A and 2B show BRI1 phosphorylates serine230 of BRK1 in vitro. FIG. 2A shows autoradiography of in vitro kinase assays performed with wild type (BRI1 and BAK1) or kinase-dead mutant (mBRI1 and mBAK1) forms of the kinase domain of BRI1 and BAK1 as GST fusion proteins. FIG. 2B shows in vitro kinase assays of BRI1 phosphorylation of full-length BRK1, BRK1 with deletion of TPR domain (ΔTPR), and S230A mutant BRK1. FIG. 2C shows BiFC assay showing BRI1 interaction with BRK1. YFP fluorescence images of *N. benthamiana* leaf epidermal cells co-transformed with the indicated constructs. FIG. 2D shows co-immunoprecipitation of BRI1 with BRK1. *Arabidopsis* plants expressing BRK1-myc only (lanes 1 and 4) or co-expressing BRK1-myc and BRI1-GFP (lanes 2, 3, 5, 6) were treated with 100 nM brassinolide (BL+) or mock solution (BL−) for 30 min. Microsomal proteins (lanes 1 to 3) were immunprecipitated with anti-GFP antibodies (lanes 4 to 6), and the immunoblot was probed using anti-GFP antibodies or anti-myc antibodies.

FIG. 3A shows T-DNA insertion site of brk3-1 knockout mutant (T-DNA line SALK_096500). FIG. 3B shows RT-PCR analysis of BRK3 RNA expression in seedlings of wild type Columbia ecotype (Col) and the brk3-1 mutant, with UBC RNA as control. FIG. 3C shows Wild type (Col) and brk3-1 seedlings grown in the dark for 4 days on regular medium (−BRZ) or medium containing 1 μM brassinazole (+BRZ). The right panel shows average hypocotyl length of at least 25 seedlings. Error bars represent standard error. FIG. 3D shows the brk3-1 mutant showing reduced sensitivity to brassinolide (BL). Left panel shows representative seedlings of Col or brk3-1 grown in the absence (−BL) or presence (+BL) of 50 nM BL for 7 days under constant light. The right panel shows hypocotyl and root lengths (average of at least 60 seedlings) of wild type (Col) and brk3-1 seedlings grown on various concentrations of BL under continuous light. Error bars represent standard error.

FIG. 4C shows quantitative RT-PCR analysis of DWF4 RNA expression in plants represented in panel A. Error bars represent standard deviation. FIG. 4D shows overexpression of BRK3 partly suppresses the bri1-116 mutant. FIG. 4E shows overexpression of BRK3 cannot suppress the bin2-1 mutant. FIG. 4F shows a model of BR signal transduction. Components in the inactive and active states are shown. In the absence of BR (−BR), BRI1 associates with BRKs in an inactive state; BIN2 phosphorylates BZR1 and BZR2 to inhibit their DNA binding activity and promote their cytoplasmic retention by the 14-3-3 proteins. BR-binding (+BR) to BRI1 induces its dimerization with BAK1 and activation of BRI1 kinase, which phosphorylates BRKs. Phosphorylated BRKs dissociate from BRI1 and presumably inhibit BIN2 kinase and/or activate BSU1 phosphatase through yet unknown mechanisms, leading to dephosphorylation of BZR1 and BZR2, which regulate BR-responsive gene expression.

FIGS. 7A and B show an alignment of amino acid sequences of BRKs. Solid underlines show the putative kinase domain, and the dashed lines show the tetratricopeptide repeat (TPR) domain. The names of different BRKs are: BRK1 (At4g35230) (SEQ ID NO: 26), BRK2 (At5g46570) (SEQ ID NO: 27), BRK3 (At4g00710) (SEQ ID NO: 28), BRK4 (At1g01740) (SEQ ID NO: 29), BRK5 (At5g59010) (SEQ ID NO: 30), BRK6 (At3g54030) (SEQ ID NO: 31), BRK7 (At1g63500) (SEQ ID NO: 32), BRK8 (At5g41260) (SEQ ID NO: 33), BRK9 (At3g09240) (SEQ ID NO: 34), BRK10 (At5g01060) (SEQ ID NO: 35), BRK11 (At1g50990) (SEQ ID NO: 36), and BRK12 (At2g17090) (SEQ ID NO: 37).

DETAILED DESCRIPTION

General Description

Figure 1:
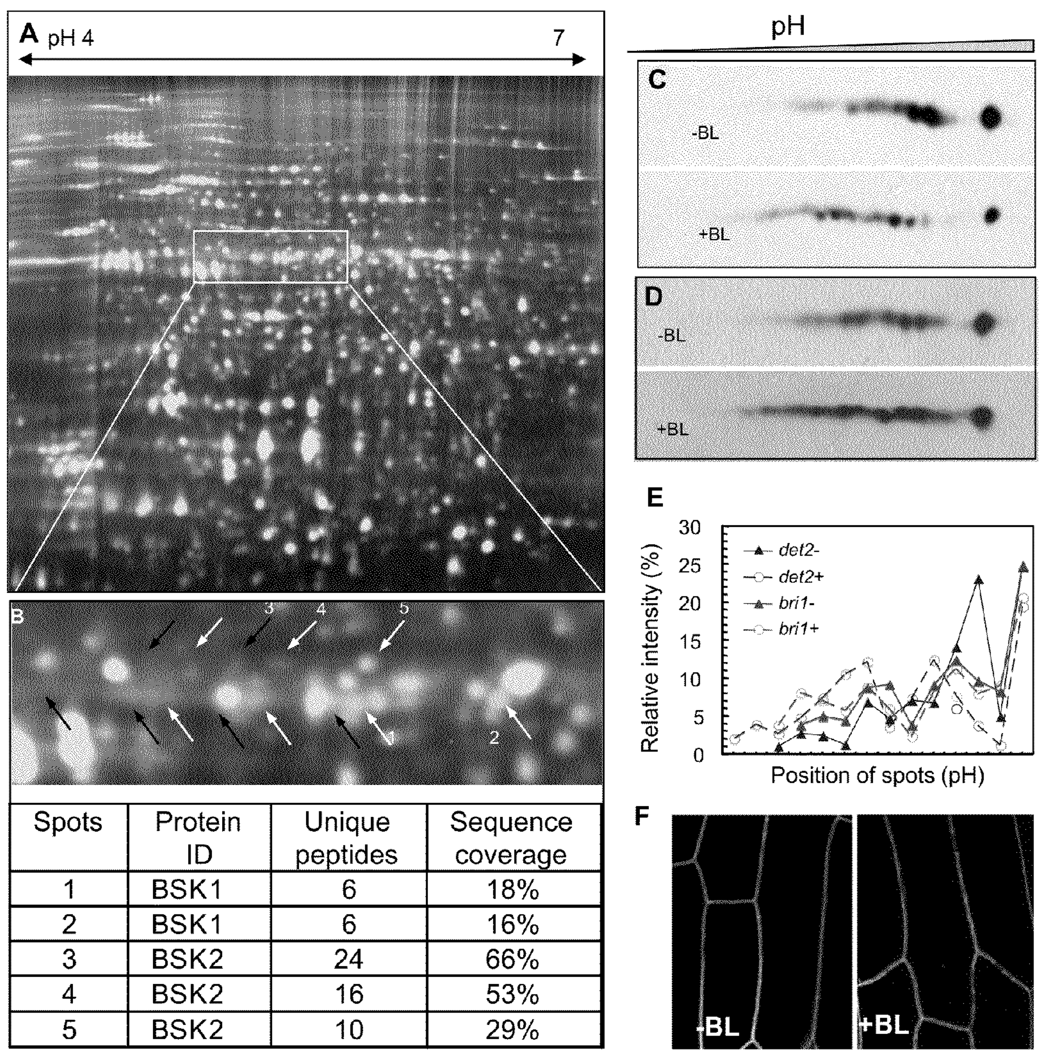
FIGS. 1A-1F show the identification of BRK1 and BRK2 as early BR regulated plasma membrane proteins.

Brassinosteroid, or BR, as used herein, refers to a plant growth regulator with a steroid backbone. It is known in the art that brassinosteroids have many functions, such as enhancement of plant growth and plant maturation, and induction of cold and heat resistance. Brassinolide is a type of brassinosteroid. Auxin is a plant growth regulator with an indole backbone that interacts with brassinosteroid signaling. It is known that some important roles of plant auxins include plant growth and differentiation, formation of flower buds and fruits, and responses to light and gravity.

The present invention is based in part on the discovery of a novel family of kinases that are activated by the binding of brassinosteroid with the brassinosteroid plasma membrane receptor BIN1. This family of kinases is referred to as BRKs (brassinosteroid regulated kinases) or BSKs (brassinosteroid signaling kinases). This novel family of kinases interacts with the BIN1 receptors at the plasma membrane and mediates the signaling from binding brassinosteroid to gene expression. Accordingly, as those skilled in the art will appreciate, much of the effects brassinosteroid produce on a plant cell and the overall plant are mediated through this novel kinase family. As used herein, BRK, or BSK, refers to a kinase activated by brassinosteroids. The effects of brassinosteroids on a plant cell are known in the art. According to the present invention, a BRK may be present or introduced in a plant cell. The plant cell may be derived from any plant. Polypeptides homologous to BRKs may be derived from any eukaryotic cell.

The family of kinases of the present invention comprise at least twelve members, numbered sequentially from BRK1 to BRK12 (or BSK1 to BSK12). BRK kinases are encoded by known cDNA sequences, as the entire genome of *Arabidopsis* was determined in 2001 and the majority of subsequent cDNAs have been cloned. While the cDNA were previously reported, expression of a functional protein and the function of the expressed protein was unknown. The present invention provides functional BRK or BSK polypeptides or functional equivalents or homologs thereof. A functional equivalent refers to a polypeptide capable of performing the same function, such as the same enzymatic function. For example and not as a limitation, a functional equivalent of a BRK will be able to phosphorylate the same substrate as wild-type BRK. As used herein, a "homolog" may include any polypeptide having a tertiary structure substantially identical to a polypeptide of the invention which also displays the functional properties of the polypeptides as described herein. A homolog of a BRK may be from another plant or from an animal.

The present invention also discloses identification of a phosphorylation site of the BRK proteins. BRKs 1 through 11 all contain the peptide of the sequence $X_1X_2$STNLA$X_3X_4$PPEYLR (SEQ ID NO: 25), wherein $X_1$ is either serine, arginine, or isoleucine, $X_2$ and $X_3$ are either tyrosine or phenylalanine, and $X_4$ is either threonine or alanine. The peptide may be obtained by tryptic digestion. In some aspects the present invention provides a BRK containing this peptide in which the serine at the third amino acid of this peptide is phosphorylated by the BRI1 kinase.

An antibody refers to an immunoglobulin molecule or a fragment of an immunoglobulin molecule having the ability to specifically bind to a particular antigen. Antibodies are well known to those of ordinary skill in the science of immunology. As used herein, the term "antibody" refers to not only full-length antibody molecules but also fragments of antibody molecules retaining antigen binding ability. Such fragments are also well known in the art and are regularly employed both in vitro and in vivo. In particular, as used herein, the term "antibody" means not only full-length immunoglobulin molecules but also antigen binding active fragments such as the well-known active fragments F(ab')2, Fab, Fv, and Fd.

As used herein, "subject" may include the recipient of the treatment to be practiced according to the invention. The subject may be a plant. The subject may be any animal, including a vertebrate. The animal may be a mammal. The subject mammal may be a human, a domestic livestock, a laboratory subject, or a pet animal.

As used herein with respect to proteins and polypeptides, the term "recombinant" may include proteins and/or polypeptides and/or peptides that are produced or derived by genetic engineering, for example by translation in a cell of non-native nucleic acid or that are assembled by artificial means or mechanisms.

As used herein with respect to polypeptides and proteins, the term "isolated" may include a polypeptide or nucleic acid that, by the hand of man, exists apart from its native environment and is therefore not a product of nature. For example, an isolated polypeptide may exist in a purified form or may exist in a non-native environment such as, for example, a recombinant host cell.

The term "cDNA" refers to a DNA molecule which can be prepared by reverse transcription from a mature, spliced, mRNA molecule obtained from a cell, preferably a eukaryotic cell. cDNA lacks intron sequences that are usually present in the corresponding genomic DNA. The initial, primary RNA transcript is a precursor to mRNA which is processed through a series of steps before appearing as mature spliced mRNA. These steps include the removal of intron sequences by a process called splicing. cDNA derived from mRNA lacks, therefore, intron sequences.

As used herein, the term "analog" may include any polypeptide having an amino acid sequence substantially identical to a polypeptide, or peptide, of the invention, in which one or more residues have been conservatively substituted with a functionally similar residue, and further which displays substantially identical functional aspects of the polypeptides as described herein. Examples of conservative substitutions include substitution of one non-polar (hydrophobic) residue for another (e.g. isoleucine, valine, leucine or methionine) for another, substitution of one polar (hydrophilic) residue for another (e.g. between arginine and lysine, between glutamine and asparagine, between glycine and serine), substitution of one basic residue for another (e.g. lysine, arginine or histidine), or substitution of one acidic residue for another (e.g aspartic acid or glutamic acid).

As used herein, "pharmaceutically acceptable carrier" may include any material which, when combined with an active ingredient, allows the ingredient to retain biological activity and is non-reactive with the subject's immune system. Examples may include, but are not limited to, standard pharmaceutical carriers such as a phosphate buffered saline (PBS) solution, water, emulsions, and various types of wetting agents.

As used herein, "fusion" may refer to nucleic acids and polypeptides that comprise sequences that are not found naturally associated with each other in the order or context in which they are placed according to the present invention. A fusion nucleic acid or polypeptide does not necessarily comprise the natural sequence of the nucleic acid or polypeptide in its entirety. Fusion proteins have two or more segments joined together through normal peptide bonds. Fusion nucleic acids have two or more segments joined together through normal phosphodiester bonds.

BRK Nucleic Acids

The present invention relates to nucleic acid molecules encoding the BRK kinase proteins. Nucleic acids include DNA, RNA, mRNA, cDNA, single-stranded (ss) DNA, ssRNA, dsRNA (double stranded), and genomic DNA. The cDNA nucleotides that encode for the endogenous BRK proteins in *Arabidopsis* have previously been identified and are referred under the following *Arabidopsis* Gene numbers: BRK1 At4g35320; BRK2 At5g46570; BRK3 At4g00710; BRK4 At1g01740; BRK5 At5g59010; BRK6 At3g54030; BRK7 At1g63500; BRK8 At5g41260; BRK9 At3g09240; BRK10 At5g01060; BRK11 At1g50990; and BRK12 At2g17090. The present invention also provides nucleic acids encoding BRKs from plants that are not *Arabidopsis*.

BRK proteins and homologs thereof in other plant cells may be identified and utilized. The brassinosteroid receptor has been identified in numerous species of plant. Accordingly, the BRK family of proteins have homologs in other species of plant. By way of example, Tables 1, 2, and 3, illustrate the homology between the coding region of *Arabidopsis* BRK proteins and the coding region of *Vitis vinifera*, *Glycine max*, and *Oryza sativa* are shown, as well as the kinase domains and the TPR domains.

TABLE 1

| Full length protein sequence alignment | | |
|---|---|---|
| Genebank accession number | Species | Identities to BRK1 (At4g35230) |
| CAO47470 | *Vitis vinifera* | 83% |
| CAO62016 | *Vitis vinifera* | 83% |
| Genebank accession number | Species | Identities to BRK2 (At5g46570) |
| CAO63419 | *Vitis vinifera* | 84% |
| AAP55105 | *Oryza sativa* | 82% |
| Genebank accession number | Species | Identities to BRK3 (At4g00710) |
| CAO39581 | *Vitis vinifera* | 82% |
| CAO62818 | *Vitis vinifera* | 79% |
| Genebank accession number | Species | Identities to BRK5 (At5g59010) |
| CAO21539 | *Vitis vinifera* | 84% |
| CAO15747 | *Vitis vinifera* | 81% |
| AAX61123 | *Glycine max* | 79% |

TABLE 2

| Kinase domain plus TPR domain sequence alignment | | |
|---|---|---|
| Genebank accession number | Species | Identities to BRK1 (At4g35230), Aa (81-512) |
| CAO47470 | *Vitis vinifera* | 90% |
| CAO62016 | *Vitis vinifera* | 89% |
| ABF93827 | *Oryza sativa* | 82% |
| ABB47948 | *Oryza sativa* | 79% |
| Genebank accession number | Species | Identities to BRK2 (At5g46570), AA (81-489) |
| CAO63419 | *Vitis vinifera* | 88% |
| AAP55105 | *Oryza sativa* | 85% |
| Genebank accession number | Species | Identities to BRK3 (At4g00710), Aa (61-489) |
| CAO39581 | *Vitis vinifera* | 84% |
| CAO62818 | *Vitis vinifera* | 83% |
| Genebank accession number | Species | Identities to BRK5 (At5g59010) Aa (61-489) |
| CAO21539 | *Vitis vinifera* | 87% |
| CAO15747 | *Vitis vinifera* | 84% |
| AAX61123 | *Glycine max* | 82% |

TABLE 3

| Kinase domain sequence alignment | | |
|---|---|---|
| Genebank accession number | Species | Identities to BRK1 (At4g35230), Aa (81-320) |
| CAO47470 | *Vitis vinifera* | 92% |
| CAO62016 | *Vitis vinifera* | 92% |
| ABF93827 | *Oryza sativa* | 87% |
| ABB47948 | *Oryza sativa* | 79% |

TABLE 3-continued

| Kinase domain sequence alignment | | |
|---|---|---|
| Genebank accession number | Species | Identities to BRK2 (At5g46570), AA (81-320) |
| CAO63419 | *Vitis vinifera* | 88% |
| AAP55105 | *Oryza sativa* | 85% |
| Genebank accession number | Species | Identities to BRK3 (At4g00710), Aa (61-320) |
| CAO39581 | *Vitis vinifera* | 87% |
| CAO62818 | *Vitis vinifera* | 86% |
| CAJ86160 | *Oryza sativa* | 85% |
| BAF16222 | *Oryza sativa* | 85% |
| CAO15747 | *Vitis vinifera* | 85% |
| CAO21539 | *Vitis vinifera* | 84% |
| CAE03448 | *Oryza sativa* | 80% |
| AAX61123 | *Glycine max* | 82% |
| AAX61122 | *Glycine max* | 82% |
| Genebank accession number | Species | Identities to BRK5 (At5g59010) Aa (61-320) |
| CAO21539 | *Vitis vinifera* | 90% |
| CAO15747 | *Vitis vinifera* | 88% |
| CAO26818 | *Vitis vinifera* | 83% |
| CAO39581 | *Vitis vinifera* | 83% |
| AAX61123 | *Glycine max* | 86% |
| AAX61122 | *Glycine max* | 86% |
| CAJ86160 | *Oryza sativa* | 80% |

The present invention provides for nucleic acid sequences that encode a BRK kinase or fragments thereof in other plants. The present invention also provides nucleic acid sequences encoding BRK or fragments thereof from animals, such as mammals. Examples of mammals include, but are not limited to canines, felines, mouse, pig, human, rat, hamster, gerbil, dolphin, whale, seal, cow, sheep, marsupials, and bats. In some instances, the nucleic acids comprise sequences that encode the kinase domain, or mutants thereof. The kinase domain of the BRK may also be mutated. The cDNAs encoding the BRK proteins are set forth in SEQ ID NOs: 1, 3, 5, 7, 9, 11, 13, 15, 17, 19, 21, and 23. In one embodiment, the nucleic acids of the present invention have at least about 50% identity with one of these sequences, at least about 60%, at least about 70%, at least about 80%, at least about 90%, at least about 95%, at least about 98%, at least about 99%, or at least about 99.5%. The present invention provides nucleic acids encoding BRKs or fragments thereof comprising a functionally active kinase domain.

A preparation of a polynucleotide encoding a BRK kinase or fragment thereof may be a substantially pure polynucleotide that is free of other extraneous or unwanted nucleotides and in a form suitable for use within genetically engineered protein production systems. The term "substantially pure polynucleotide" is synonymous with the term "isolated polynucleotide" or "polynucleotide in isolated form." The polynucleotides may be of genomic, cDNA, RNA, semisynthetic, synthetic origin, recombinant, or any combinations thereof. Thus, a substantially pure polynucleotide contains at most about 10%, at most about 8%, at most about 6%, at most about 5%, at most about 4%, at most about 3%, at most about 2%, at most about 1%, or at most about 0.5% by weight of other polynucleotide material with which it is natively or recombinantly associated. A substantially pure polynucleotide may, however, include naturally occurring 5' and 3' untranslated regions, such as promoters and terminators. The substantially pure polynucleotide may be at least about 90% pure, at least about 92% pure, at least about 94% pure, at least about 95% pure, at least about 96% pure, at least about 97% pure, at least about 98% pure, at least about 99%, or at least about 99.5% pure by weight. The polynucleotides of the present invention may be in a substantially pure form. The polynucleotides disclosed herein may be in "essentially pure form", i.e., that the polynucleotide preparation is essentially free of other polynucleotide material with which it is natively or recombinantly associated.

A subsequence refers to a nucleotide sequence having one or more nucleotides deleted from the 5' and/or 3' end of the full-length coding sequence or a homologous sequence thereof, wherein the subsequence encodes a polypeptide fragment having kinase activity. By way of example, a nucleotide sequence encoding the kinase domain of a BRK is a subsequence.

The present invention provides nucleic acid construct comprising a nucleic acid molecule encoding a BRK or fragment thereof, either single- or double-stranded, which is isolated from a naturally occurring gene or which is modified to contain segments of nucleic acids in a manner that would not otherwise exist in nature. The present invention also discloses an expression cassette containing the nucleic acid encoding BRK and control sequences required for expression of BRK.

Control sequences include all components which are necessary or advantageous for the expression of a polynucleotide encoding a BRK protein of fragment thereof of the present invention. Control sequences are operably linked to the nucleic acid encoding BRK. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

It will be appreciated by those skilled in the art that DNA sequence polymorphisms that lead to changes in the amino acid sequences of the BRK kinase protein may exist within a population. An allele is one of a group of genes that occur alternatively at a given genetic locus. A gene or a recombinant gene refers to nucleic acid molecules comprising an open reading frame encoding a kinase protein. An allelic variant denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene. Such natural allelic variations can typically result in 1-5% variance in the nucleotide sequence of the kinase gene. Any and all such nucleotide variations and resulting amino acid polymorphisms or variations in a kinase sequence that are the result of natural allelic variation and that do not alter the functional activity of kinase proteins are intended to be within the scope of the invention.

Moreover, nucleic acid molecules encoding BRK proteins from plant species (kinase homologs), which have a nucleotide sequence differing from that of the kinase sequence disclosed herein, are intended to be within the scope of the invention. Also within the scope of the invention are nucleic acid molecules encoding BRK homologs in animals, such as mammals. Nucleic acid molecules corresponding to natural allelic variants and homologs of the BRK cDNA can be isolated based on their identity to the kinase nucleic acid disclosed herein using the cDNA, or a portion thereof, as a hybridization probe according to standard hybridization techniques under stringent hybridization conditions as disclosed below.

The present invention also provides for nucleic acids that encode fragments of BRK. The fragments may comprise about 20, 25, 20, 35, 40, 45, 50, 55, 60, 65, 70, 75, 80, 85, 90, 95, 100, 110, 120, 130, 140, 150, 175, 200, 225, 250, 275, 300, 350, 400, 450, 500, 550, 600, 650, 700, 750, 800, 850, 900, 1000, 1100, 1200, 1300, 1400, 1500, 1600, 1700, 1800, 1900, 2000, 2100, 2200, 2300, 2400, or 2500 nucleotides in length. The fragments may encode the kinase domain of a BRK.

In addition to naturally-occurring allelic variants of the BRK sequence, the skilled artisan will further appreciate that changes can be introduced by mutation into the nucleotide sequences of the invention thereby leading to changes in the amino acid sequence of the encoded BRK kinase protein, without altering the biological activity of the BRK protein. Mutations can be introduced by standard techniques, such as site-directed mutagenesis and PCR-mediated mutagenesis. Such variant nucleotide sequences are also encompassed by the present invention.

Alternatively, variant BRK kinase nucleotide sequences can be made by introducing mutations randomly along all or part of the kinase coding sequence, such as by saturation mutagenesis, and the resultant mutants can be screened for kinase biological activity to identify mutants that retain functional activity, such as kinase activity. Following mutagenesis, the encoded protein can be expressed recombinantly, and the activity of the protein can be determined using standard assay techniques.

The present invention includes the polynucleotide sequences encoding BRK from various plant and eukaryotes, such as mammals, as well as fragments and variants thereof. The BRK nucleotide sequences of the invention, and fragments and variants thereof, can be used as probes and/or primers to identify and/or clone BRK homologs in other cell types, e.g., from other tissues, as well as kinase homologs from other plants or eukaryotes. Such probes can be used to detect transcripts or genomic sequences encoding the same or identical proteins. These probes can be used as part of a diagnostic test kit for identifying cells or tissues that misexpress a BRK kinase protein, e.g. detecting kinase mRNA levels or determining whether a genomic kinase gene has been mutated or deleted.

In this manner, methods such as PCR, hybridization, and the like can be used to identify such sequences having substantial identity to the BRK sequences of the present invention. See, e.g. Sambrook et al. Molecular Cloning: Laboratory Manual (2d ed., Cold Spring Harbor Laboratory Press, Plainview, N.Y.) (1989) and Innis et al. PCR Protocols: A Guide to Methods and Applications (Academic Press, NY) (1990). Kinase nucleotide sequences isolated based on their sequence identity to the kinase nucleotide sequences set forth herein or to fragments and variants thereof are encompassed by the present invention.

In a hybridization method, all or part of a known BRK kinase nucleotide sequence can be used to screen cDNA or genomic libraries. Hybridization may be to a sense strand or to an antisense strand for a nucleic acid encoding a BRK. A sense strand is a nucleic acid that in the direction of 5' to 3' encodes a BRK polypeptide or fragment thereof. An antisense strand is complementary to a strand encoding a BRK or fragment thereof. Methods for construction of such cDNA and genomic libraries are generally known in the art and are disclosed in Sambrook et al. Molecular Cloning: Laboratory Manual (2d ed., Cold Spring Harbor Laboratory Press, Plainview, N.Y.) (1989). The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known kinase nucleotide sequences disclosed herein. Degenerate primers designed on the basis of conserved nucleotides or amino acid residues in a known kinase nucleotide sequence or encoded amino acid sequence can additionally be used. The probe typically comprises a region of nucleotide sequence that hybridizes under stringent conditions to at least about 12, preferably about 25, more preferably about 50, 75, 100, 125, 150, 175, 200, 250, 300, 350, or 400 consecutive nucleotides of a kinase nucleotide sequence of the invention or a fragment or variant thereof. Preparation of probes for hybridization is generally known in the art and is disclosed in Sambrook et al. Molecular Cloning: Laboratory Manual (2d ed., Cold Spring Harbor Laboratory Press, Plainview, N.Y.) (1989), herein incorporated by reference.

As used herein, the term "hybridizes under stringent conditions" is intended to describe conditions for hybridization and washing under which nucleotide sequences typically remain hybridized to each other. Such stringent conditions are known to those skilled in the art and can be found in Current Protocols in Molecular Biology (John Wiley & Sons, NY (1989)), 6.3.1-6.3.6. An example of stringent hybridization conditions is hybridization in 6× sodium chloride/sodium citrate (SSC) at about 45° C., followed by one or more washes in 0.2×SSC, 0.1% SDS at 50° C. Another example of stringent hybridization conditions is hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Stringent hybridization conditions may also be hybridization in 6× sodium chloride/sodium citrate (SSC) at about 45° C., followed by one or more washes in 0.2×SSC, 0.1% SDS at 65° C. Moreover, stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2×SSC, 1% SDS at 65° C. An isolated nucleic acid molecule that hybridizes under stringent conditions to a kinase sequence of the invention may correspond to a naturally-occurring nucleic acid molecule.

The isolated BRK nucleic acid molecules of the invention also encompasses homologous DNA sequences identified and isolated from other cells and/or organisms by hybridization with entire or partial sequences obtained from a kinase nucleotide sequence disclosed herein or variants and fragments thereof.

The present invention also encompasses antisense nucleic acid molecules, i.e., molecules that are complementary to a sense nucleic acid encoding a BRK protein, e.g., complementary to the coding strand of a double-stranded cDNA molecule, or complementary to an mRNA sequence. Accordingly, an antisense nucleic acid can hydrogen bond to a sense nucleic acid. The antisense nucleic acid can be complementary to an entire kinase coding strand, or to only a portion thereof, e.g., all or part of the protein coding region (or open reading frame). An antisense nucleic acid molecule can be antisense to a noncoding region of the coding strand of a nucleotide sequence encoding a kinase protein. The noncoding regions are the 5' and 3' sequences that flank the coding region and are not translated into amino acids.

Given the coding-strand sequences encoding a kinase protein disclosed herein, antisense nucleic acids of the invention can be designed according to the rules of Watson and Crick base pairing. The antisense nucleic acid molecule can be complementary to the entire coding region of BRK kinase mRNA, but more preferably is an oligonucleotide that is antisense to only a portion of the coding or noncoding region of kinase mRNA. An antisense nucleic acid of the invention can be constructed using chemical synthesis and enzymatic ligation procedures known in the art. For example, an antisense nucleic acid (e.g., an antisense oligonucleotide) can be chemically synthesized using naturally-occurring nucleotides or variously modified nucleotides designed to increase the biological stability of the molecules or to increase the physical stability of the duplex formed between the antisense and sense nucleic acids, including, but not limited to, for example, phosphorothioate derivatives and acridine substituted nucleotides. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest). The antisense nucleic acid molecules of the invention are typically administered to a cell or generated in situ such that they hybridize with or bind to cellular mRNA and/or genomic DNA encoding a BRK kinase protein to thereby inhibit expression of the protein, e.g., by inhibiting transcription and/or translation.

Those skilled in the art will also appreciate that nucleic acids encoding BRK proteins or the complementary strands thereto can be used to inhibit expression of the BRK proteins. In some embodiments, antisense or double stranded RNA (dsRNA) may be introduced to a cell to inhibit expression of the BRK. Furthermore, the use of small inhibiting RNA (siRNA) will inhibit expression of a BRK protein. Such techniques are known in the art, see, e.g. Fire et al. Nature 391: 806-811 (1998) and Mello et al. Nature 431: 338-342 (2004).

The invention also provides nucleic acid molecules that form triple helical structures. For example, BRK kinase gene expression can be inhibited by targeting nucleotide sequences complementary to the regulatory region of the kinase protein (e.g. the kinase promoter and/or enhancers) to form triple helical structures that prevent transcription of the kinase gene in target cells. See generally Helene Anticancer Drug Des. 6(6), 569 (1991); Helene Ann. N.Y. Acad. Sci. 660, 27 (1992); and Maher Bioassays 14(12), 807 (1992).

In other embodiments, the nucleic acid molecules of the invention can be modified at the base moiety, sugar moiety, or phosphate backbone to improve, e.g. the stability, hybridization, or solubility of the molecule. For example, the deoxyribose phosphate backbone of the nucleic acids encoding BRK proteins or fragments thereof can be modified to generate peptide nucleic acids (see Hyrup et al. Bioorganic & Medicinal Chemistry 4, 5 (1996)). As used herein, the term "peptide nucleic acids" or "PNAs" refer to nucleic acid mimics, e.g. DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid-phase peptide synthesis protocols which are known in the art. Furthermore, PNAs of a BRK kinase molecule can be further modified, e.g., to enhance their stability, specificity, or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described Finn et al. Nucleic Acids Res. 24(17): 3357-63 (1996); Mag et al. Nucleic Acids Res. 17:5973 (1989); and Peterser et al. Bioorganic Med. Chem. Lett. 5:1119 (1975).

BRK Proteins

The present invention provides a novel family of plant kinases involved in the signaling cascades induced by brassinosteroids. Kinases can have a specificity for (i.e., a specificity to phosphorylate) serine/threonine residues, tyrosine residues, or both serine/threonine and tyrosine residues, e.g. the dual-specificity kinases. Kinases are proteins that have a catalytic kinase domain of about 200-400 amino acid residues in length, or about 200-300 amino acid residues in length, or about 250-300 amino acid residues in length, which includes 5-20, or 5-15, or 11 highly conserved motifs or subdomains separated by sequences of amino acids with reduced or minimal conservation. Specificity of a kinase for phosphorylation of either tyrosine or serine/threonine can be predicted by the sequence of the subdomains, most notably VIb and VIII, in which different residues are conserved in each class (as described in, for example, Hanks et al. Science 241, 42-52 (1988), the contents of which are incorporated herein by reference). The BRK proteins may be regulated by brassionsteroid receptor kinases, or other receptor kinases, or chimeras thereof.

The present invention provides twelve isolated BRK proteins, numbered sequentially BRK1 through BRK12. The amino acid sequence of the BRK kinases may be derived from *Arabidopsis*, for example *Arabidopsis thaliana*. The present invention also provides BRKs identified from plants that are not *Arabidopsis thaliana*. The present invention also provides BRKs from animals, such as mammals. Examples of mammals include, but are not limited to canines, felines, mouse, pig, human, rat, hamster, gerbil, dolphin, whale, seal, cow, sheep, marsupials, and bats.

Kinases play a role in the signaling pathways associated with cellular growth. For example, protein kinases are involved in the regulation of signal transmission from cellular receptors, e.g. growth-factor receptors, entry of cells into mitosis, and the regulation of cytoskeleton function, e.g., actin bundling. In addition to a kinase function, BRK or fragments thereof may function as a scaffold protein. The ability to function as a scaffold may be regulated by the phosphorylation status of the BRK. The ability to function as a scaffold may be independent of the kinase activity of the BRK or fragment thereof.

Assays for measuring kinase activity are well known in the art depending on the particular kinase. Specific assay protocols are available in standard sources known to the ordinarily skilled artisan. See, e.g., "Kinases" in Ausubel et al., eds. Current Protocols in Molecular Biology 3 (1994-1998) and references cited therein.

Accordingly, some embodiments of the invention feature isolated BRK kinase proteins and polypeptides having a kinase protein activity. As used interchangeably herein, "kinase protein activity", "biological activity of a kinase protein", or "functional activity of a kinase protein" refers to an activity exerted by a kinase protein, polypeptide, or nucleic acid molecule on a kinase-responsive cell as determined in vivo, or in vitro, according to standard assay techniques. A kinase activity can be a direct activity, such as autophosphorylation or an association with or an enzymatic activity on a second protein. In a preferred embodiment, kinase activity includes at least one or more of the following activities: (1) modulating (stimulating and/or enhancing or inhibiting) cellular proliferation, growth and/or metabolism (e.g. in those cells in which the sequence is expressed); (2) the regulation of transmission of signals from cellular receptors, e.g., growth factor receptors; (3) the modulation of the entry of cells into mitosis; (4) the modulation of cellular differentiation; (5) the modulation of cell death; and (6) the regulation of cytoskeleton function.

The present invention also provides for polypeptide fragments of BRK. The fragments may comprise about 10, 15, 20, 25, 20, 35, 40, 45, 50, 55, 60, 65, 70, 75, 80, 85, 90, 95, 100, 110, 120, 130, 140, 150, 175, 200, 225, 250, 275, 300, 350, 400, 450, 500, 550, or 600 amino acids in length. The fragments may encode the kinase domain of BRK.

An isolated or purified BRK kinase protein, or biologically active portion thereof, is substantially free of other cellular material, or culture medium when produced by recombinant techniques, or substantially free of chemical precursors or other chemicals when chemically synthesized.

A BRK kinase protein that is substantially free of cellular material includes preparations of BRK kinase protein having less than about 30%, 20%, 10%, or 5% (by dry weight) of non-kinase protein (also referred to herein as a contaminating protein). When the BRK protein or active portion thereof is recombinantly produced, the culture medium may comprise less than about 30%, 20%, 10%, or 5% of the volume of the protein preparation. When a BRK protein is produced by chemical synthesis, the preparations may have less than about 30%, 20%, 10%, or 5% (by dry weight) of chemical precursors or non-kinase chemicals.

The polypeptides of the present invention have at least about 20%, at least about 40%, at least about 50%, at least about 60%, at least about 70%, at least about 80%, at least about 90%, at least about 95%, or at least about 100% of the kinase activity of the polypeptide consisting of the amino acid sequence shown in SEQ ID NOs: 2, 4, 6, 8, 10, 12,14, 16, 18, 20, 22, or 24.

An isolated polypeptide refers to a BRK polypeptide which is at least about 20% pure, at least about 40% pure, at least about 60% pure, at least about 80% pure, at least about 90% pure, or at least about 95% pure, as determined by SDS-PAGE. A substantially pure polypeptide is synonymous with an isolated polypeptide. An isolated polypeptide refers to a polypeptide preparation which contains at most about 10%, at most about 8%, at most about 6%, at most about 5%, at most about 4%, at most about 3%, at most about 2%, at most about 1%, or at most about 0.5% by weight of other polypeptide material with which it is natively or recombinantly associated. An isolated BRK polypeptide may be at least about 92% pure, at least about 94% pure, at least about 95% pure, at least about 96% pure, at least about 96% pure, at least about 97% pure, at least about 98% pure, at least about 99%, at least about 99.5% pure, or at least about 100% pure by weight of the total polypeptide material present in the preparation.

The BRK polypeptides of the present invention may be in a substantially pure form. In particular, the polypeptides are in essentially pure form, i.e., that the polypeptide preparation is essentially free of other polypeptide material with which it is natively or recombinantly associated. This can be accomplished, for example, by preparing the polypeptide by means of well-known recombinant methods or by classical purification methods.

The relatedness of two amino acid sequences or two nucleotide sequences is described by the term "identity." For purposes of the present invention, the degree of identity between two amino acid sequences is determined by the Clustal method (Higgins, CABIOS 5: 151-153 (1989)). The present invention provides for polypeptides having at least about 60%, 70%, 80%, 85%, 90%, 95%, 98%, 99%, or 100% identity with BRK. The polypeptides may have at least having at least about 60%, 70%, 80%, 85%, 90%, 95%, 98%, 99%, or 100% identity with a BRK amino acid sequence as set forth in SEQ ID NOs: 2, 4, 6, 8, 10, 12,14, 16, 18, 20, 22, or 24

The term "active fragment" as used herein refers to a BRK polypeptide having one or more amino acids deleted from the amino and/or carboxyl terminus of a full-length BRK kinase polypeptide or a homologous sequence thereof, wherein the fragment retains kinase activity.

The present invention also provides for mutations in the BRK proteins that do not affect the activity of the kinase. For example, conservative amino acid substitutions may be made at one or more predicted, nonessential amino acid residues such that the BRK mutant retains its functional activity. A nonessential amino acid residue is a residue that can be altered from the wild-type sequence of a kinase protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g. alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues or for amino acid residues residing within a conserved protein domain, such as the serine/threonine protein kinase domain of the disclosed clones, where such residues are essential for protein activity.

Fusion Proteins

The present invention also provides for fusion proteins comprising BRKs. In some embodiments, the present invention provides a fusion polypeptide comprising a BRK polypeptide or active fragment thereof fused to additional polypeptides. There may be one, two, three, four, or more additional polypeptides fused to the BRK polypeptide. The additional polypeptides may be fused toward the amino terminus of the BRK polypeptide. The additional polypeptides may be fused toward the carboxyl terminus of the BRK polypeptide. The additional polypeptides may also flank the BRK polypeptide.

The additional polypeptides may comprise an epitope. The additional polypeptides may also comprise an affinity tag. By way of example, fusion of a polypeptide comprising an epitope and/or an affinity tag to the BRK polypeptide may aid purification and/or identification of the protein. By way of example, the additional polypeptide may be a His-tag, a myc-tag, an S-peptide tag, a MBP tag (maltose binding protein), a GST tag (glutathione S-transferase), a FLAG tag, a thioredoxin tag, a GFP tag (green fluorescent protein), a BCCP (biotin carboxyl carrier protein), a calmodulin tag, a Strep tag, an HSV-epitope tag, a V5-epitole tag, and a CBP tag. The use of such epitopes and affinity tags is known to those skilled in the art.

In further embodiments, the additional polypeptides may provide sites for cleavage of the protein. As an example, a polypeptide may be cleaved by hydrolysis of the peptide bond. In some embodiments, the cleavage is performed by a protease enzyme. In some embodiments cleavage occurs in a cell. In other embodiments, cleavage occurs through artificial manipulation and/or artificial introduction of a cleaving enzyme. By way of example, protease enzymes may include aspartic proteases, serine proteases, metalloproteases and cysteine proteases.

The fusion polypeptides of the present invention may be prepared by any known techniques. For example, the polypeptides may be expressed through genetic engineering. By way of example, the translation of recombinant DNA. The polypeptides may also be prepared synthetically. By way of example, the polypeptide may be synthesized using the solid-phase synthetic technique initially described by Merrifield (J. Am. Chem. Soc. 85:2149-2154.), which is incorporated herein by reference. Other polypeptide synthesis techniques may be found, for example, Kent et al. Synthetic Peptides in Biology and Medicine, eds. Alitalo, Partanen, and Vakeri, Elsevier Science Publishers, pp. 295-358 (1985).

Fusion proteins and peptides of the invention may be prepared by any available means, including recombinant expression of the desired protein or peptide in eukaryotic or prokaryotic host cells (see U.S. Pat. No. 5,696,238). Methods for producing proteins or polypeptides of the invention for purification may employ conventional molecular biology, microbiology, and recombinant DNA techniques within the ordinary skill level of the art. Such techniques are explained fully in the literature. See, e.g., Maniatis et al., Molecular Cloning: A Laboratory Manual, 2d ed. Cold Spring Harbor Laboratory Press; Glover (1989), (1985) DNA Cloning: A Practical Approach, Vols. 1-4, IRL Press; Gait, (1984) Oligonucleotide Synthesis: A Practical Approach, IRL Press; Hames & Higgins, (1985) Nucleic Acid Hybridisation: A Practical Approach, IRL Press; Freshney, (1992) Animal Cell Culture: A Practical Approach, IRL Press; Perbal, (1984) A Practical Guide To Molecular Cloning, Wiley.

Transformed and Transfected Cells

The present invention provides for transforming a plant cell with an expression vectors having a linear or circular nucleic acid molecule comprising a polynucleotide encoding a BRK protein operably linked to additional nucleotides that provide for its expression.

The present invention also provides host cells of any cell type that is susceptible to transformation, transfection, transduction, and the like with a nucleic acid construct comprising a polynucleotide encoding a BRK.

The word "plant" refers to any plant, particularly to agronomically useful plants (e.g., seed plants), and "plant cell" is a structural and physiological unit of the plant, which comprises a cell wall but may also refer to a protoplast. The plant cell may be in the form of an isolated single cell or a cultured cell, or as a part of higher organized unit such as, for example, a plant tissue, or a plant organ differentiated into a structure that is present at any stage of a plant's development. Such structures include one or more plant organs including, but are not limited to, fruit, shoot, stem, leaf, flower petal, etc. The term "plant" includes whole plants, shoot vegetative organs/structures (e.g. leaves, stems and tubers), roots, flowers and floral organs/structures (e.g. bracts, sepals, petals, stamens, carpels, anthers and ovules), seeds (including embryo, endosperm, and seed coat) and fruits (the mature ovary), plant tissues (e.g. vascular tissue, ground tissue, and the like) and cells (e.g. guard cells, egg cells, trichomes and the like), and progeny of same.

The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous. Included within the scope of the invention are all genera and species of higher and lower plants of the plant kingdom. Included are furthermore the mature plants, seed, shoots and seedlings, and parts, propagation material (for example seeds and fruit) and cultures, for example cell cultures, derived therefrom. Also included are plants and plant materials of the following plant families: Amaranthaceae, Brassicaceae, Carophyllaceae, Chenopodiaceae, Compositae, Cucurbitaceae, Labiatae, Leguminosae, Papilionoideae, Liliaceae, Linaceae, Malvaceae, Rosaceae, Saxifragaceae, Scrophulariaceae, Solanaceae, and Tetragoniaceae.

Annual, perennial, monocotyledonous and dicotyledonous plants are preferred host organisms for the generation of transgenic plants. The use of the recombination system, or method according to the invention is furthermore advantageous in all ornamental plants, forestry, fruit, or ornamental trees, flowers, cut flowers, shrubs or turf. Said plant may include, but shall not be limited to, bryophytes such as, for example, Hepaticae (hepaticas) and Musci (mosses); pteridophytes such as ferns, horsetail and clubmosses; gymnosperms such as conifers, cycads, *ginkgo* and Gnetaeae; algae such as Chlorophyceae, Phaeophpyceae, Rhodophyceae, Myxophyceae, Xanthophyceae, Bacillariophyceae (diatoms) and Euglenophyceae.

Plants for the purposes of the invention may comprise the families of the Rosaceae such as rose, Ericaceae such as rhododendrons and azaleas, Euphorbiaceae such as poinsettias and croton, Caryophyllaceae such as pinks, Solanaceae such as petunias, Gesneriaceae such as African violet, Balsaminaceae such as touch-me-not, Orchidaceae such as orchids, Iridaceae such as gladioli, iris, freesia and crocus, Compositae such as marigold, Geraniaceae such as geraniums, Liliaceae such as Drachaena, Moraceae such as ficus, Araceae such as philodendron and many others.

The transgenic plants according to the invention are furthermore selected in particular from among dicotyledonous crop plants such as, for example, from the families of the Leguminosae such as pea, alfalfa and soybean; the family of the Umbelliferae, particularly the genus *Daucus* (very particularly the species *carota* (carrot)) and *Apium* (very particularly the species *graveolens* var. *dulce* (celery)) and many others; the family of the Solanaceae, particularly the genus *Lycopersicon*, very particularly the species *esculentum* (tomato) and the genus *Solanum*, very particularly the species *tuberosum* (potato) and *melongena* (aubergine), tobacco and many others; and the genus *Capsicum*, very particularly the species *annum* (pepper) and many others; the family of the Leguminosae, particularly the genus *Glycine*, very particularly the species *max* (soybean) and many others; and the family of the Cruciferae, particularly the genus *Brassica*, very particularly the species *napus* (oilseed rape), *campestris* (beet), *oleracea* cv Tastie (cabbage), *oleracea* cv Snowball Y (cauliflower) and *oleracea* cv Emperor (broccoli); and the genus *Arabidopsis*, such as the species *thaliana* and many others; the family of the Compositae, such as the genus *Lactuca*, and the species *sativa* (lettuce) and many others.

The transgenic plants according to the invention may be selected among monocotyledonous crop plants, such as, for example, cereals such as wheat, barley, sorghum and millet, rye, triticale, maize, rice or oats, and sugarcane. Also included are trees such as apple, pear, quince, plum, cherry, peach, nectarine, apricot, papaya, mango, and other woody species including coniferous and deciduous trees such as poplar, pine, sequoia, cedar, oak, etc. Also included are *Arabidopsis thaliana, Nicotiana tabacum*, oilseed rape, soybean, corn (maize), wheat, linseed, potato and tagetes.

The present invention provides for the plasmid(s) or vector(s) containing nucleic acids encoding BRK introduced into a host cell, a plant cell, or a transgenic plant. The plant may be *Arabidopsis thaliana* or selected from the group consisting of wheat, corn, peanut cotton, oat, and soybean plant.

Methods, vectors, and compositions for transforming plants and plant cells in accordance with the invention are well-known to those skilled in the art, and are not particularly limited. For a descriptive example see Karimi et al., TRENDS in Plant Science, 7: 193-195, 2002, incorporated herein by reference.

Chromosomally-integrated refers to the integration of a foreign gene or DNA construct into the host DNA by covalent bonds. Where genes are not "chromosomally integrated" they may be "stably expressed" or "transiently expressed." Transient expression of a gene refers to the expression of a gene that is not integrated into the host chromosome but functions independently, either as part of an autonomously replicating plasmid or expression cassette, for example, or as part of another biological system such as a virus. Stable expression refers to expression of a gene that is not integrated into the host chromosome, but the gene replicates and divides with the division of the cell so that daughter cells of the host cell also contain the plasmid containing the gene.

An altered plant trait may be any phenotypic or genotypic change in a transgenic plant relative to the wild-type or non-transgenic plant host. The present invention provides for transgenic plants wherein the BRK signaling is modulated. The transgenic plant may have BRK proteins knocked out, or the transgenic plant may over express a mutant BRK that cannot function properly as a kinase. Such a mutation may, for example, occur at a phosphorylation site or an ATP binding domain of the kinase domain, such as at an active lysine. The transgenic plant may express wild-type BRK. The transgenic plant may exhibit modulated growth. The transgenic plant may demonstrate increased or improved growth. The transgenic plant may demonstrate reduced or diminished growth. The transgenic plant may exhibit modulated reproductive function. The transgenic plant may exhibit improved fertility. The transgenic plant may be sterile.

Nucleic acid encoding BRK or a fragment thereof may be transformed into the genome of a host cell by transformation, resulting in genetically stable inheritance. Host cells containing the transformed nucleic acid fragments are referred to as "transgenic" cells, and organisms comprising transgenic cells are referred to as "transgenic organisms." Examples of methods of transformation of plants and plant cells include *Agrobacterium*-mediated transformation and particle bombardment technology (e.g. U.S. Pat. No. 4,945,050). Whole plants may be regenerated from transgenic cells by methods well known to the skilled artisan.

Host organisms containing the transformed nucleic acid fragments are referred to as "transgenic" organisms. Examples of methods of plant transformation include *Agrobacterium*-mediated transformation (De Blaere et al. Meth. Enzymol. 143, 277 (1987)) and particle-accelerated or "gene gun" transformation technology (Klein et al. Nature 327, 70-73 (1987); U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct may be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

"Transformed", "transgenic", and "recombinant" refer to a host organism such as a bacterium or a plant into which a heterologous nucleic acid molecule has been introduced. The nucleic acid molecule can be stably integrated into the genome generally known in the art. For example, "transformed," "transformant," and "transgenic" plants or calli have been through the transformation process and contain a foreign gene integrated into their chromosome. The term "untransformed" refers to normal plants that have not been through the transformation process.

Transformation of plant cells is known in the art. By way of example, plant cells may be derived from *Arabidopsis, Heliothis zea, Vitis vinifera, Brassica, Maize, Glycine, Lycopersicon, Nicotinium*, corn, tomato plant, wheat, rice, oat, barley, hops, lettuce, green pepper, rose bush, palm tree, oak tree, pine tree, maple tree, evergreen tree, cedar tree, peach tree, apple tree, orange tree, grapefruit tree, nectarine tree, grape vine, apricot tree, cherry tree, lemon tree, lime tree, pepper, onion, potato, suede, parsnip, and grass.

A "primary transformant" and "To generation" refer to transgenic plants that are of the same genetic generation as the tissue which was initially transformed (i.e., not having gone through meiosis and fertilization since transformation). "Secondary" transformants and the $T_1$, $T_2$, $T_3$, etc. generations refer to transgenic plants derived from primary transformants through one or more meiotic and fertilization cycles. They may be derived by self-fertilization of primary or secondary transformants or crosses of primary or secondary transformants with other transformed or untransformed plants.

The present invention also includes modified BRK proteins and BRK nucleotides, such as chemical modifications. The amino acid sequence of BRK may be modified by substituting, deleting and/or inserting one or more amino acids, as well as replacements of one or more amino acid side chains. The nucleic acid may be modified by substituting, deleting and/or inserting one or more nucleotides. The nucleic acid may be genetically modified.

Higher eukaryotic cell cultures may also be used to express the kinases of the present invention, whether from vertebrate or invertebrate cells, including insects, and the procedures of propagation thereof are known. See, for example, Kruse and Patterson (1973) Tissue Culture, Academic Press. Suitable host cells for expressing the polypeptides of the present invention in higher eukaryotes include: 293 (human embryonic kidney) (ATCC CRL-1573); 293F (Invitrogen, Carlsbad Calif.); 293T and derivative 293T/17(293tsA1609neo and derivative ATCC CRL-11268) (human embryonic kidney transformed by SV40 T antigen); COS-7 (monkey kidney CVI line transformed by SV40) (ATCC CRL1651); BHK (baby hamster kidney cells) (ATCC CRL10); CHO (Chinese hamster ovary cells); mouse Sertoli cells; CVI (monkey kidney cells) (ATCC CCL70); VERO76 (African green monkey kidney cells) (ATCC CRL1587); HeLa (human cervical carcinoma cells) (ATCC CCL2); MDCK (canine kidney cells) (ATCC CCL34); BRL3A (buffalo rat liver cells) (ATCC CRL1442); W138 (human lung cells) (ATCC CCL75); HepG2 (human liver cells) (HB8065); and MMT 060652 (mouse mammary tumor) (ATCC CCL51).

Kinase Mutants

The present invention provides phosphorylated forms of BRKs. As those skilled in the art will recognize, phosphorylation is a significant event for a kinase. The phosphorylation of a BRK kinase activates the protein which mediates the brassinosteroid signal transduction process. The phosphorylation of a kinase is also significant as it can lead to disassociation with certain proteins, such as co-factors or scaffolds, and can also initiate interactions with other proteins such as substrates, co-factors or phosphatases.

BRKs 1 through 11 all contain a peptide available by tryptic digestion of the full-length BRK comprising the sequence $X_1X_2$STNLA$X_3X_4$PPEYLR (SEQ ID NO: 25), wherein $X_1$ is either serine, arginine, or isoleucine, $X_2$ and $X_3$ are either tyrosine or phenylalanine, and $X_4$ is either threonine or alanine.

The present invention provides phosphorylated BRKs having serine residues phosphorylated. The serine at the third amino acid of SEQ ID NO: 25 may be phosphorylated. This serine residue corresponds to position 230 of SEQ ID NO: 2. This serine residue may be mutated to alter its kinase activity (see, e.g. FIG. 7).

Inhibition or over-stimulation of the activity of kinases involved in signaling pathways associated with cellular growth can lead to perturbed cellular growth, which can in turn lead to cellular growth related-disorders. As used herein, a "cellular growth-related disorder" includes a disorder, disease, or condition characterized by a deregulation, e.g., an upregulation or a downregulation, of cellular growth. Cellular growth deregulation may be due to a deregulation of cellular proliferation, cell cycle progression, cellular differentiation and/or cellular hypertrophy.

In some embodiments, the present invention also provides BRK mutants having a mutated kinase domain. The kinase activity of the mutated BRK may be inhibited. In some instances, the site of phosphorylation of a BRK that is required for the BRK to in-turn phosphorylate its substrate is mutated. Those skilled in the art will appreciate that typically serine, threonine tyrosine and/or histidine residues are phosphorylated. In other embodiments, the mutated phosphorylation site prevents the kinase domain from functioning properly, such as, for example, binding ATP or transferring the terminal phosphate to a substrate. The mutated site of phosphorylation may be responsible for at least about 25% of the kinase activity, at least about 50%, at least about 60%, at least about 70%, at least about 80%, at least about 85%, at least about 90%, at least about 95%, or about 100% of the kinase activity. The serine at amino acid 230 may be mutated to a non-polar amino acid, such as alanine.

In other embodiments, the kinase domain is mutated so that the BRK kinase is no longer able to bind ATP. Those skilled in the art will appreciate that most kinases rely on a lysine residue in the ATP binding region of the kinase domain to aid in the transfer the terminal phospho group from ATP to its substrate. By way of example, the active lysine is at amino acid position 104 of BRK1, 84 of BRK2, 86 of BRK3, 84 of BRK4, 83 of BRK5, 84 of BRK6, 87 of BRK7, 87 of BRK8, 77 of BRK9, 91 of BRK10, 106 of BRK11, and 78 of BRK12 as defined by SEQ ID NOs: 2, 4, 6, 8, 10, 12, 14, 16, 18, 20, 22, and 24, respectively (see e.g. FIG. 7 and the BRK family alignment). The active lysine residue may be mutated to another amino acid, such as, but not limited to, a methionine or alanine.

Also, it is possible to mutate a kinase to mimic its phosphorylated state. In preferred instances, the residues that are phosphorylated on a BRK protein are mutated to acidic amino acids. For example, a serine, threonine, tyrosine, or histidine can be mutated to a glutamate, aspartate, or homologs thereof to mimic the added phospho-group. A site of phosphorylation that is mutated to an acidic residue may provide a constitutively active BRK. The mutated site of phosphorylation may be responsible for at least 25% of the kinase activity, at least 50%, at least 60%, at least 70%, at least 80%, at least 90%, at least 95%, or 100% of the kinase activity. The serine at amino acid 230 of BRK1, or the corresponding position of the other BRK family members, may be mutated to an acidic amino acid, such as glutamate or aspartate.

The activity of the BRK kinases may be affected through the alteration of the amino acid sequence comprising the kinase, more particularly the kinase domain. In some embodiments, Immunogenic Compositions The present invention provides immunogenic compositions comprising the BRK polypeptide(s) and fragments thereof. The immunogenic compounds may be a BRK polypeptide, a fragment thereof or a nucleic acid encoding a BRK or a fragment thereof. The BRK or fragment thereof may comprise a phosphorylated amino acid. Use of a phosphorylated BRK or BRK fragment may be of use to provide antibodies specific to a phosphorylated BRK, as opposed to a non-phosphorylated BRK.

Immunogenic compositions are compositions that are capable of generating an immune response. Immune responses may be directed to certain immunodominant regions of the composition. Association of the BRK polypeptide with its receptor may present a novel epitope or novel epitopes for antibody binding. In one embodiment of the present invention, the phosphorylated form of a BRK presents a novel epitope. In other instances, the phosphorylation of the serine at amino acid 230 provides a particular immunogenic epitope. The use of the polypeptide $X_1X_2$STNLA$X_3X_4$PPEYLR (SEQ ID NO: 25), wherein $X_1$ is either serine, arginine, or isoleucine, $X_2$ and $X_3$ are either tyrosine or phenylalanine, and $X_4$ is either threonine or alanine, may be another polypeptide fragment used to generate antibodies.

The present invention provides for administration of an immunogenic composition comprising a BRK polypeptide to a subject. In some embodiments, the immunogenic composition comprising an oligomer wherein the oligomer comprises nucleic acids encoding a BRK polypeptide. In some embodiments of the present invention, the immunogenic composition provides a highly potent and rapid antibody response. In other embodiments, the immunogenic compositions of the present invention provide cross-reactive neutralizing antibodies.

The present invention also provides immunogenic compositions comprising fusion proteins which can be administered to a subject in need thereof.

Adjuvants are well known in the art and include aluminum salts (alum), Complete Freund's Adjuvant (CFA), Incomplete Freund's Adjuvant (IFA), Muramyl dipeptide (MDP), synthetic analogues of MDP,N-acetylmuramyl-L-alanyl-D-isoglutamyl-L-alanine-2-[1,2-dipalmitoyl-s-glycero-3-(hydroxyphosphoryloxy)]ethylamide (MTP-PE) and compositions containing a metabolizable oil and an emulsifying agent, wherein the oil and emulsifying agent are present in the form of an oil-in-water emulsion having oil droplets substantially all of which are less than one micron in diameter (see EP 0399843).

The fusion polypeptide of the BRK immunogenic composition is typically an isolated and purified protein. The protein is preferably purified to at least about 95% purity, at least about 98% purity, or at least about 99% purity. Methods of purification that retain the conformation of the protein are known in the art. The purified protein may be present in a pharmaceutical composition with a pharmaceutically acceptable carrier, diluent, excipient or stabilizer present.

The formulation of BRK immunogenic compositions of the invention will employ an effective amount of the BRK protein or polypeptide antigen. That is, there will be included an amount of antigen which, in combination with the adjuvant, will cause the subject to produce a specific and sufficient immunological response. When used as an immunogenic composition, the formulation will contain an amount of antigen which, in combination with the adjuvant, will cause the subject to produce specific antibodies which may be used for diagnostic or therapeutic purposes. In some instances, the BRK immunogenic composition is phosphorylated to produce antibodies specific for the phosphorylated form of BRK.

The BRK immunogenic compositions are administered in any conventional manner which will introduce the composition into the animal, usually by injection. For oral administration the immunogenic composition can be administered in a form similar to those used for the oral administration of other proteinaceous materials. The precise amounts and formulations for use in either prevention or therapy can vary depending on the circumstances of the inherent purity and activity of the antigen, any additional ingredients or carriers, the method of administration and the like.

By way of non-limiting illustration, the dosages administered will typically be, with respect to the BRK polypeptide antigen, a minimum of about 0.1 mg/dose, more typically a minimum of about 1 mg/dose, and often a minimum of about 10 mg/dose. The maximum dosages are typically not as critical. Usually, however, the dosage will be no more than 500 mg/dose, often no more than 250 mg/dose. These dosages can be suspended in any appropriate pharmaceutical vehicle or carrier in sufficient volume to carry the dosage. Generally, the final volume, including carriers, adjuvants, and the like, typically will be at least 0.1 ml, more typically at least about 0.2 ml. The upper limit is governed by the practicality of the amount to be administered, generally no more than about 0.5 ml to about 1.0 ml.

In an alternative format, immunogenic compositions may be prepared as vaccine vectors which express the fusion polypeptides of the invention in the host animal. Any available vaccine vector may be used, including live Venezuelan Equine Encephalitis virus (see U.S. Pat. No. 5,643,576), poliovirus (see U.S. Pat. No. 5,639,649), pox virus (see U.S. Pat. No. 5,770,211) and vaccina virus (see U.S. Pat. Nos. 4,603,112 and 5,762,938). Alternatively, naked nucleic acid encoding a protein or peptide of the invention may be administered directly to effect expression of the antigen (see U.S. Pat. No. 5,739,118).

Methods of Use

The present invention provides methods of using a BRK protein and nucleic acids encoding a BRK. A BRK protein may be expressed in a cell, or a nucleic acid encoding a BRK may be introduced into a cell. A BRK protein may be contacted with cellular extract obtained from a cell. A cell may be treated prior to the introduction of BRK. A cell may be treated prior to preparing cellular extract from the cell. Cellular extract may be treated prior to incubation with a BRK. BRK may be purified from a cell or cellular extract. BRK may be isolated or purified through the use of a known epitope, such as a cloned epitope, or through the use of an antibody that binds the BRK. BRK may be further assayed for kinase activity, such as through the use of ATP and/or radiolabelled ATP.

Those skilled in the art will appreciate that a control may be used to determine or verify results. A control may serve as a point of comparison to measure effects an agent may have on BRK and/or BRK activity. A control may be a non-transfected cell or extract derived therefrom. A control may be a non-treated cell, or extract derived therefrom. A control may be a wild-type BRK. A control may be an endogenous BRK. A control may be a mutant BRK, such as a BRK with a mutated kinase domain, so that kinase activity is decreased or inhibited. A control may be a known substrate. A control may be a known agonist for BRK activity, such as an upstream kinase protein, or a brassinosteroid.

The present invention provides methods of measuring and determining the signaling generated by brassionsteroids, comprising assaying the kinase activity of a BRK. The present invention also provides methods of affecting the brassinosteroid signaling in a cell and thus altering the growth of a cell or plant. The methods of the present invention may comprise overexpressing a BRK protein in a host cell, for example a host cell derived from a plant. The methods of the present invention may comprise reducing the expression or activity of a BRK protein in a host cell or plant. Protein expression can be reduced by methods such as RNAi, antisense, or microRNA. Activity of a BRK can be reduced or increased by chemicals or genetic manipulations.

BRK activity may be reduced by an antagonist, such as antibodies or other agents that bind to it.

Those skilled in the art will appreciate that over-expression of a kinase does not automatically lead to enhanced or exaggerated signal cascades, as other rate-limiting enzymes may force a bottle-neck in the signaling cascade. The over-expression of BRKs will, at least, allow for increased activation of downstream BR responses, including cell elongation and growth, as demonstrated in the present invention.

In some instances, the methods of the present invention comprise expressing a wild-type BRK into a cell. In other embodiments, the methods comprise expressing kinase mutant BRK proteins into a cell.

Figure 5:
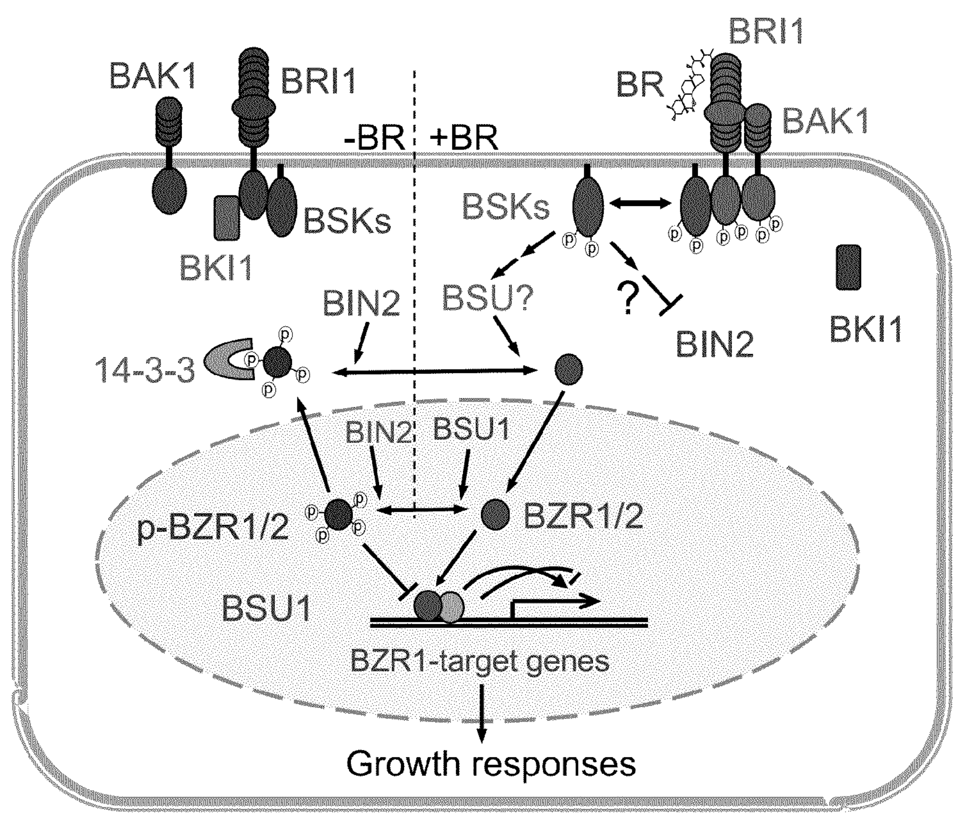
FIG. 5 shows a model of the BR signal transduction pathway. Components in active states and inactive states are shown. Arrows show positive action, and bar ends show inhibitory action. In the absence of BR (−BR, left side), both BRI1 and BAK1 are inactive; BKI1 binds BRI1 and inhibits its interaction with BAK1; BIN2 phosphorylates BZR1 and BZR2 (also named BES1) (BZR1/2). Phosphorylated BZR1 and BZR2 (p-BZR1/2) cannot bind DNA and are retained in the cytoplasm by the 14-3-3 proteins. In the presence of BR (+BR, right side), BR-binding to the extracellular domain of BRI1 activates BRI1 kinase by inducing dimerization and inter-phosphorylation with BAK1 and dissociation of BKI1. Activation of BRI1 and BAK1 kinases leads to dephosphorylation and activation of BZR1 and BZR2, presumably through activation of the BSU1 phosphatase or inhibition of BIN2. How the receptor kinases regulate the downstream components has remained an outstanding question. The present invention shows that BRKs are the substrates of BRI1 kinase that transduce the signal from BRI1 to downstream components. BRKs associate with BRI1 in the absence of BR, and are phosphorylated by BRI1 and released from the BRI1 complex upon BR activation of BRI1 kinase. How BRKs regulate downstream components such as BSU1 or BIN2 remains to be further studied.

Those skilled in the art will appreciate that kinase activity and signaling cascades affected by BRKs can be determined in multiple ways. For example, BRKs can be purified from a cell, such as by immunoprecipitation or affinity-resin binding, followed by a kinase assay. By way of further example, reporter genes, such as renilla-luciferase, coupled to a promoter region for a known gene regulated by brassinosteroids, such as BZR1 (see, e.g. FIG. 5). Activation of BRKs or kinase activity upon BRKs can be detected through the use of immunoblotting, or western blotting. Shifts in phosphorylation can also be detected by other means such as 2D-electrophoresis (see examples below). Phosphorylation may be detected with the use of labeled ATP, wherein the terminal phosphate group is labeled, such as with a radio-isotope (e.g. $^{32}$P-γ-ATP) or a fluorescent tag. The genes affected by BRK signaling may be determined through comparison of wild-type and a mutant BRK through such means as cDNA microarray.

The present invention also provides methods for identifying the signaling cascade of BRK kinases, such as through identifying changes in phosphorylation or changes in gene transcription. Proteins or changes to proteins may be identified through comparison to a known control, such as a negative control. BRKs may be used as bait in incubation with cellular extracts to allow associate proteins to bind and then be identified. BRK may be used as a bait through production of a recombinant BRK attached to a solid support or immunoprecipitation of a BRK coupled to a solid support or medium, such as a Sepharose bead. BRK may be immunoprecipitated from a treated and a non-treated cell (and/or a non-BRK transfected cell where appropriate) and then each compared to each other. Those skilled in the art will appreciate that over-expression of the kinases described herein will allow for identification of downstream proteins, such as substrates and genes, affected by over-expression of BRK kinases. By way of example, affected proteins may be identified and/or confirmed by Southern blot, Edman degradation, bioluminescence imaging, northern blot, SDS-PAGE, DNA sequencing, liquid chromatography, high performance liquid chromatography, fractioning chromatography, immunoblotting, tandem-mass spectrometry, or matrix-assisted laser desorption/ionization-time of flight mass spectrometry. Those skilled in the art will also recognize that over-expression of mutated forms of the BRK kinases will allow for identification and comparison with wild-type BRKs to identify other proteins in the BRK signaling cascades. In some instances, over-expression of kinase inactive mutants will provide for determination as to whether a particular protein is directly affected by BRK kinase activity. Those skilled in the art will also recognize that different proteins interact with kinases when they are phosphorylated than when they are not. For example, phosphorylation of a BRK may allow a substrate to bind. Mutation of a BRK substrate, such as at its phosphorylation site, may further prolong the interaction between the proteins. Other proteins, such as phosphatases may further interact with BRKs following their phosphorylation by BRI1. Some proteins contain motifs or domains that bind to phosphorylated groups.

The methods of the present invention may be achieved through use of in vitro and in vivo methods. The in vitro methods may be cell free or a cellular system. For example, BRKs can be isolated from cells (either endogenous or transfected/transformed BRKs) and assayed with a substrate for activity. A substrate can be particular to BRKs, or can be a generic substrate to simply determine if a kinase is active. The methods of the present invention also allow for determination of a dose and a time course for BRK activation following brassinosteroid activation of BRI1.

The present invention also provides methods for identifying BRKs in other eukaryotes, such as plants, that are not *Arabidopsis thaliana*. The BRKs may be identified in the other types of plants referenced herein. The BRKs may be identified in other *Arabidopsis*. Methods of identifying homologous proteins are known in the art. By way of example, primers to a known BRK nucleic acid may be used to isolate a BRK cDNA based on principles of hybridization and amplification. By way of further example, antibodies to BRKs may be used to isolate BRKs from cellular extracts.

Figure 6:
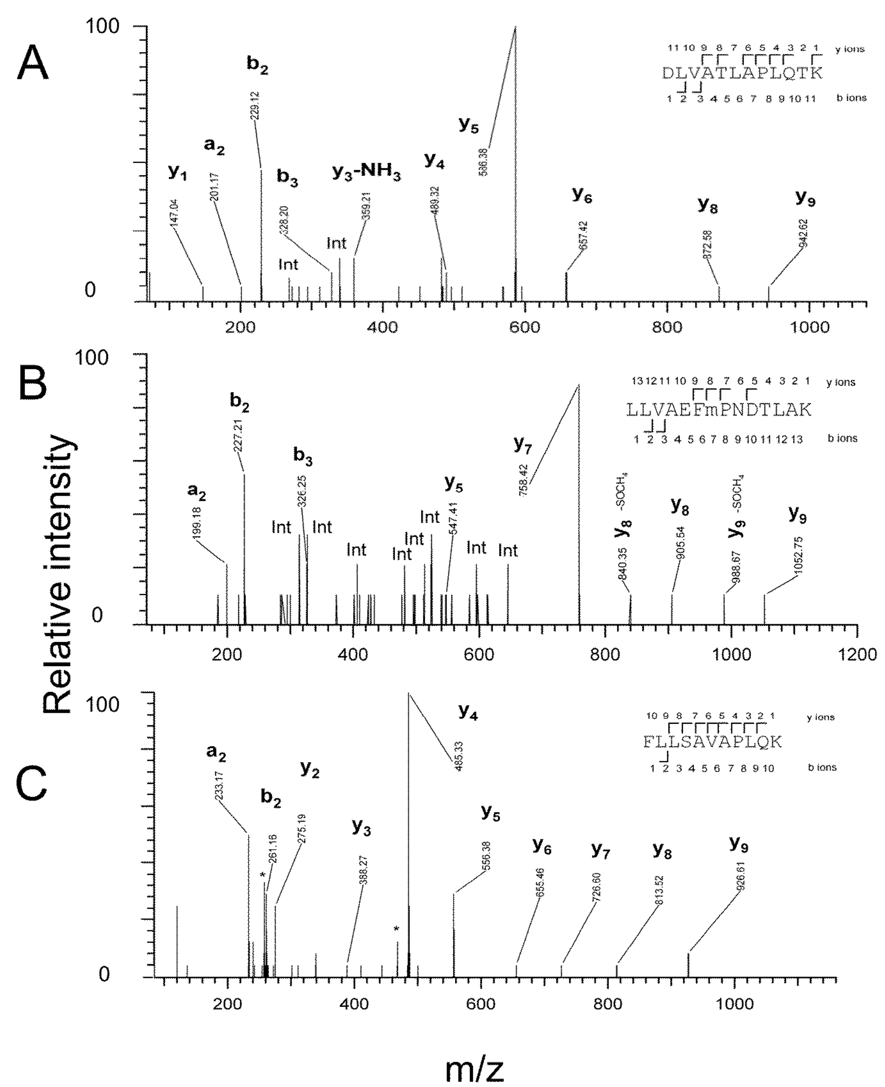
FIG. 6 shows a representative tandem mass spectra obtained from precursor ions with m/z value A) $593.8805+^{2}$, B) $635.3947^{+2}$, and C) $789.4522^{+2}$, corresponding respectively to: A), peptide DLVATLAPLQTK, spanning residues D322 to K333 of protein BRK1 (At4g35230); B), peptide LLVAEFmPNDTLAK, spanning residues L146 to K159 of protein BRK1 (At4g35230); C), peptide FLLSAVAPLQK, spanning residues F302 to K312 of protein BRK2 (At5g46570). The observed sequence ions are displayed. Water or ammonium losses are marked with stars. Int: internal ions. m: oxidized methionine.

The present invention provides methods for identifying compounds that interact with BRKs. These compounds may affect the kinase activity of a BRK, or the ability of BRK to interact or bind with a substrate, scaffold protein or cofactor. These compounds may affect the cellular processes typically associated with BRK activity. These compounds may affect plant growth, plant disease resistance, and plant fertility/sterility. These compounds may be substrates or cofactors of a BRK. These compounds may antagonize the activity of a BRK. These compounds may be an agonist for BRK activity. The interaction may be specific to a non-phosphorylated state of a BRK. The interaction may be specific to a phosphorylated BRK. The interacting protein may be a scaffold protein. Methods of identifying interacting proteins are known in the art. For example, by co-precipitation with BRKs. Optionally, co-precipitating proteins may be further separated such as by chromatography, e.g. FPLC, or by resolving by SDS-PAGE. Co-precipitating proteins may be identified by protein identification process such as amino-terminal sequencing (Edman degradation). Co-precipitating proteins may also be identified by digestion of the protein (e.g. trypsin, chymotrypsin, and endoproteases) followed by liquid chromatography (LC) and tandem mass spectrometry (MS/MS) or TOF (time of flight) analysis (see, e.g., examples below and FIGS. 6 and 8).

The present invention provides methods for determining the effects a test substrate has on brassinosteroid signaling comprising assaying the kinase activity of BRKs. For example, the test substrate may be an agonist for brassinosteroid signaling, acting on the receptor and stimulating activation of BRKs. The test substrate may be an antagonist to BRK signaling, inhibiting the ability of brassinosteroids to activate BRKs.

The present invention also provides methods for identifying compounds that modulate kinase activity of BRKs. The compounds may enhance the kinase activity of BRKs. The compounds may inhibit the kinase activity of BRKs. By way of example, compounds to inhibit BRKs can be identified through combinatorial chemistry, such as through the use of libraries of compounds. Such methods are known in the art.

Compounds that interact with BRK or modulate the kinase activity of BRK may be identified by various assays, such as competition assay, binding assay, kinase assay, or phosphatase assay. For example, a compound known to interact with BRK or known to modulate BRK, such as a brassinosteroid, may be used as a control in a competition assay or in a binding assay for comparison. For example, in a competition assay, a test compound may be mixed with the known compound and BRK to determine whether the test compound will compete with the known compound for interacting with BRK. In a binding assay, the binding affinity (and rates of association and disassociation, such as through a dose-response curve) of the test compound may be measured and compared with a control.

The present invention also provides for methods of identifying BRK kinases in other types of cells, more preferably other types of plant cells. The homology between BRKs in *Arabidopsis* and some other plant species are presented as an example herein. Those skilled in the art will recognize that primers aimed to conserved domains, more preferably to kinase domains will provide for identification of BRK-related kinase in other species of plants due to hybridization with the cDNA produced from active messenger RNA in the examined other cell type.

The present invention also provides methods of using BRK or fragments thereof as a scaffold protein. The phosphorylation status of the BRK protein may affect the ability of the BRK to function as a scaffold protein.

The present invention further provides for the kinase activity of the BRK to be regulated by brassinosteroid receptor kinases and other receptor kinases and chimeras thereof.

EXAMPLES

Materials and Methods

Materials

The det2-1 and bzr1-1D mutants are in *Arabidopsis thaliana* Columbia ecotype background, and bri1-5 is in the WS ecotype. For hypocotyl and root growth assay, seedlings were grown on vertical phytoagar plate containing 1/2 MS medium and 1% sucrose (pH 5.7) in the dark for 4 days or under continuous light for 7 days. Confocal microscopy and BiFC analysis were performed according to Gampala et al. (Gampala et al., Dev Cell 13, 177 (August, 2007)).

Plasma Membrane Isolation, 2-D DIGE, and Mass Spectrometry

Growth and BR treatment of det2 mutant seedlings, plasma membrane protein isolation, and 2D-DIGE and LC-MS/MS analyses were performed as described previously Tang et al. (Tang et al., *Mol Cell Proteomics* Epub ahead of print (Jan. 8, 2008)).

Immunoblotting of 2-DE

Leaves from 3-week-old transgenic det2 or bri1-5 mutant seedlings expressing the BRK1-YFP fusion protein were cut into two pieces along the middle vein. Each half was treated for 15 min with mock solution (0.01% ethanol) or 100 nM BL. Total protein was extracted and separated by 2-DE using a 7 cm or 24 cm pH 4-7 immobilized pH gradient gel (IPG) strip, and a 10% SDS PAGE gel. The proteins were blotted to a nitrocellulose membrane and detected using anti-YFP antibodies.

GST Tagged Protein Purification and In Vitro Phosphorylation Assays

GST tagged BRK1, BRK1-ΔTPR, BRK1-S230A, BRK3, BRI1 kinase domain (BRI1-KD), BAK1 kinase domain (BAK1-KD), kinase dead BRI1 (mBRI1-KD) or BAK1 kinase domain (mBAK1-KD), were expressed in *E. coli* and purified by standard procedure using glutathione agarose beads. In brief, 10 ml overnight grown BL 21 cells expression the desire constructs were transferred into 500 ml of LB and grown at 37 degree for three more hours. 0.5 mM IPTG was then added into the culture to induce the protein expression for two more hours. The bacteria cells were sonicated in PBS with 1% Triton X-100 and centrifuge at 20,000 g for 15 min to remove the insoluble cell debris. Supernatant was incubated with PBS pre-equilibrated glutathione agarose beads and rotate at cold room for 2 hours. After wash with PBS for 5 times, the GST tagged proteins were eluted using 5 mM Glutathione. Eluted protein was concentrated by ultrafiltration using centricon centrifuge tubes with a 10 kD molecular weight cut-off.

In vitro phosphorylation assays were performed in a mixture containing 20 MM Tris-Cl, pH 7.5, 10 mM $MgCl_2$, 100 mMNaCl, 1 mM DTT, 100 μM ATP, 10 μCi$^{32}$P-γATP and 0.5 μg GST-BRI1-KD or GST-BAK1-KD with or without 15 μg GST tagged BRKs. One microgram of GST tagged mBRI1-KD or mBAK1-KD was used. The reaction mixtures were incubated at 30° C. for 3 hr with constant shaking. Kinase reactions were stopped by adding equal volume of 2× SDS sample buffer and boiling for 5 minutes. The protein phosphorylation was analyzed by SDS-PAGE and autoradiography.

Anti-BRK1 Antibodies.

N terminal 87 amino acid of BRK1 were purified from *E coli* as a GST-fusion protein (GST-BRK1N87) following the procedure described above. Purified protein was separated using 12% SDS-PAGE. After Commassie Blue staining, GST-BRK1N87 protein was cutted from the gel and used to immunize rabbits. The antibodies were affinity purified using an antigen column containing immobilized GST-BRK1N87 protein. The antibodies specifically detect GST-BRK1 but not GST-BRK3.

Co-Immunoprecipitation:

All procedures were performed at 4° C. Rosette leaves of 3-week-old *Arabidopsis* plants were homogenized with mortar and pestle in the grinding buffer (20 mM HEPES, pH 7.5, 40 mM KCl, 250 mM sucrose, 5 mM $MgCl_2$ and protein inhibitors) at a ratio of 3 mL buffer per gram of tissue. Homogenate was filtered through 2 layers of Miracloth (CalBiochem, La Jolla, Calif.), and centrifuged at 10,000 g for 10 minutes. The supernatant was further centrifuged at 100,000 g for 60 min to pellet the microsomal fraction. Microsomes were re-suspended in 0.5 mL grinding buffer and sonicated for 10 sec. Triton X-100 was added to a final concentration of 1%. After mixing, the extracts were centrifuged at 20,000 g for 10 min. Supernatant was diluted 5 times with grinding buffer to reduce Triton X-100 to 0.2%. Affinity-purified anti-YFP or anti-BRK1 antibodies bound to Protein A Sepharose beads were added, and the mixture was rotated in a cold room for 30 min. Beads were washed 6 times with 0.5 mL grinding buffer each and eluted by boiling directly with SDS sample buffer for 5 min. Samples were analyzed by SDS-PAGE and immunoblotting.

Knockout Mutants of BRKs.

T-DNA knockout mutants Salk_001600 (brk2-3), Salk_105500 (brk2-2), Salk_096500 (brk3-1), Salk 032845 (brk4), Salk_074467 (brk5), Salk_051462 (brk12) were obtained from the *Arabidopsis* Biological Resource Center (ABRC, www.*Arabidopsis*.org) (Alonso et al., *Science* 301, 653 (Aug. 1, 2003)). Mutants were first genotyped with gene specific primers and T-DNA primer LBb1 5'-GCGTGGACCGCTTGCTGCAACT-3' to confirm the position of T-DNA insertion site. The primers used for different brk knockouts were: BRK2-2GR: CAAACTCAGGGACGCTTATTCT; BRK2-F: CACCATGGGTTGTTTACATTCCAAAACTGC; BRK1-3GF: CGAATCGCAGACTATATTGCAG; BRK1-3GR: ATGTGTTTGCCGCTTAAAAGAT; BRK3-1GF: TGCTTCGATTCCCAAAATTTAC; BRK3-IGR: ATATACTCCACGGCAAAACCAG; BRK4-1GF: AATAGTCGGGATGGGAAAAGTT; BRK4-IGR: ACTTTGAGGCAGACCCATTAGA; BRK5-2GF: CATTTCTCAAACGATGATGGAA; BRK5-2GR: ATTTGCTACACCCTCGTCATCT; BRK12-GR: TGTTGCAATAATCCAATGCTTC; BRK12-F: CACCATGGGTTGTTGTTACTCACTATCTTC. Expression of BRK3 RNA in wild type and brk3-1 mutant was analyzed by RT-PCR (30 cycles) using gene specific primer pairs: BRK3-F, ATGGGAGGTCAATGCTCTAGCCTGAGT and BRK3-R, CTTCACTCGGGGAACTCCATTCATCTTTG.

Overexpression of BRKs

Full-length cDNA coding sequences of BRKs without the stop codon were amplified by PCR using gene-specific primers and full-length cDNA clones as templates (BRK1: U14968, BRK2: U67754, BRK3: U16452, BRK5: U85779, BRK6: U16452) (Yamada et al., *Science* 302, 842 (Oct. 31, 2003)). The cDNAs were cloned into pENTR/SD/D-TOPO vectors (Invitrogen), and then sub-cloned between the 35S promoter and YFP coding sequence in the destination plasmid pEarleyGate 101 (Earley et at, *Plant J* 45, 616 (February, 2006)), or between the 35S promoter and the 4× Myc tag in the pGWB17 vector, using Gateway recombination cloning reaction (Invitrogen). The fusion constructs were transformed into *Agrobacterium* strain GV3101 and then transformed into *Arabidopsis* plants by floral dipping.

Quantitative Reverse-transcription PCR

Total RNA extraction and quantitative real-time RT-PCR analysis of DWF4 expression was performed as described by He et al. (He et al., *Science* 307, 1634 (Mar. 11, 2005)).

Method for Measurement of Hypocotyls or Root Length.

*Arabidopsis* seeds were surface sterilized by first soaking in 70% ethanol plus 0.1% Triton X-100 for 15 min followed by soaking in 96% ethanol for another 10 mins. Sterilized seeds were air dried in the hood and sowed on agar plate of Murashige and Skoog (MS) medium or MS plate plus BRZ or Brassinolide. The seeds were incubated at 4° C. for 3 days to synchronize germination and then grown for 4 days in dark or 7 days under continuous light before taking pictures for measurement. For measurement of hypocotyls or root growth, the plates were first scanned using a image scanner at a resolution of 300 dpi, and the images were input into computer software Image J to measure the root or hypocotyl length.

For the function of S230 of BRK1, bri1-5 mutants were transformed with S230A and S230E mutant version of BRK1.

Results

Figure 7A:
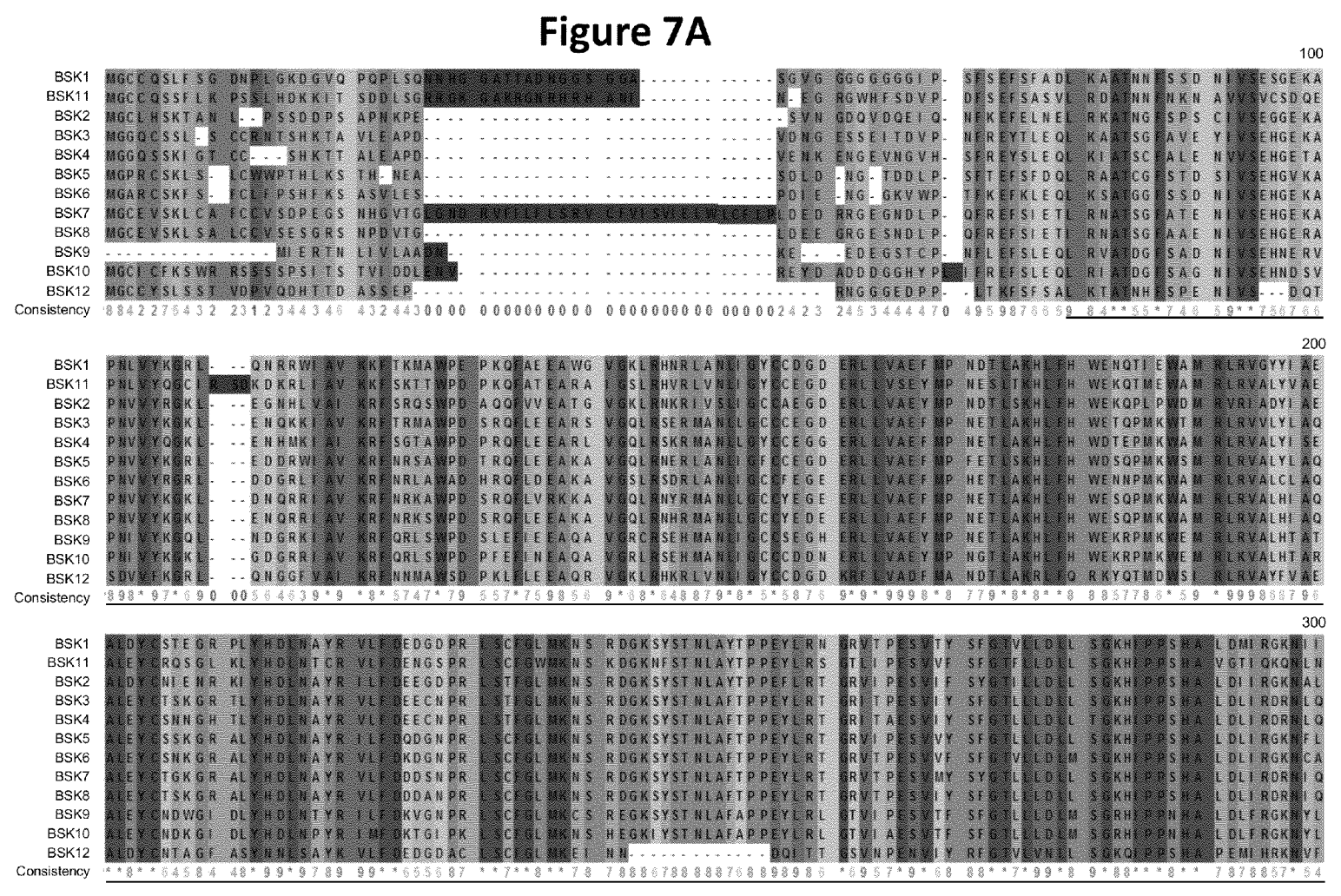

To identify additional components of the BR signaling pathway, we performed quantitative proteomic studies of BR-responsive proteins using two-dimensional difference gel electrophoresis (2-D DIGE). Seedlings of BR-deficient det2-1 mutant were treated with brassinolide (the most active form of brassinosteroids) or mock solution, and proteins were labeled with Cy3 or Cy5 dyes, mixed together, and separated in the same gel by two-dimensional gel electrophoresis (2-DE). Brassinolide-induced BAK1 phosphorylation and BZR1 dephosphorylation were detected in the plasma membrane and phosphoprotein fractions, respectively (Tang et al., *Mol Cell Proteomics* 7, 728 (2008)), but not in total proteins (Deng et al., *Mol Cell Proteomics* 6, 2058 (December, 2007)). Similar to BAK1, two additional rows of spots showed BR-induced increase of the acidic forms and decrease of the basic forms (FIGS. 1A and B), which is consistent with BR-induced phosphorylation. Mass spectrometry analysis of these spots identified two kinases encoded by *Arabidopsis* genes At4g35230 and At5g46570, which we named BR-regulated kinase 1 and 2 (BRK1 and BRK2) (FIG. 1B and fig. S2). BRK1 and BRK2 share 60% amino acid sequence identity (FIG. 7), and are members of the receptor-like cytoplasmic kinase sub-family RLCK-XII (Shiu et al., *Plant Cell* 16, 1220 (May, 2004)). The RLCK-XII sub-family includes twelve *Arabidopsis* proteins that each contains a kinase domain at the N-terminal side and tetratricopeptide repeat (TPR) domains at the C-terminus (FIG. 7) (Shiu et al., *Plant Cell* 16, 1220 (May, 2004)). TPR domains are known to mediate protein-protein interactions and are present in components of steroid receptor complexes in animals (Smith, *Cell Stress Chaperones* 9, 109 (Summer, 2004)). BRK1 and BRK2 do not contain predicted transmembrane domains but have putative N-terminal myristylation sites (glycine 2) that could mediate their membrane localization (FIG. 7).

The BR-induced shift of BRK1 from basic to acidic side in 2-DE gels was confirmed by immunoblotting of transgenic plants expressing a BRK1-YFP (yellow fluorescence protein) fusion protein (FIGS. 1C and 1E). The response was significantly weaker in the bri1-5 mutant background (FIGS. 1D and 1E), suggesting that BR regulation of BRK1 is BRI1 dependent. Consistent with their identification in the plasma membrane fractions, BRK1-YFP fusion proteins showed localization on the cell surface and the localization is not affected by brassinolide treatment (FIG. 1F).

Figure 2:
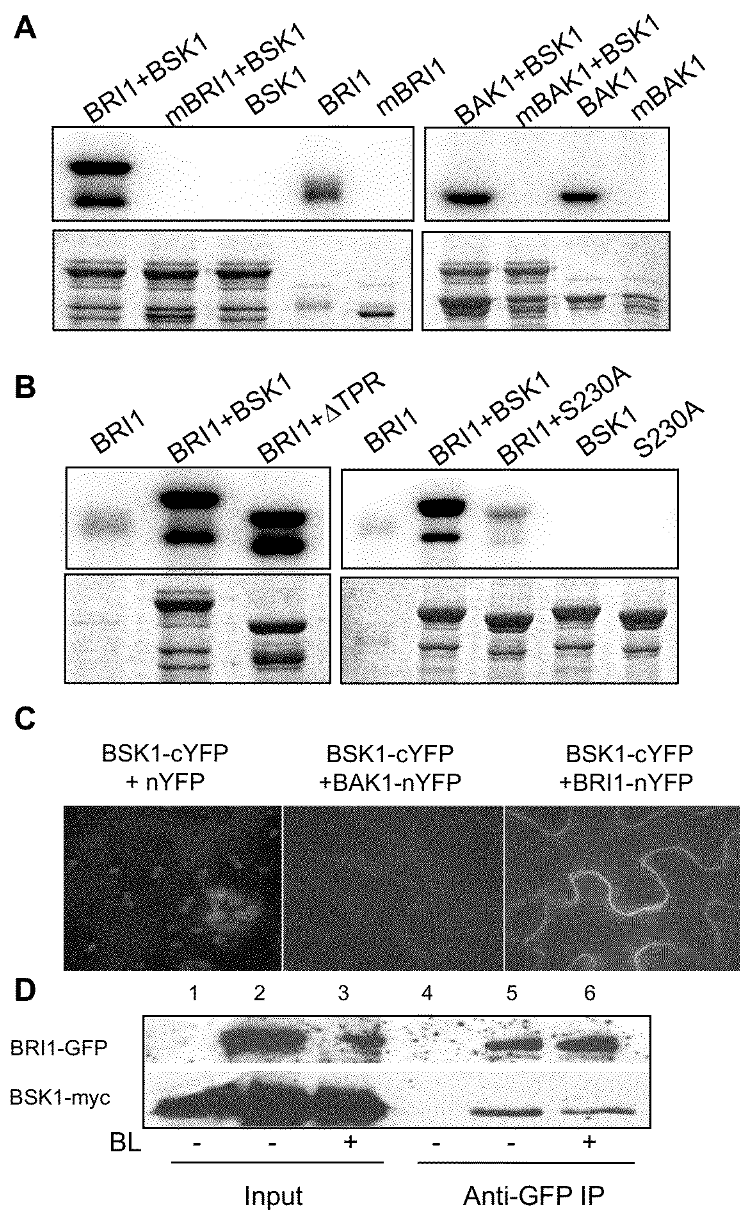
FIGS. 2A-2D show BRK1 is a substrate of BRI1.
Figure 8:
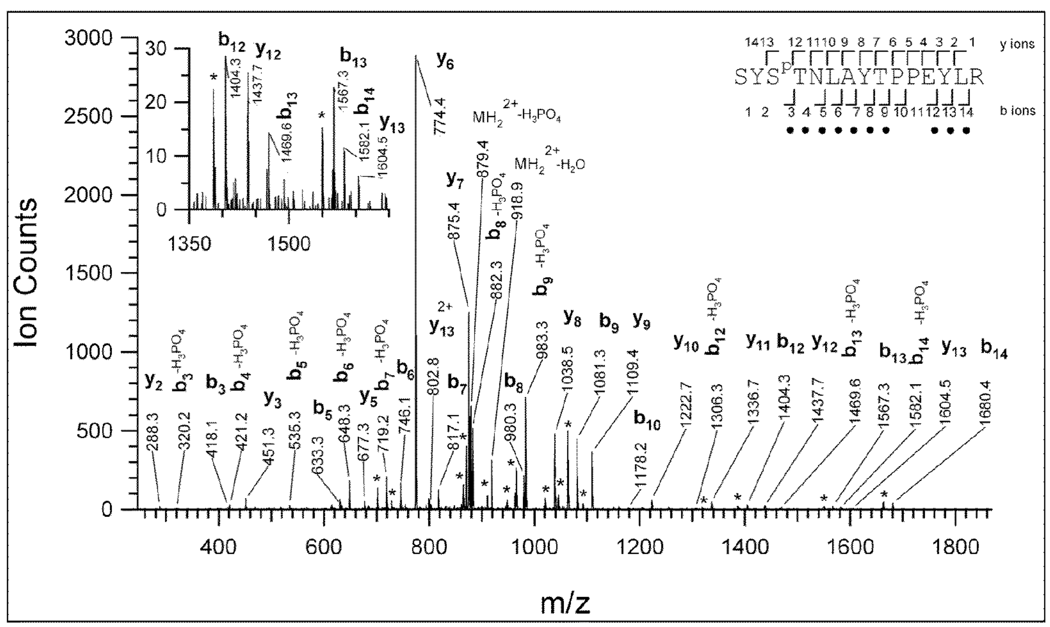
FIG. 8 shows mass spectrometry analysis of BRI1 phosphorylation of BRK1. GST-BRI1-KD and GST-BRK1 proteins were expressed and purified in *E coli*, and mixed in an in vitro kinase reaction. The proteins were then digested by trypsin and analyzed by LC-MS/MS. Shown is a representative tandem mass spectrum obtained from precursor ions for peptide SYSTNLAYTPPEYLR, spanning the residues Ser-228 to Arg-242 of BRK1. The phosphorylated residue (S230) is indicated in the peptide sequence as Sp. Phosphate losses are marked with dots.

The plasma membrane localization and BR-induced modification of BRKs suggest that they might be substrates of BRI1 or BRI1's co-receptor kinase BAK1 (Nam et al., *Cell* 110, 203 (Jul. 26, 2002); Li et al., *Cell* 110, 213 (Jul. 26, 2002)). In vitro kinase assays demonstrated that BRI1, but not BAK1, phosphorylates BRK1 (FIG. 2A). Mass spectrometry analysis of BRI1-phosphorylated BRK1 identified serine 230 of BRK1 as a BRI1 phosphorylation site (FIG. 8). This same residue is also phosphorylated in vivo (Niittyla et al., *Mol Cell Proteomics* 6, 1711 (October 2007)). While deletion of the C-terminal TPR domain has no effect on BRK1 phosphorylation by BRI1, a S230A mutation reduced the phosphorylation by 82% (FIG. 2B), indicating that S230 is the major site for BRI1 phosphorylation.

Figure 9:
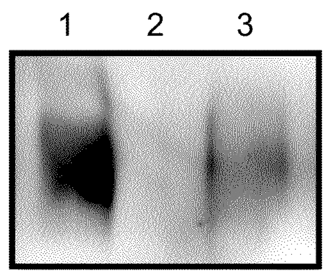
FIG. 9 shows co-immunoprecipitation of 1313111 with BRK1. Microsomal proteins (Input, lane 1) from det2 mutant plants expressing BRI1-GFP under the control of BRI1 promoter were immunoprecipitated (IP) using polyclonal anti-BRK1 antibodies affinity-purified using an BRK1 antigen column (lane 3). Protein A bead alone was used as IP control (lane 2). Immunoblots were probed using anti-GFP antibodies. BRI1-GFP can be pulled down by anti-BRI1 antibody but not by protein A bead.

In vivo interactions with BRI1 were demonstrated using bimolecular fluorescence complementation (BiFC) and co-immunoprecipitation assays. While cells co-expressing BRK1 fused to the C-terminal half of YFP (BRK1-cYFP) and non-fusion N-terminal half of YFP (nYFP) or BAK1-nYFP fusion showed no or weak fluorescence signals (FIG. 2C), cells co-expressing BRI1-nYFP and BRK1-cYFP showed strong BiFC fluorescence at the plasma membrane (FIG. 2C). Anti-BRK1 antibodies immunoprecipitated the BRI1-GFP protein expressed from the BRI1 promoter (FIG. 9), and a BRK1-myc protein was immunoprecipitated by anti-GFP antibodies only in transgenic *Arabidopsis* plants expressing both BRI1-GFP and BRK1-myc (FIG. 2D). BR-treatment reduced the amount of the co-immunoprecipitated BRK1-myc to 46% of the untreated sample (FIG. 2D), suggesting that BRK1 might be released from BRI1 upon phosphorylation. These results indicate that BRK1 is a BRI1 kinase substrate that is phosphorylated upon BR activation of BRI1.

Figure 3:
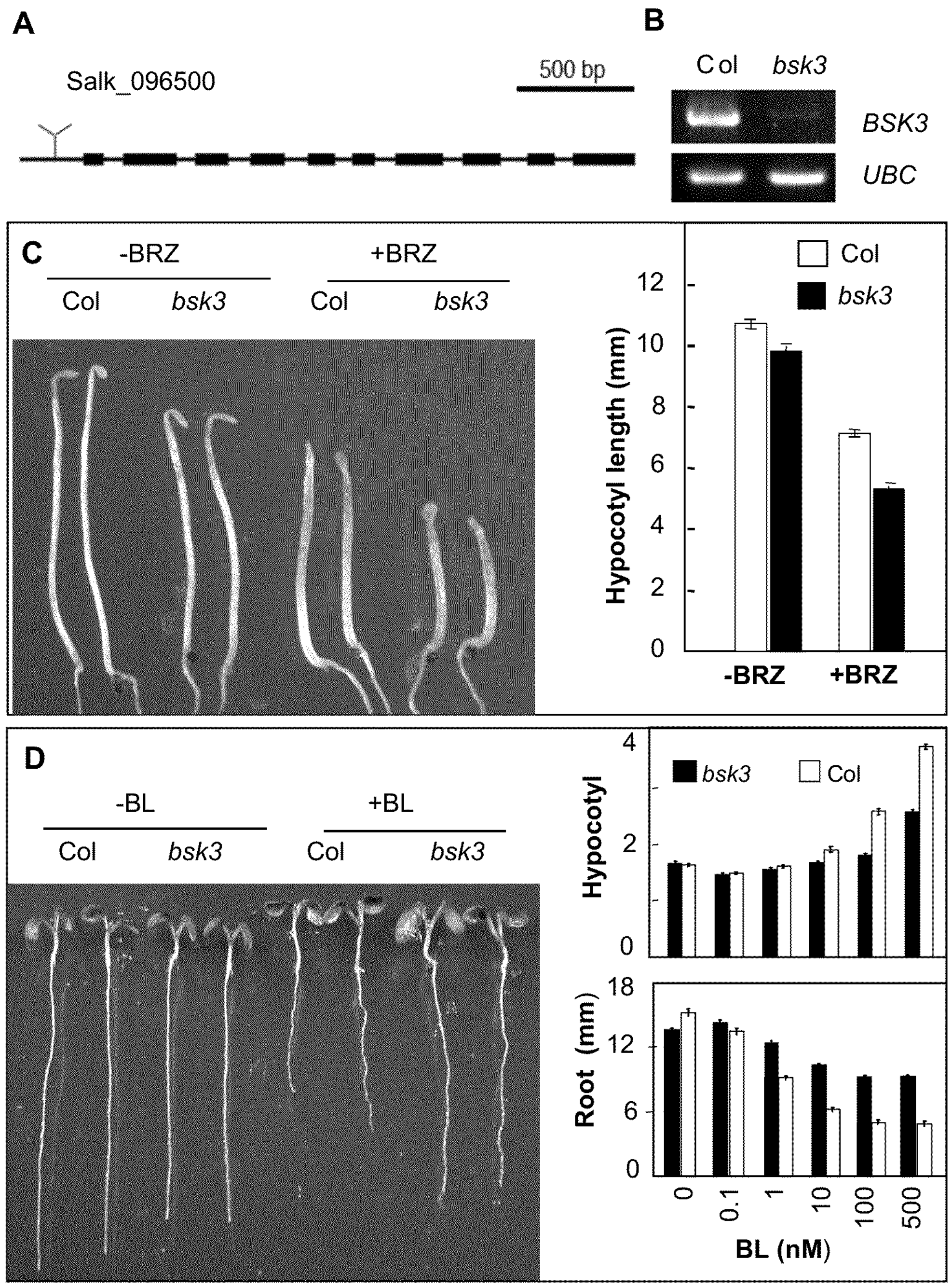
FIGS. 3A-3D show the brk3-1 mutant has reduced BR sensitivity.
Figure 10:
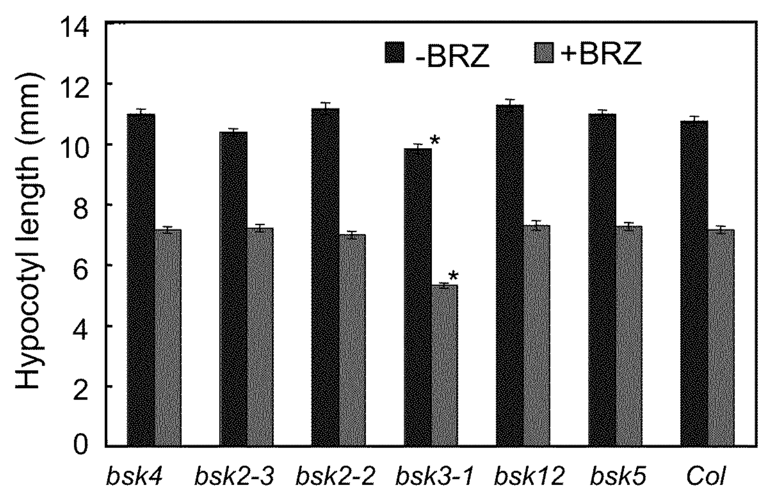
FIG. 10 shows the T-DNA insertion mutant brk3-1 shows short-hypocotyl phenotypes when grown in the dark. Seedlings of wild type (Col) and mutants were grown in the dark on regular medium (−BRZ) or medium containing 2 μM brassinazole (+BRZ). Error bars show standard errors. Stars mark statistically significant differences from Col.
Figure 11:
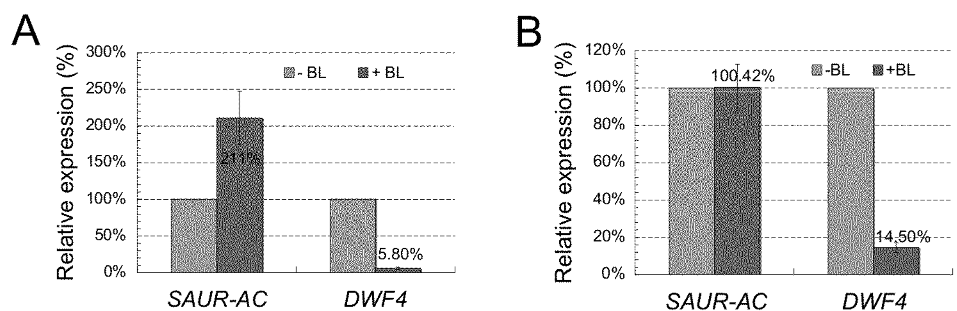
FIG. 11 shows BL responsiveness of SAUR-AC and DWF4 expression is reduced in brk3-1 knockout. Col (A) and brk3 (B) seedlings were grown on 1/2× MS medium for 5 days under continuous light and treated with mock solution or 100 nM BL for 2 hrs. mRNA was extracted and the expression level of SAUR-AC and DWF4 genes were analyzed by real time RT-PCR. The data represent the average from 4 independent biological repeats. Error bars represent standard deviation.
Figure 12:
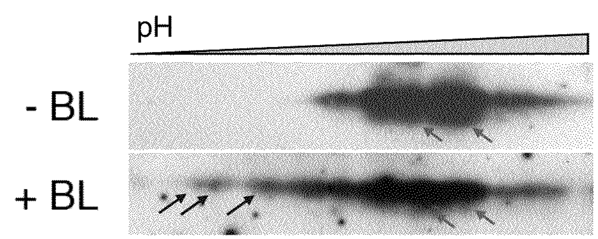
FIG. 12 shows BL regulates the post-translational modification of BRK3. One-week-old det2 seedlings expressing a BRK3-YFP under the control of 35S promoter were treated with 100 nM BL or mock solution for 1 hr. Microsomal protein were isolated and separated by IEF using a 7 cm pH 4-7 IPG strip, followed by 10% SDS-PAGE. After transferring to nitrocellulose membrane, BRK3-YFP protein were detected using GFP antibody. Blue arrows show new BRK3-YFP spots induced after BL treatment. Arrows showed spots that show reduced intensity after BL treatment.
Figure 13:
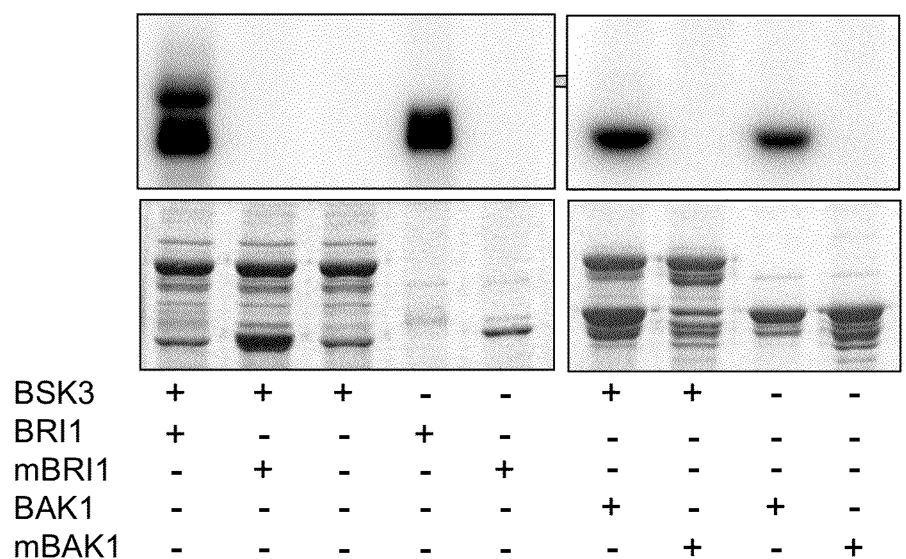
FIG. 13 shows BRK3 can be phosphorylated by BRI1, but not by BAK1 in vitro. In vitro kinase assays were performed by incubating the full-length BRK3, BRI1 kinase domain and BAK1 kinase domain, individually or in combination as shown. All three proteins were purified from *E. coil* as GST fusion proteins. Upper gel image shows autoradiography of $^{32}P$ labeling, and the lower image shows total protein stained by Coomassie Brilliant Blue.
Figure 14:
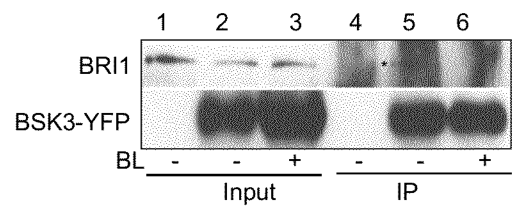
FIG. 14 shows co-immunoprecipitation of BRI1 with BRK3. Microsomal proteins (Input) from det2 mutant plants (lane 1 and 4) or det2 expressing BRK3-YFP (lanes 2, 3, 5 and 6) were immunoprecipitated (IP) using anti-YFP antibodies. Immunoblots were probed using anti-BRI1 or anti-GFP antibodies. Seedlings were either treated with mock solution (BL−) or with 100 nM brassinolide (BL+) for 30 minutes. Band of BRI1 in IP of the mock-treated sample (lane 5) is marked with a star, and this band is not detected in IP of the BL-treated sample (lane 6).
Figure 15:
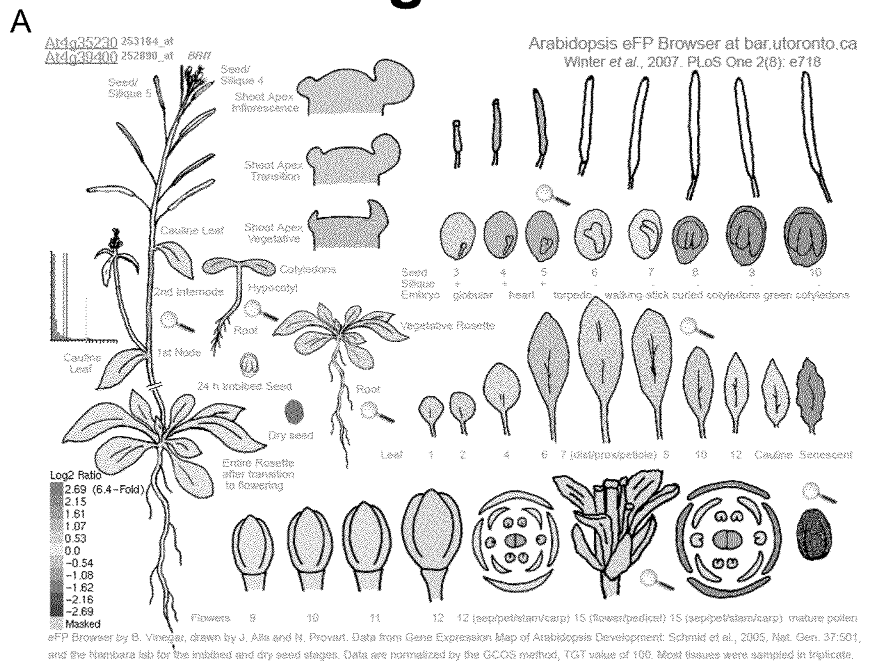
FIG. 15 shows a comparison of tissue specific expression between BRK1 and BRI1 (A), or between BRK3 and BRI1 (B). Figures were generated on line using e-FP browser from at bbc.botany.utoronto.ca/efp/cqi-bin/efpWeb.cyi (Winter et al., PLoS One 2(8): e718 (2007)). Relative expression levels of BRK vs BRI1 in various organs are shown.
Figure 15:
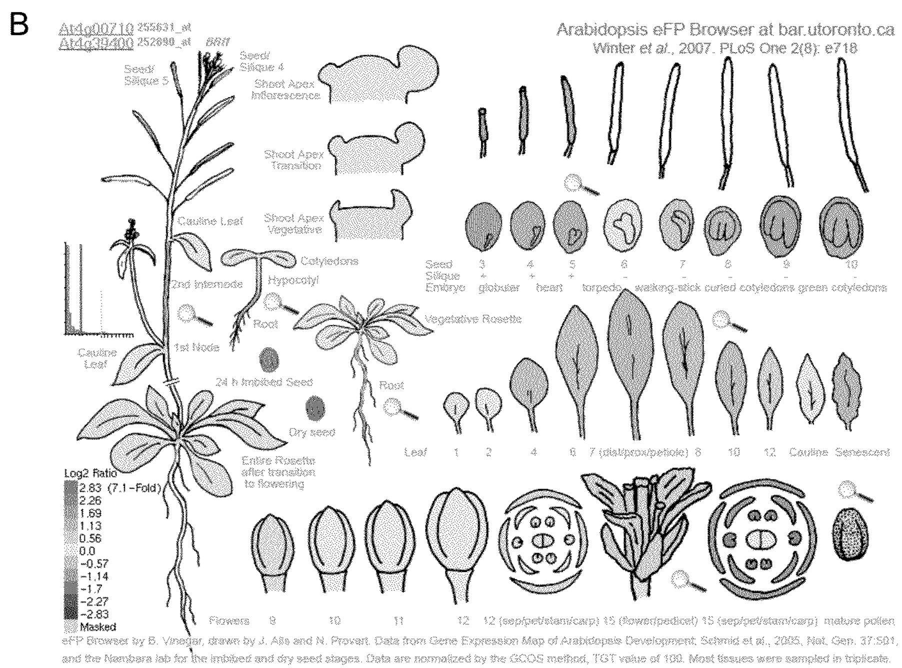

To determine the functions of BRK and their homologs in BR signaling, T-DNA insertion mutants were obtained for BRK2, BRK3, BRK4, BRK5, and BRK12 genes (Alonso et al., *Science* 301, 653 (Aug. 1, 2003)). Of these, only the brk3-1 mutant showed an obvious phenotype (FIG. 10). The brk3-1 mutant contains a T-DNA insertion in the 5' untranscribed region and expresses much reduced level of the BRK3 RNA (FIGS. 3A and 3B). The brk3-1 mutant seedlings grown in the dark on regular medium or medium containing the BR biosynthetic inhibitor brassinazole (BRZ) showed shorter hypocotyl length than wild type seedlings (FIG. 3C). Brassinolide treatment increases hypocotyl elongation and inhibits root growth in wild type plants grown in the light. Compared to wild type, the brk3-1 mutant showed reduced responses to BL in hypocotyl elongation, root inhibition, and expression of BZR1-target gene DWF4 and BES1 target-gene SAUR-Ac (FIGS. 3D and 11). These results demonstrate that loss-of-function mutation of brk3 reduces BR sensitivity, indicating essential role of BRK3 in BR signaling. Similar to BRK1, the BRK3 protein is also regulated by brassinosteroid (fig. S8), phosphorylated by BRI1 kinase in vitro (FIG. 13), and interacts with BRI1 in a BR-dependent manner in vivo (FIG. 14). BRK1 and BRK3 are expressed in similar tissues as BRI1 (FIG. 15). These results suggest that BRK3 and its homologs play redundant or overlapping roles in BR signaling, which could explain the weak BR-insensitive phenotypes of brk3-1.

Figure 16:
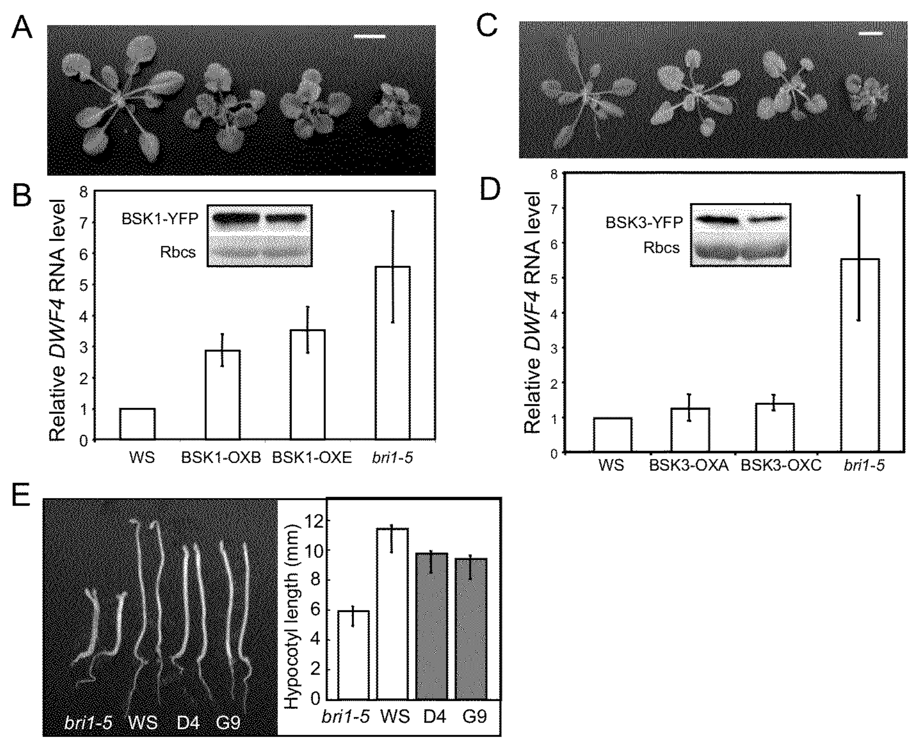
FIG. 16 shows overexpression of BRK1 and BRK3 suppresses the bri1-5 mutant. A. Phenotypes of three-week-old wild type (WS, left), bri1-5 (right), and bri1-5 overexpressing BRK1-YFP (middle two). B. Expression of the DWF4 RNA determined by quantitative RT-PCR. Insert shows immunoblot of BRK1-YFP and staining of Rubisco in the two transgenic lines. C and D, same as A and B, but for overexpression of BRK3-YFP. Bars in A and C are 5 mm. E. Overexpression of BRK3 (line D4 and G9) suppresses dark-grown phenotypes of bri1-5. Seedlings were grown on MS medium in the dark for 4 days.
Figure 17:
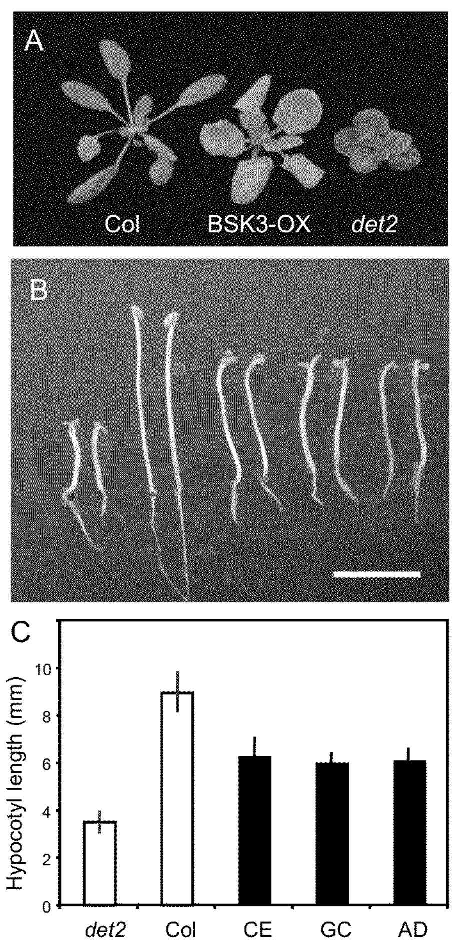
FIGS. 17A-17C show overexpression of BRK3 suppresses the det2-1 mutant. A. Three-week-old wild type (Col), det2-1 mutant overexpressing BRK3-YFP (BRK3-ox), and det2-1. B and C, Seedlings of det2-1, Col, and three independent lines (CE, GC, AD) of det2-1 transformed with 35S-BRK3-YFP were grown in the dark for 4 days. Bar in panel B is 5 mm.

When overexpressed in the BR-insensitive bri1-5 mutant (FIG. 4A, 4B and FIG. 16) or BR-deficient det2-1 (FIG. 17) mutant backgrounds, BRK1, BRK3, and BRK5 obviously suppressed the dwarf phenotypes of the mutants. Consistent with reduced BR sensitivity of the brk3-1 mutant, over expression of BRK3 is most effective in rescuing the bri1 phenotypes. The growth phenotypes correlated with altered expression of the BZR1-target gene DWF4 (FIGS. 4C and 16), indicating that overexpression of the BRKs activates downstream BR signaling. Overexpression of BRK3 partly suppressed the dwarf phenotype of the null allele bri1-116 (FIG. 4D), but not that of the bin2-1 mutant (FIG. 4E), indicating that BRK3 functions downstream of BRI1 but upstream of BIN2, which is consistent with BRK3 being a substrate of the BRI1 kinase.

Figure 4:
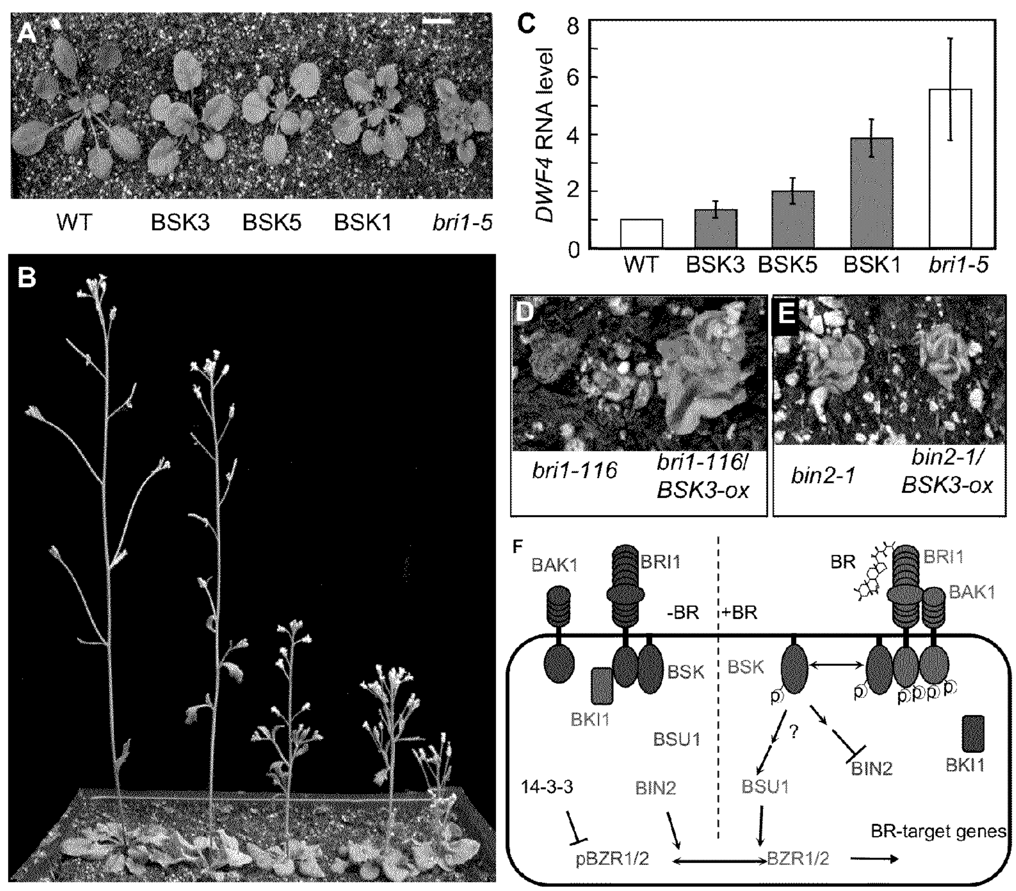
FIGS. 4A-4F show BRKs function downstream of BRI1 but upstream of BIN2 in the BR signaling pathway. Phenotype of light grown three-week-old (FIG. 4A) or five-week-old (FIG. 4B) wild type, bri1-5, or transgenic bri1-5 overexpressing BRK3, BRK5, or BRK1 as YFP fusion proteins.

Using quantitative proteomics, we identified BRKs as new BR signal transduction components. This study demonstrates that sample pre-fractionation followed by 2-D DIGE is a powerful proteomic approach for dissecting signaling pathways. While only BRK1 and BRK2 were identified in the proteomic study, additional members (BRK3 and BRK5) of this family of RLCKs appear to play similar role in BR signaling. These results support a model for the function of BRKs in BR signaling (FIG. 4F). In the absence of BR, BRKs are associated with BRI1. Upon BR activation of BRI1, BRKs are phosphorylated and then disassociate from the receptor complex to activate downstream signaling. Such ligand-induced disassociation from a pre-existing receptor complex potentially provides faster signaling than ligand-induced recruitment of a free component into the receptor complex.

Both BRKs and BAK1 are substrates of the BRI1 kinase, but several lines of evidence support that they play distinct roles in BR signaling. First, BR induces BRI1-BAK1 interaction (Wang et al., *Plant Cell* 17, 1685 (June, 2005)) but reduces BRI1-BRK1 and BRI1-BRK3 interactions. Second, overexpression of BRK3 suppresses the bri1-116 null allele, whereas overexpression of BAK1 only suppresses weak alleles but not a strong allele of bri1 nor a double mutant containing the weak bri1-5 allele and the BR-biosynthetic mutation det2-1 (Li et al., *Cell* 110, 213 (Jul. 26, 2002)), suggesting that BRK3 functions downstream of BRI1 whereas BAK1's action on downstream BR response requires a functional BRI1. BAK1 and its homolog BKK1 are required in additional signaling pathways and BAK1 is also a co-receptor for the FLS2 receptor kinase, a receptor for flagelin, suggesting that BAK1 is not a specific component of the BR pathway (He et al., *Curr Biol* 17, 1109 (Jul. 3, 2007); Kemmerling et al., *Curr Biol* 17, 1116 (Jul. 3, 2007); Chinchilla et al., *Nature* 448, 497 (Jul. 26, 2007); Heese et al., *Proc Natl Acad Sci USA* 104, 12217 (Jul. 17, 2007, 2007)). BAK1 most likely mediates activation of BRI1 kinase rather than signal transduction to specific downstream components in the BR signaling pathway. In contrast, the BRKs directly mediate signal transduction from BRI1 to downstream BR responses (FIG. 4F). Identification of the downstream direct targets of BRKs will be the key to fully understanding how BR signal is transduced from the cell surface to the nuclear transcription factors.

We claim:

1. A fusion protein comprising a brassinosteroid receptor regulated kinase (BRK) polypeptide comprising the amino acid sequence $X_1X_2STNLAX_3X_4PPEYLR$ (SEQ ID NO: 25), wherein $X_1$ is either serine, arginine, or isoleucine, $X_2$ and $X_3$ are either tyrosine or phenylalanine, and $X_4$ is either threonine or alanine.

2. The fusion protein of claim 1, wherein the serine at amino acid position three is phosphorylated.

3. fusion protein of claim 1, wherein the sequence comprises a serine to alanine mutation at amino acid position three.

4. The fusion protein of claim 1, wherein the sequence comprises a mutation, wherein the mutation comprises a glutamic acid or aspartic acid at amino acid position three.

5. An immunogenic composition, comprising the fusion protein of claim 1, together with a pharmaceutically acceptable carrier.

6. A transgenic plant comprising the fusion protein of claim 1.

7. The fusion protein of claim 1, wherein the polypeptide comprises an amino acid sequence of at least 95% sequence identity to SEQ ID NO: 2, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20 or SEQ ID NO: 22.

8. A polypeptide consisting of SEQ ID NO: 25.

9. A brassinosteroid receptor regulated kinase (BRK) polypeptide comprising an amino acid sequence that is at least 95% identical to an amino acid sequence selected from the group consisting of SEQ ID NO: 6, SEQ ID NO:8, SEQ ID NO: 10, SEQ ID NO: 12, SEQ ID NO: 14, SEQ ID NO: 16, SEQ ID NO: 18, SEQ ID NO: 20 or SEQ ID NO: 22.

10. A method for modulating a cellular process of a plant cell comprising introducing the brassinosteroid receptor regulated kinase (BRK) polypeptide of claim 9 into the plant cell by transforming the plant cell with a nucleic acid molecule encoding the BRK polypeptide.

11. The method of claim 10, wherein the cellular process is cell expansion, cell elongation, cell division, cell growth, protection of the cell during exposure to cold, protection of the cell during exposure to heat, protection of the cell during drought, acceleration of senescence of the cell when it is dying, promotion of vascular differentiation, cell wall regeneration, or pollen elongation.

12. The method of claim 10 wherein the cellular process is inhibited as compared to a control.

13. The method of claim 10, wherein the cellular process is enhanced as compared to a control.

14. The method of claim 10, wherein the BRK polypeptide is mutated so that the kinase activity of the BRK polypeptide is inhibited.

15. The method of claim 10, wherein the kinase activity of the polypeptide BRK is inhibited by mutating a serine residue that is phosphorylated to an alanine residue.

16. The method of claim 10, further comprising contacting the cell with a brassinosteroid.

17. The BRK polypeptide of claim 9, wherein the amino acid consists of the amino acid sequence of an amino acid sequence selected from the group consisting of SEQ ID NO: 6, SEQ ID NO:8, SEQ ID NO: 10, SEQ ID NO: 12, SEQ ID NO: 14, SEQ ID NO: 16, SEQ ID NO: 18, SEQ ID NO: 20 or SEQ ID NO: 22.

* * * * *